United States Patent
Yokota et al.

(10) Patent No.: US 10,745,725 B2
(45) Date of Patent: Aug. 18, 2020

(54) METHOD FOR PRODUCING L-AMINO ACID BY INCREASING FRUCTOSE UPTAKE

(71) Applicant: AJINOMOTO CO., INC., Tokyo (JP)

(72) Inventors: Kosuke Yokota, Kanagawa (JP); Kazuyuki Hayashi, Kanagawa (JP)

(73) Assignee: AJINOMOTO CO., INC., Tokyo (JP)

(*) Notice: Subject to any disclaimer, the term of this patent is extended or adjusted under 35 U.S.C. 154(b) by 0 days.

(21) Appl. No.: 15/937,336

(22) Filed: Mar. 27, 2018

(65) Prior Publication Data
US 2018/0282773 A1    Oct. 4, 2018

(30) Foreign Application Priority Data
Apr. 3, 2017   (JP) .................................. 2017-073937

(51) Int. Cl.
| | |
|---|---|
| *C12P 13/14* | (2006.01) |
| *C12P 13/24* | (2006.01) |
| *C12P 13/10* | (2006.01) |
| *C12N 9/88* | (2006.01) |
| *C12N 15/52* | (2006.01) |

(52) U.S. Cl.
CPC ............... *C12P 13/14* (2013.01); *C12N 9/88* (2013.01); *C12N 15/52* (2013.01); *C12P 13/10* (2013.01); *C12P 13/24* (2013.01); *C12Y 102/04002* (2013.01); *C12Y 207/01004* (2013.01); *C12Y 402/01009* (2013.01)

(58) Field of Classification Search
None
See application file for complete search history.

(56) References Cited

U.S. PATENT DOCUMENTS

| | | | | |
|---|---|---|---|---|
| 9,045,789 B2 * | 6/2015 | Nishio | ....................... | C12P 7/50 |
| 9,506,094 B2 * | 11/2016 | Hirano | .................... | C07K 14/34 |
| 2006/0141588 A1 * | 6/2006 | Nakamura | ............. | C07K 14/34 435/110 |
| 2010/0099152 A1 * | 4/2010 | Chinen | ................ | C12N 9/1029 435/107 |
| 2011/0256598 A1 | 10/2011 | Eliot et al. | | |
| 2017/0121743 A1 | 5/2017 | Hirano et al. | | |

FOREIGN PATENT DOCUMENTS

| | | |
|---|---|---|
| WO | WO2006/016705 A1 | 2/2006 |
| WO | WO2006/070944 A2 | 7/2006 |
| WO | WO2015/013334 A1 | 1/2015 |

OTHER PUBLICATIONS

Accession D5NZS2. Jul. 13, 2010 (Year: 2010).*
Accession D4GL70. May 18, 2010 (Year: 2010).*
Nakamura et al. Appl. Environ. Microbiol. 2007, 73(14):4491-4498 (Year: 2007).*
Accession Q8G5P5. Mar. 1, 2003 (Year: 2003).*
Accession AEI65237. Aug. 24, 2006 (Year: 2006).*
Database UniProt [Online], Jan. 18, 2017, Fukuda, S., et al., "Full=Putative sugar kinase," XP002783307, Database accession No. E8ME04.
Database UniProt [Online], Mar. 15, 2017, Hara, Y., et al., "Full= Probable manno(Fructo)kinase Mak," XP002783308, Database accession No. A0A0H3KTH8.
Database UniProt [Online], Nov. 30, 2016, Hara, Y., et al., "Full= Fructokinase ScrK," XP002783309, Database accession No. A0A0H3L6L3.
Extended European Search Report for European Patent App. No. 18164967.4 (dated Aug. 21, 2018).
Caescu, C. I., et al., "Bifidobacterium longum Requires a Fructokinase (Frk; ATP:D-Fructose 6-Phosphotransferase, EC 2.7.1.4) for Fructose Catabolism," J. Bacteriol. 2004;186(19):6515-6525.
Kornberg, H., et al., "A route for fructose utilization by *Escherichia coli* involving the fucose regulon," PNAS 2006;103(51):19496-19499.
U.S. Appl. No. 15/717,042, filed Sep. 27, 2017, Moriya et al.

* cited by examiner

Primary Examiner — Christian L Fronda
(74) Attorney, Agent, or Firm — Cermak Nakajima & McGowan LLP; Shelly Guest Cermak

(57) ABSTRACT

A method for producing an L-amino acid such as L-glutamic acid is provided. An L-amino acid is produced by culturing a bacterium having an ability to produce an L-amino acid, which has been modified so that the activity of a non-PTS fructose-uptake carrier and the activity of fructokinase are both increased, in a medium containing fructose, and collecting the L-amino acid from the medium or cells of the bacterium.

18 Claims, 1 Drawing Sheet
Specification includes a Sequence Listing.

METHOD FOR PRODUCING L-AMINO ACID BY INCREASING FRUCTOSE UPTAKE

This application claims priority under 35 U.S.C. § 119 to Japanese Patent Application No. 2017-073937, filed Apr. 3, 2017, the entirety of which is incorporated by reference herein. Also, the Sequence Listing filed electronically herewith is hereby incorporated by reference (File name: 2018-03-27T_US-570_Seq_List; File size: 55 KB; Date recorded: Mar. 27, 2018).

BACKGROUND OF THE INVENTION

Field of the Invention

The present invention relates to a method for producing an L-amino acid such as L-glutamic acid by fermentation using a bacterium. L-amino acids are industrially useful as raw materials in seasonings and so forth.

Brief Description of the Related Art

L-amino acids are industrially produced by, for example, fermentation using microorganisms such as bacteria that are able to produce L-amino acid (Akashi et al., Amino Acid Fermentation, Japan Scientific Societies Press, p. 195-215, 1986). Examples of such microorganisms, for example, include strains isolated from nature and mutant strains thereof. Also, the ability of microorganisms to produce L-amino acids can be improved by using recombinant DNA techniques. For example, the ability of bacteria to produce L-glutamic acid can be improved by enhancing phosphoketolase activity (WO2006/016705) and/or mutating the yggB gene (WO2006/070944).

Bacterial cells can take up various saccharides from outside of the cells to utilize them as carbon sources. Examples of saccharide-uptake systems in bacteria include the phosphotransferase system (PTS), which involves phosphorylation of saccharides, and the non-PTS, which does not involve phosphorylation of saccharides. For example, *Corynebacterium glutamicum* has a FruA protein, which is a PTS fructose-uptake carrier, while it does not have any non-PTS fructose-uptake carrier. Fructose is taken up into cells via the FruA protein while being phosphorylated to fructose-1-phosphate. Meanwhile, examples of non-PTS fructose-uptake carriers include a FucP protein. The FucP protein is known as an L-fucose permease, which is a fucose-uptake carrier, while it also has fructose-uptake activity (Kornberg et al., Proc Natl Acad Sci USA. (2006) 103(51):19496-9). Fructose is taken up into cells via the FucP protein without being phosphorylated. Fructose present in cells can be, for example, phosphorylated to fructose-6-phosphate by fructokinase and then utilized (Caescu et al., J Bacteriol. (2004) 186(19):6515-25).

SUMMARY OF THE INVENTION

An object of the present invention is to develop a novel technique for improving an L-amino acid-producing ability of a bacterium, and thereby provide a method for efficiently producing an L-amino acid. The ability of a bacterium to produce an L-amino acid when using fructose as a carbon source can be improved by modifying the bacterium so that the expression of both a gene encoding a non-PTS fructose-uptake carrier and a gene encoding a fructokinase are increased.

It is an aspect of the present invention to provide a method for producing an L-amino acid, the method comprising (A) culturing a bacterium that is able to produce an L-amino acid in a medium containing fructose so that an L-amino acid is produced and accumulates in the medium and/or the bacterium; and (B) collecting the L-amino acid from the medium and/or the bacterium, wherein the bacterium has been modified so that the activity of both a non-PTS fructose-uptake carrier and a fructokinase are increased as compared with a non-modified bacterium.

It is a further aspect of the present invention to provide the method as described above, wherein the non-PTS fructose-uptake carrier is a protein encoded by a fucP gene.

It is a further aspect of the present invention to provide the method as described above, wherein the fructokinase is a protein encoded by a frk gene.

It is a further aspect of the present invention to provide the method as described above, wherein the fucP gene encodes a protein selected from the group consisting of: (a) a protein comprising the amino acid sequence of SEQ ID NO: 27 or 29; (b) a protein comprising the amino acid sequence of SEQ ID NO: 27 or 29, but which includes substitution, deletion, insertion, and/or addition of 1 to 10 amino acid residues, and wherein said protein comprises non-PTS fructose-uptake activity; and (c) a protein comprising an amino acid sequence having an identity of 90% or higher to the amino acid sequence of SEQ ID NO: 27 or 29, and wherein said protein comprises non-PTS fructose-uptake activity.

It is a further aspect of the present invention to provide the method as described above, wherein the frk gene encodes a protein selected from the group consisting of: (a) a protein comprising the amino acid sequence of SEQ ID NO: 31, 33, or 35; (b) a protein comprising the amino acid sequence of SEQ ID NO: 31, 33, or 35, but which includes substitution, deletion, insertion, and/or addition of 1 to 10 amino acid residues, and wherein said protein comprises fructokinase activity; and (c) a protein comprising an amino acid sequence having an identity of 90% or higher to the amino acid sequence of SEQ ID NO: 31, 33, or 35, and wherein said protein comprises fructokinase activity.

It is a further aspect of the present invention to provide the method as described above, wherein the activity of the non-PTS fructose-uptake carrier and the activity of fructokinase are increased by increasing the expression of a gene encoding the non-PTS fructose-uptake carrier and a gene encoding the fructokinase, respectively.

It is a further aspect of the present invention to provide the method as described above, wherein said increasing expression comprises increasing the copy number of the gene(s) and/or modifying an expression control sequence of the gene(s).

It is a further aspect of the present invention to provide the method as described above, wherein the bacterium has further been modified so that the activity of phosphoketolase is increased as compared with a non-modified bacterium.

It is a further aspect of the present invention to provide the method as described above, wherein the phosphoketolase is D-xylulose-5-phosphate phosphoketolase and/or fructose-6-phosphate phosphoketolase.

It is a further aspect of the present invention to provide the method as described above, wherein the activity of the phosphoketolase is increased by increasing the expression of a gene encoding the phosphoketolase.

It is a further aspect of the present invention to provide the method as described above, wherein the bacterium is a coryneform bacterium or a bacterium of the family Enterobacteriaceae.

It is a further aspect of the present invention to provide the method as described above, wherein the bacterium is a bacterium of the genus *Corynebacterium*.

It is a further aspect of the present invention to provide the method as described above, wherein the bacterium is *Corynebacterium glutamicum*.

It is a further aspect of the present invention to provide the method as described above, wherein the bacterium is of the genus *Pantoea* or *Escherichia*.

It is a further aspect of the present invention to provide the method as described above, wherein the bacterium is *Pantoea ananatis* or *Escherichia coli*.

It is a further aspect of the present invention to provide the method as described above, wherein the L-amino acid is an L-amino acid of the glutamate family.

It is a further aspect of the present invention to provide the method as described above, wherein the L-amino acid of the glutamate family is selected from the group consisting of L-glutamic acid, L-glutamine, L-proline, L-arginine, L-citrulline, and L-ornithine.

It is a further aspect of the present invention to provide the method as described above, wherein the L-amino acid of the glutamate family is L-glutamic acid.

It is a further aspect of the present invention to provide the method as described above, wherein the L-glutamic acid is monoammonium L-glutamate or monosodium L-glutamate.

It is a further aspect of the present invention to provide the method as described above, wherein the bacterium has further been modified so that the activity of α-ketoglutarate dehydrogenase and/or succinate dehydrogenase is/are reduced as compared with a non-modified bacterium.

It is a further aspect of the present invention to provide the method as described above, wherein the bacterium is a coryneform bacterium, and wherein the bacterium has further been modified so as to harbor a mutant yggB gene.

It is a further aspect of the present invention to provide the method as described above, wherein the mutant yggB gene comprises a mutation that results in an improved ability of the coryneform bacterium to produce the L-glutamic acid.

It is a further aspect of the present invention to provide the method as described above, wherein the mutation is selected from the group consisting of: (1) a mutation in the region coding for the amino acid residues at positions 419 to 533 of a wild-type YggB protein, (2) a mutation in the region coding for a transmembrane region of a wild-type YggB protein, and (3) a combination thereof.

It is a further aspect of the present invention to provide the method as described above, wherein the wild-type YggB protein is selected from the group consisting of: (a) a protein comprising the amino acid sequence of SEQ ID NO: 10; (b) a protein comprising the amino acid sequence of SEQ ID NO: 10, but which includes substitution, deletion, insertion, and/or addition of 1 to 10 amino acid residues, and wherein said protein, when overexpressed in the coryneform bacterium, provides an improved ability of the coryneform bacterium to produce L-glutamic acid; and (c) a protein comprising an amino acid sequence having an identity of 90% or higher to the amino acid sequence of SEQ ID NO: 10, and wherein said protein, when overexpressed in the coryneform bacterium, provides an improved of the coryneform bacterium to produce the L-glutamic acid.

It is a further aspect of the present invention to provide the method as described above, wherein the medium further contains a carbon source other than fructose.

It is a further aspect of the present invention to provide the method as described above, wherein the carbon source is glucose.

According to the present invention, an L-amino acid-producing ability of a bacterium when using fructose as a carbon source can be improved, and an L-amino acid can be efficiently produced.

DETAILED DESCRIPTION OF EXEMPLARY EMBODIMENTS

Figure 1:
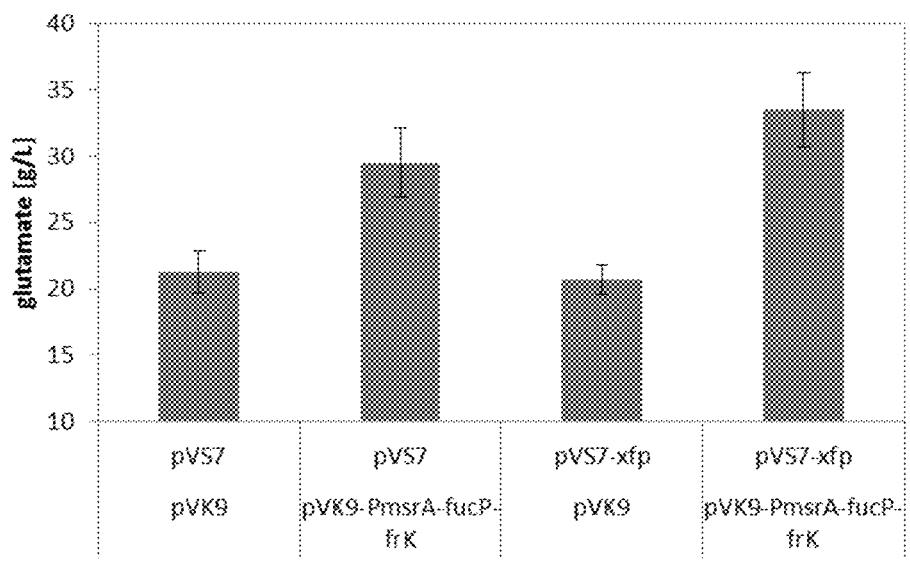
FIG. 1 shows a diagram showing results of glutamic acid production culture in a medium containing fructose as a carbon source using a *C. glutamicum* strain having increased expression of the fucP-frk genes.

The method as described herein is a method for producing an L-amino acid including the steps of culturing a bacterium that is able to produce an L-amino acid in a medium containing fructose so that the L-amino acid is produced and accumulates in the medium and/or cells of the bacterium, and collecting the L-amino acid from the medium and/or cells of the bacterium, wherein the bacterium has been modified so that the activity of both a non-PTS fructose-uptake carrier and a fructokinase are increased.

<1> Bacterium

The bacterium has an ability to produce an L-amino acid and has been modified so that the activity of both a non-PTS fructose-uptake carrier and a fructokinase are increased.

<1-1> Bacterium Able to Produce an L-Amino Acid

A bacterium able to produce an L-amino acid can refer to a bacterium that when cultured in a medium containing fructose, for example, is able to generate or produce an L-amino acid so that it accumulates in a medium and/or cells of the bacterium to such a degree that the L-amino acid can be collected. The bacterium may be able to generate or produce an objective L-amino acid so that it accumulates in a medium and/or cells of the bacterium in an amount larger than that which is obtained with a non-modified bacterium. The non-modified bacterium can refer to a control bacterial strain that has not been modified so that the activity of either a non-PTS fructose-uptake carrier or the activity of fructokinase is increased. That is, examples of the non-modified bacterial strain can include a wild-type strain and parental strain. The bacterium may be able to generate or produce an L-amino acid so that is accumulates in a medium in an amount of 0.5 g/L or more, or 1.0 g/L or more.

Examples of the L-amino acid can include basic amino acids such as L-lysine, L-ornithine, L-arginine, L-histidine, and L-citrulline; aliphatic amino acids such as L-isoleucine, L-alanine, L-valine, L-leucine, and glycine; amino acids which are hydroxy-monoaminocarboxylic acids such as L-threonine and L-serine; cyclic amino acids such as L-proline; aromatic amino acids such as L-phenylalanine, L-tyrosine, and L-tryptophan; sulfur-containing amino acids such as L-cysteine, L-cystine, and L-methionine; acidic amino acids such as L-glutamic acid and L-aspartic acid; and amino acids having an amide group in the side chain such as L-glutamine and L-asparagine. Particular examples of the L-amino acid can include L-amino acid of glutamate family. The phrase "L-amino acid of the glutamate family" collectively can refer to L-glutamic acid and L-amino acids that are biosynthesized via L-glutamic acid as an intermediate. Examples of the L-amino acids that are biosynthesized via L-glutamic acid as an intermediate can include L-glutamine, L-proline, L-arginine, L-citrulline, and L-ornithine. The bacterium may be to produce a single kind of L-amino acid, or two or more kinds of L-amino acids.

The term "amino acid" can refer to an L-amino acid, unless otherwise stated. The term "L-amino acid" can refer to an L-amino acid in a free form, a salt thereof, or a mixture thereof, unless otherwise stated. Examples of salt are described herein.

Examples of the bacterium as described herein can include bacteria of the family Enterobacteriaceae and coryneform bacteria.

Examples of bacteria of the family Enterobacteriaceae can include bacteria of the genus *Escherichia*, *Enterobacter*, *Pantoea*, *Klebsiella*, *Serratia*, *Envinia*, *Photorhabdus*, *Providencia*, *Salmonella*, *Morganella*, or the like. Specifically, bacteria classified into the family Enterobacteriaceae according to the taxonomy used in the NCBI (National Center for Biotechnology Information) database (ncbi.nlm.nih.gov/Taxonomy/Browser/wwwtax.cgi?id=91347) can be used.

The *Escherichia* bacteria are not particularly limited, and examples thereof can include those classified into the genus *Escherichia* according to the taxonomy known to those skilled in the field of microbiology. Examples of the *Escherichia* bacteria can include, for example, those described in the work of Neidhardt et al. (Backmann B. J., 1996, Derivations and Genotypes of some mutant derivatives of *Escherichia coli* K-12, pp. 2460-2488, Table 1, In F. D. Neidhardt (ed.), *Escherichia coli* and *Salmonella* Cellular and Molecular Biology/Second Edition, American Society for Microbiology Press, Washington, D.C.). Examples of the *Escherichia* bacteria can include, for example, *Escherichia coli*. Specific examples of *Escherichia coli* can include, for example, *Escherichia coli* K-12 strains such as W3110 strain (ATCC 27325) and MG1655 strain (ATCC 47076); *Escherichia coli* K5 strain (ATCC 23506); *Escherichia coli* B strains such as BL21 (DE3) strain; and derivative strains thereof.

The *Enterobacter* bacteria are not particularly limited, and examples can include those classified into the genus *Enterobacter* according to the taxonomy known to those skilled in the field of microbiology. Examples the *Enterobacter* bacterium can include, for example, *Enterobacter agglomerans* and *Enterobacter aerogenes*. Specific examples of *Enterobacter agglomerans* can include, for example, the *Enterobacter agglomerans* ATCC 12287 strain. Specific examples of *Enterobacter aerogenes* can include, for example, the *Enterobacter aerogenes* ATCC 13048 strain, NBRC 12010 strain (Biotechnol. Bioeng., 2007, Mar. 27; 98(2):340-348), and AJ110637 strain (FERM BP-10955). Examples the *Enterobacter* bacteria also can include, for example, the strains described in European Patent Application Laid-open (EP-A) No. 0952221. In addition, *Enterobacter agglomerans* also can include some strains classified as *Pantoea agglomerans*.

The *Pantoea* bacteria are not particularly limited, and examples can include those classified into the genus *Pantoea* according to the taxonomy known to those skilled in the field of microbiology. Examples the *Pantoea* bacteria can include, for example, *Pantoea ananatis*, *Pantoea stewartii*, *Pantoea agglomerans*, and *Pantoea citrea*. Specific examples of *Pantoea ananatis* can include, for example, the *Pantoea ananatis* LMG20103 strain, AJ13355 strain (FERM BP-6614), AJ13356 strain (FERM BP-6615), AJ13601 strain (FERM BP-7207), SC17 strain (FERM BP-11091), SC17(0) strain (VKPM B-9246), and SC17sucA strain (FERM BP-8646). Some of *Enterobacter* bacteria and *Envinia* bacteria were reclassified into the genus *Pantoea* (Int. J. Syst. Bacteriol., 39, 337-345 (1989); Int. J. Syst. Bacteriol., 43, 162-173 (1993)). For example, some strains of *Enterobacter agglomerans* were recently reclassified into *Pantoea agglomerans*, *Pantoea ananatis*, *Pantoea stewartii*, or the like on the basis of nucleotide sequence analysis of 16S rRNA etc. (Int. J. Syst. Bacteriol., 39, 337-345 (1989)). The *Pantoea* bacteria can include those reclassified into the genus *Pantoea* as described above.

Examples of the Envinia bacteria can include Envinia *amylovora* and Envinia *carotovora*. Examples of the *Klebsiella* bacteria can include *Klebsiella planticola*.

Examples of the coryneform bacteria can include bacteria belonging to the genus *Corynebacterium*, *Brevibacterium*, *Microbacterium*, or the like.

Specific examples of the coryneform bacteria can include the following species:
*Corynebacterium acetoacidophilum*
*Corynebacterium acetoglutamicum*
*Corynebacterium alkanolyticum*
*Corynebacterium callunae*
*Corynebacterium crenatum*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*
*Corynebacterium ammoniagenes* (*Corynebacterium stationis*)
*Brevibacterium album*
*Brevibacterium cerinum*
*Microbacterium ammoniaphilum*

Specific examples of the coryneform bacteria can include the following strains:
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium crenatum* AS1.542
*Corynebacterium glutamicum* ATCC 13020, ATCC 13032, ATCC 13060, ATCC 13869, FERM BP-734
*Corynebacterium lilium* ATCC 15990
*Corynebacterium melassecola* ATCC 17965
*Corynebacterium efficiens* (*Corynebacterium thermoaminogenes*) AJ12340 (FERM BP-1539)
*Corynebacterium herculis* ATCC 13868
*Brevibacterium divaricatum* (*Corynebacterium glutamicum*) ATCC 14020
*Brevibacterium flavum* (*Corynebacterium glutamicum*) ATCC 13826, ATCC 14067, AJ12418 (FERM BP-2205)
*Brevibacterium immariophilum* ATCC 14068
*Brevibacterium lactofermentum* (*Corynebacterium glutamicum*) ATCC 13869
*Brevibacterium roseum* ATCC 13825
*Brevibacterium saccharolyticum* ATCC 14066
*Brevibacterium thiogenitalis* ATCC 19240

*Corynebacterium ammoniagenes* (*Corynebacterium stationis*) ATCC 6871, ATCC 6872
*Brevibacterium album* ATCC 15111
*Brevibacterium cerinum* ATCC 15112
*Microbacterium ammoniaphilum* ATCC 15354

The *Corynebacterium* bacteria can include bacteria that had previously been classified into the genus *Brevibacterium*, but are currently united into the genus *Corynebacterium* (Int. J. Syst. Bacteriol., 41, 255 (1991)). Moreover, *Corynebacterium stationis* can include bacteria that had previously been classified as *Corynebacterium ammoniagenes*, but are now re-classified into *Corynebacterium stationis* on the basis of nucleotide sequence analysis of 16S rRNA etc. (Int. J. Syst. Evol. Microbiol., 60, 874-879 (2010)).

These strains are available from, for example, the American Type Culture Collection (Address: P.O. Box 1549, Manassas, Va. 20108, United States of America). That is, registration numbers are given to the respective strains, and the strains can be ordered by using these registration numbers (refer to atcc.org/). The registration numbers of the strains are listed in the catalogue of the American Type Culture Collection. These strains can also be obtained from, for example, the depositories at which the strains were deposited.

The bacterium may inherently be able to produce an L-amino acid, or may be modified so that it is able to produce an L-amino acid. The bacterium can be obtained by imparting the ability to produce an L-amino acid to such a bacterium as described above, or by enhancing the ability to produce an L-amino acid of such a bacterium as described above.

To impart or enhance the ability to produce an L-amino acid, methods conventionally employed in the breeding of amino acid-producing strains of coryneform bacteria, *Escherichia* bacteria, and so forth (refer to "Amino Acid Fermentation", Gakkai Shuppan Center (Ltd.), 1st Edition, published May 30, 1986, pp. 77-100) can be used. Examples of such methods can include, for example, acquiring an auxotrophic mutant strain, acquiring an L-amino acid analogue-resistant strain, acquiring a metabolic regulation mutant strain, and constructing a recombinant strain in which the activity of an L-amino acid biosynthetic enzyme is enhanced. In the breeding of bacteria able to produce an L-amino acid, one of the above-described properties, such as auxotrophy, analogue resistance, and metabolic regulation mutation, may be imparted alone, or two or three or more of such properties may be imparted in combination. Also, in the breeding of bacteria able to produce an L-amino acid, the activity of one of L-amino acid biosynthetic enzymes may be enhanced alone, or the activities of two or three or more of such enzymes may be enhanced in combination. Furthermore, imparting property(s) such as auxotrophy, analogue resistance, and metabolic regulation mutation can be combined with enhancing the activity(s) of biosynthetic enzyme(s).

An auxotrophic mutant strain, analogue-resistant strain, or metabolic regulation mutant strain able to produce an L-amino acid can be obtained by subjecting a parental strain or wild-type strain to a known mutagenesis treatment, and then selecting a strain exhibiting autotrophy, analogue resistance, or a metabolic regulation mutation, and able to produce an L-amino acid from the resulting mutant strains. Examples of the known mutagenesis treatments can include irradiation of X-ray or ultraviolet and a treatment with a mutation agent such as N-methyl-N'-nitro-N-nitrosoguanidine (MNNG), ethyl methanesulfonate (EMS), and methyl methanesulfonate (MMS).

An ability to produce an L-amino acid can also be imparted or enhanced by enhancing the activity of an enzyme involved in biosynthesis of the objective L-amino acid. An enzyme activity can be enhanced by, for example, modifying a bacterium so that the expression of a gene encoding the enzyme is enhanced. Methods for enhancing gene expression are described in WO00/18935, EP1010755A, and so forth. The detailed procedures for enhancing enzyme activity are described herein.

Furthermore, the ability to produce an L-amino acid can also be imparted or enhanced by reducing the activity of an enzyme that catalyzes a reaction branching away from the biosynthetic pathway of the objective L-amino acid so that a compound other than the objective L-amino acid is produced. Such enzymes can include those involved in decomposition of the objective amino acid. The method for reducing enzyme activity is described herein.

Hereinafter, bacteria able to produce L-amino acids and methods for imparting or enhancing such an ability will be specifically exemplified. All of the properties of the bacteria and modifications for imparting or enhancing the ability to produce L-amino acids may be used independently or in any appropriate combination.

<L-Glutamic Acid-Producing Bacteria>

Examples of methods for imparting, increasing, or enhancing an ability to produce L-glutamic acid can include, for example, a method of modifying a bacterium so that the bacterium has an increased activity or activities of one or more kinds of the L-glutamic acid biosynthesis enzymes. Examples of such enzymes can include, but are not particularly limited to, glutamate dehydrogenase (gdhA), glutamine synthetase (glnA), glutamate synthase (gltBD), isocitrate dehydrogenase (icdA), aconitate hydratase (acnA, acnB), citrate synthase (gltA), methylcitrate synthase (prpC), pyruvate carboxylase (pyc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), glucose phosphate isomerase (pgi), 6-phosphogluconate dehydratase (edd), 2-keto-3-deoxy-6-phosphogluconate aldolase (eda), and transhydrogenase. Shown in the parentheses after each enzyme is the name of the corresponding gene encoding the enzyme (the same shall apply for other proteins/enzymes hereinafter). Increasing the activity or activities of one or more of, for example, glutamate dehydrogenase, citrate synthase, phosphoenol pyruvate carboxylase, and methylcitrate synthase are particular examples.

Examples of strains of the family Enterobacteriaceae and modified so that the expression of the citrate synthase gene, phosphoenolpyruvate carboxylase gene, and/or glutamate dehydrogenase gene are increased can include those disclosed in EP1078989A, EP955368A, and EP952221A. Furthermore, examples of strains belonging to the family Enterobacteriaceae and modified so that the expression of a gene of the Entner-Doudoroff pathway (edd, eda) is increased can include those disclosed in EP1352966B. Examples of coryneform bacteria modified so that the expression of the glutamate synthetase gene (gltBD) is increased can include those disclosed in WO99/07853.

Examples of methods for imparting, increasing, or enhancing an ability to produce L-glutamic acid also can include, for example, a method of modifying a bacterium so that the bacterium has a reduced activity or activities of one or more kinds of enzymes that catalyze a reaction branching away from the biosynthesis pathway of L-glutamic acid to generate a compound other than L-glutamic acid. Examples of such enzymes can include, but are not particularly limited to, isocitrate lyase (aceA), α-ketoglutarate dehydrogenase (sucA, odhA), acetolactate synthase (ilvI), formate acetyltransferase (pfl), lactate dehydrogenase (ldh), alcohol dehydrogenase (adh), glutamate decarboxylase (gadAB), and succinate dehydrogenase (sdhABCD). Reducing or deleting, for example, the α-ketoglutarate dehydrogenase activity is a particular example.

*Escherichia* bacteria with a reduced or deficient α-ketoglutarate dehydrogenase activity, and methods for obtaining such bacteria are described in U.S. Pat. Nos. 5,378,616 and 5,573,945. Furthermore, methods for reducing or deleting the α-ketoglutarate dehydrogenase activity of Enterobacteriaceae bacteria such as *Pantoea* bacteria, *Enterobacter* bacteria, *Klebsiella* bacteria, and Envinia bacteria are disclosed in U.S. Pat. Nos. 6,197,559, 6,682,912, 6,331,419, and 8,129,151, and WO2008/075483. Specific examples of *Escherichia* bacteria having a reduced or deficient α-ketoglutarate dehydrogenase activity can include the following strains:

*E. coli* W3110sucA::Km$^r$
*E. coli* AJ12624 (FERM BP-3853)
*E. coli* AJ12628 (FERM BP-3854)
*E. coli* AJ12949 (FERM BP-4881)

The *E. coli* W3110sucA::Km$^r$ strain was obtained by disrupting the sucA gene encoding α-ketoglutarate dehydrogenase of *E. coli* W3110. This strain is completely deficient in α-ketoglutarate dehydrogenase activity.

Coryneform bacteria in which the α-ketoglutarate dehydrogenase activity is reduced or eliminated, and methods for obtaining such bacteria are disclosed in WO2008/075483. Specific examples of coryneform bacteria in which the α-ketoglutarate dehydrogenase activity is reduced or eliminated can include, for example, the following strains:

*Corynebacterium glutamicum* (*Brevibacterium lactofermentum*) L30-2 strain (Japanese Patent Laid-open (Kokai) No. 2006-340603)
*Corynebacterium glutamicum* (*Brevibacterium lactofermentum*) AS strain (WO95/34672)
*Corynebacterium glutamicum* (*Brevibacterium lactofermentum*) AJ12821 (FERM BP-4172, French Patent No. 9401748)
*Corynebacterium glutamicum* (*Brevibacterium flavum*) AJ12822 (FERM BP-4173, French Patent No. 9401748)
*Corynebacterium glutamicum* AJ12823 (FERM BP-4174, French Patent No. 9401748)

Examples of L-glutamic acid-producing bacteria and parental strains that can be used to derive them also can include *Pantoea* bacteria, such as the *Pantoea ananatis* AJ13355 strain (FERM BP-6614), *Pantoea ananatis* SC17 strain (FERM BP-11091), and *Pantoea ananatis* SC17(0) strain (VKPM B-9246). The AJ13355 strain was isolated from soil in Iwata-shi, Shizuoka-ken, Japan as a strain that can proliferate in a low pH medium containing L-glutamic acid and a carbon source. The SC17 strain was selected as a low phlegm-producing mutant strain from the AJ13355 strain (U.S. Pat. No. 6,596,517). The SC17 strain was deposited at the independent administrative agency, National Institute of Advanced Industrial Science and Technology, International Patent Organism Depositary (currently independent administrative agency, National Institute of Technology and Evaluation, International Patent Organism Depositary, #120, 2-5-8 Kazusakamatari, Kisarazu-shi, Chiba-ken, 292-0818, Japan) on Feb. 4, 2009, and assigned an accession number of FERM BP-11091. The AJ13355 strain was deposited at the National Institute of Bioscience and Human Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 19, 1998 and assigned an accession number of FERM P-16644. Then, the deposit was converted to an international deposit under the provisions of Budapest Treaty on Jan. 11, 1999, and assigned an accession number of FERM BP-6614.

Furthermore, examples of L-glutamic acid-producing bacteria and parental strains that can be used to derive them also include *Pantoea* bacteria having a reduced or deficient α-ketoglutarate dehydrogenase activity. Examples of such strains can include the AJ13356 strain (U.S. Pat. No. 6,331,419), which is an α-ketoglutarate dehydrogenase E1 subunit (sucA) gene-deficient strain of the AJ13355 strain, and the SC17sucA strain (U.S. Pat. No. 6,596,517), which is a sucA gene-deficient strain of the SC17 strain. The AJ13356 strain was deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 19, 1998, and assigned an accession number of FERM P-16645. Then, the deposit was converted into an international deposit under the provisions of the Budapest Treaty on Jan. 11, 1999, and assigned an accession number of FERM BP-6616. The SC17sucA strain was assigned a private number of AJ417, and deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Feb. 26, 2004, under an accession number of FERM BP-8646.

The AJ13355 strain was identified as *Enterobacter agglomerans* when it was isolated, but it was recently reclassified as *Pantoea ananatis* on the basis of nucleotide sequencing of 16S rRNA and so forth. Therefore, although the AJ13355 and AJ13356 strains are deposited at the aforementioned depository as *Enterobacter agglomerans*, they are referred to as *Pantoea ananatis* in this specification.

Examples of L-glutamic acid-producing bacteria and parental strains that can be used to derive them also can include auxotrophic mutant strains. Specific examples of auxotrophic mutant strains can include, for example, *E. coli* VL334thrC$^+$ (VKPM B-8961, EP1172433). *E. coli* VL334 (VKPM B-1641) is an L-isoleucine and L-threonine auxotrophic strain having mutations in the thrC and ilvA genes (U.S. Pat. No. 4,278,765). *E. coli* VL334thrC$^+$ is auxotrophic for L-isoleucine and able to produce L-glutamic acid obtained by introducing a wild-type allele of the thrC gene into the VL334 strain. The wild-type allele of the thrC gene was introduced by the general transduction method using a bacteriophage P1 grown on the wild-type *E. coli* K-12 strain (VKPM B-7) cells.

Examples of L-glutamic acid-producing bacteria and parental strains that can be used to derive them also can include strains having resistance to an aspartic acid analogue. Such strains can also be deficient in α-ketoglutarate dehydrogenase activity. Specific examples of strains having resistance to an aspartic acid analogue and deficient in the α-ketoglutarate dehydrogenase activity can include, for example, *E. coli* AJ13199 (FERM BP-5807, U.S. Pat. No. 5,908,768), *E. coli* FFRM P-12379, which additionally has a decreased ability to decompose L-glutamic acid (U.S. Pat. No. 5,393,671), and *E. coli* AJ13138 (FERM BP-5565, U.S. Pat. No. 6,110,714).

Examples of methods for imparting, increasing, or enhancing an ability to produce L-glutamic acid also can include, for example, a method of increasing or enhancing the expression of an L-glutamic acid secretion gene, such as yhfK gene (WO2005/085419) or ybjL gene (WO2008/133161).

Furthermore, examples of methods for imparting, increasing, or enhancing an ability to produce L-glutamic acid to or in coryneform bacteria also can include methods of imparting resistance to an organic acid analogue, respiratory inhibitor, or the like, and methods of imparting sensitivity to a cell wall synthesis inhibitor. Specific examples of such methods can include, for example, the method of imparting monofluoroacetic acid resistance (Japanese Patent Laid-open (Kokai) No. 50-113209), the method of imparting adenine resistance or thymine resistance (Japanese Patent Laid-open (Kokai) No. 57-065198), the method of attenuating urease (Japanese Patent Laid-open (Kokai) No. 52-038088), the method of imparting malonic acid resistance (Japanese Patent Laid-open (Kokai) No. 52-038088), the method of imparting resistance to benzopyrones or naphthoquinones (Japanese Patent Laid-open (Kokai) No. 56-1889), the method of imparting HOQNO resistance (Japanese Patent Laid-open (Kokai) No. 56-140895), the method of imparting α-ketomalonic acid resistance (Japanese Patent Laid-open (Kokai) No. 57-2689), the method of imparting guanidine resistance (Japanese Patent Laid-open (Kokai) No. 56-35981), the method of imparting sensitivity to penicillin (Japanese Patent Laid-open (Kokai) No. 4-88994), and so forth.

Specific examples of such resistant or sensitive bacteria can include the following strains:

*Corynebacterium glutamicum* (*Brevibacterium flavum*) AJ3949 (FERM BP-2632, Japanese Patent Laid-open (Kokai) No. 50-113209)

*Corynebacterium glutamicum* AJ11628 (FERM P-5736, Japanese Patent Laid-open (Kokai) No. 57-065198)

*Corynebacterium glutamicum* (*Brevibacterium flavum*) AJ11355 (FERM P-5007, Japanese Patent Laid-open (Kokai) No. 56-1889)

*Corynebacterium glutamicum* AJ11368 (FERM P-5020, Japanese Patent Laid-open (Kokai) No. 56-1889)

*Corynebacterium glutamicum* (*Brevibacterium flavum*) AJ11217 (FERM P-4318, Japanese Patent Laid-open (Kokai) No. 57-2869)

*Corynebacterium glutamicum* AJ11218 (FERM P-4319, Japanese Patent Laid-open (Kokai) No. 57-2869)

*Corynebacterium glutamicum* (*Brevibacterium flavum*) AJ11564 (FERM BP-5472, Japanese Patent Laid-open (Kokai) No. 56-140895)

*Corynebacterium glutamicum* (*Brevibacterium flavum*) AJ11439 (FERM BP-5136, Japanese Patent Laid-open (Kokai) No. 56-35981)

*Corynebacterium glutamicum* H7684 (FERM BP-3004, Japanese Patent Laid-open (Kokai) No. 04-88994)

*Corynebacterium glutamicum* (*Brevibacterium lactofermentum*) AJ11426 (FERM P-5123, Japanese Patent Laid-open (Kokai) No. 56-048890)

*Corynebacterium glutamicum* AJ11440 (FERM P-5137, Japanese Patent Laid-open (Kokai) No. 56-048890)

*Corynebacterium glutamicum* (*Brevibacterium lactofermentum*) AJ11796 (FERM P-6402, Japanese Patent Laid-open (Kokai) No. 58-158192)

Furthermore, examples of methods for imparting, increasing, or enhancing an ability to produce L-glutamic acid to or in coryneform bacteria also can include a method of enhancing the expression of the yggB gene and a method of introducing a mutant yggB gene having a mutation in the coding region (WO2006/070944). That is, the bacterium can be modified so that the expression of yggB gene is increased, or can be modified so as to harbor (have) a mutant yggB gene.

The yggB gene encodes a mechanosensitive channel. Examples of the yggB gene can include yggB genes of coryneform bacteria. Specific examples of the yggB genes of coryneform bacteria can include, for example, yggB genes of *Corynebacterium glutamicum* ATCC13869, *Corynebacterium glutamicum* ATCC13032, *Corynebacterium glutamicum* ATCC14967, and *Corynebacterium melassecola* ATCC17965 (WO2006/070944). The yggB gene of *Corynebacterium glutamicum* ATCC 13032 corresponds to the sequence complementary to the sequence of the nucleotide numbers 1,336,091 to 1,337,692 in the genome sequence registered as Genbank Accession No. NC 003450 in the NCBI database, and is also called NCgl1221. The YggB protein encoded by the yggB gene of *Corynebacterium glutamicum* ATCC 13032 is registered as GenBank accession No. NP_600492. In addition, the nucleotide sequence of the yggB gene of *Corynebacterium glutamicum* 2256 (ATCC 13869) and the amino acid sequence of the YggB protein encoded by the gene are shown in SEQ ID NOS: 9 and 10, respectively.

A yggB gene having the "specific mutation" described herein can also be referred to as a "mutant yggB gene", and a protein encoded thereby can also be referred to as a "mutant YggB protein". Furthermore, a yggB gene not having the "specific mutation" described herein can also be referred to as a "wild-type yggB gene", and a protein encoded thereby can also be referred to as a "wild-type YggB protein". Incidentally, as for the YggB protein, the change in the amino acid sequence caused by the "specific mutation" in the yggB gene can also be referred to as a "specific mutation". The term "wild-type" distinguishes the "wild-type" yggB gene or YggB protein from the "mutant" yggB gene or YggB protein, and the "wild-type" yggB gene or YggB protein is not limited to those obtained as natural substances, so long as it does not have the "specific mutation". Examples of the wild-type YggB protein can include the YggB proteins exemplified above, such as the YggB protein having the amino acid sequence of SEQ ID NO: 10. Examples of the wild-type YggB protein also can include conservative variants, that is, variants in which the original function thereof is maintained, of the YggB proteins exemplified above, provided that the conservative variants do not have the "specific mutation". The "original function" regarding the YggB protein may be, for example, a function as a mechanosensitive channel or a property that an increased expression thereof in a coryneform bacterium provides an improved L-glutamic acid-producing ability of the coryneform bacterium.

The "specific mutation" is not particularly limited, so long as it changes the amino acid sequence of the YggB protein such as those described above to thereby improve an ability of a coryneform bacterium to produce L-glutamic acid. Examples of the "specific mutation" can include a mutation on the C-terminus side and a mutation in a transmembrane region. The "specific mutation" may also be a combination of these.

(1) Mutation on C-Terminus Side

The mutation on the C-terminus side is a mutation introduced into the region of the wild-type yggB gene coding for the amino acid residues of the positions 419 to 533 of the wild-type YggB protein. The mutation on the C-terminus side may be introduced at one or more sites in the region. The type of change of the amino acid sequence induced by the mutation on the C-terminus side is not particularly limited. The mutation on the C-terminus side may be a mutation that results in an amino acid substitution (missense mutation), insertion of amino acid residue, deletion of amino acid residue, introduction of stop codon (nonsense mutation), frame shift mutation, or a combination of these. The mutation on the C-terminus side can be, for example, a mutation that results in a nucleotide sequence such as an insertion sequence, henceforth also referred to as "IS", or transposon.

(1-1) Insertion of Nucleotide Sequence

Examples of the mutation on the C-terminus side can include, for example, a mutation that results in insertion of a nucleotide sequence at the site coding for the valine residue at the position 419 of the wild-type YggB protein (2A-1 type mutation). The 2A-1 type mutation may be, for example, a mutation that results in deletion or substitution of a part or all of the amino acid residues at the positions 419 to 533 of the wild-type YggB protein. Specific examples of the mutant yggB gene having the 2A-1 type mutation can include, for example, the yggB gene including IS inserted into the next of "G" at the position 1255 in SEQ ID NO: 9, and thereby coding for a mutant YggB protein having the full length of 423 amino residues, which is shorter than that of the original wild-type YggB protein (SEQ ID NO: 10). The nucleotide sequence of this mutant yggB gene (V419::IS) and the amino acid sequence of the mutant YggB protein encoded by the gene are shown in SEQ ID NOS: 11 and 12, respectively. In the SEQ ID NO: 11, the positions 1 to 1269 correspond to CDS for this mutant YggB protein (V419::IS). Specific examples of the L-glutamic acid-producing bacterium having the mutant yggB gene (V419::IS) can include, for example, the *C. glutamicum* 2256ΔsucAΔldhA yggB* strain (WO2014/185430).

(1-2) Substitution for Proline Residues

Examples of the mutation on the C-terminus side also can include, for example, a mutation that replaces a proline residue present at positions 419 to 533 of the wild-type YggB protein with another amino acid residue. Examples of such a proline residue can include the proline residues at positions 424, 437, 453, 457, 462, 469, 484, 489, 497, 515, 529, and 533 of the wild-type YggB protein. It is a particular example to replace the proline residue(s) of the position(s) 424 and/or 437 with other amino acid residue(s). The "other amino acid" is not particularly limited so long as it is a naturally occurring amino acid other than proline. Examples of the "other amino acid" can include Lys, Glu, Thr, Val, Leu, Ile, Ser, Asp, Asn, Gln, Arg, Cys, Met, Phe, Trp, Tyr, Gly, Ala, and His. For example, the proline residue at the position 424 may be replaced with a hydrophobic amino acid residue (Ala, Gly, Val, Leu, or Ile), or a branched chain amino acid residue (Leu, Val, or Ile). Furthermore, for example, the proline residue at position 437 may be replaced with an amino acid residue having a hydroxyl group in the side chain (Thr, Ser, or Tyr), such as a Ser residue.

(2) Mutation in Transmembrane Region

The YggB protein is estimated to have five transmembrane regions. The transmembrane regions correspond to the amino acid residues at positions 1 to 23 (first transmembrane region), positions 25 to 47 (second transmembrane region), positions 62 to 84 (third transmembrane region), positions 86 to 108 (fourth transmembrane region), and positions 110 to 132 (fifth transmembrane region) of the wild-type YggB protein. The mutation in a transmembrane region is a mutation in the regions coding for these transmembrane regions of the wild-type yggB gene. The mutation in a transmembrane region may be introduced into one or more sites in the regions. The mutation in a transmembrane region can be a mutation that induces substitution, deletion, addition, insertion, or inversion of one or several amino acid residues, but does not include any frame shift mutation or nonsense mutation. The number meant by the term "one or several" can be 1 to 20, 1 to 10, 1 to 5, or 1 to 3. Examples of the mutation in a transmembrane region can include a mutation that results in insertion of one or several amino acid residues, such as Cys-Ser-Leu, between the leucine residue at position 14 and the tryptophan residue at position 15; a mutation that replaces the alanine residue at position 100 with another amino acid residue, such as an amino acid residue having a hydroxyl group in the side chain, for example, Thr, Ser, or Tyr, such as a Thr residue; a mutation that replaces the alanine residue at position 111 with another amino acid residue such as a Val residue or a residue of an amino acid having hydroxyl group in the side chain, for example, Thr, Ser, or Tyr, such as a Val or Thr residue; in the wild-type YggB protein.

The phrase "amino acid residue at position X of the wild-type YggB protein" can mean the amino acid residue corresponding to that of position X in SEQ ID NO: 10, unless otherwise stated. The "position X" in an amino acid sequence is the X-th position counted from the N-terminus of the amino acid sequence, and the amino acid residue of the N-terminus is the amino acid residue of the position 1. That is, the aforementioned positions of amino acid residues indicate relative positions, and the absolute positions thereof may shift due to deletion, insertion, addition, or the like of an amino acid residue or residues. For example, the "amino acid residue at the position 419 of the wild-type YggB protein" can mean the amino acid residue corresponding to that of the position 419 in SEQ ID NO: 10, and when one amino acid residue is deleted at a position on the N-terminus side of the position 419, the 418th amino acid residue from the N-terminus is "the amino acid residue at the position 419 of the wild-type YggB protein". Furthermore, when one amino acid residue is inserted at a position on the N-terminus side of the position 419, the 420th amino acid residue from the N-terminus is "the amino acid residue at position 419 of the wild-type YggB protein". Specifically, for example, amino acid residues of positions 419 to 529 of the YggB protein of *Corynebacterium glutamicum* ATCC14967 correspond to amino acid residues of positions 419 to 533 of the wild-type YggB protein.

The amino acid residue that is "the amino acid residue corresponding to that of the position X in SEQ ID NO: 10" in the amino acid sequence of an arbitrary YggB protein can be determined by aligning the amino acid sequence of the arbitrary YggB protein and the amino acid sequence of SEQ ID NO: 10. The alignment can be performed by, for example, using known gene analysis software. Specific examples of such software can include DNASIS produced by Hitachi Solutions, GENETYX produced by Genetyx, and so forth (Elizabeth C. Tyler et al., Computers and Biomedical Research, 24 (1) 72-96, 1991; Barton G J et al., Journal of Molecular Biology, 198 (2), 327-37, 1987).

A mutant yggB gene can be obtained by modifying a wild-type yggB gene so as to have the aforementioned "specific mutation". The modification of DNA can be performed by a known method. For example, an objective mutation can be introduced into an objective site of DNA by the site-specific mutation method. Specific examples of the site-specific mutation method can include, for example, a method using PCR (Higuchi, R., 61, in PCR Technology, Erlich, H. A. Eds., Stockton Press, 1989; Carter P., Meth. In Enzymol., 154, 382, 1987), and a method using a phage (Kramer, W. and Frits, H. J., Meth. in Enzymol., 154, 350, 1987; Kunkel, T. A. et al., Meth. in Enzymol., 154, 367, 1987). Furthermore, a mutant yggB gene can also be obtained by chemical synthesis.

The bacterium can be modified to have a mutant yggB gene by introducing the mutant yggB gene into the bacterium, or by introducing a mutation into the yggB gene of the bacterium through natural mutation or a treatment with a mutagen.

The methods for imparting, increasing, or enhancing an ability to produce L-glutamic acid can also be effective for imparting, increasing, or enhancing an ability to produce L-amino acids that are biosynthesized via L-glutamic acid as an intermediate, such as L-glutamine, L-proline, L-arginine, L-citrulline, and L-ornithine. Hence, a bacterium having an ability to produce any of these L-amino acids that are biosynthesized via L-glutamic acid may have, as required, such a property possessed by an L-glutamic acid-producing bacterium as mentioned above. For example, a bacterium having an ability to produce any of these L-amino acids that are biosynthesized via L-glutamic acid may have been modified so that the activity of α-ketoglutarate dehydrogenase and/or succinate dehydrogenase is reduced.

<L-Glutamine-Producing Bacteria>

Examples of the method for imparting, increasing, or enhancing an ability to produce L-glutamine can include, for example, a method of modifying a bacterium so that the activity or activities of one or more kinds of L-glutamine biosynthesis enzymes are enhanced. Examples of such enzymes can include, but are not particularly limited to, glutamate dehydrogenase (gdhA) and glutamine synthetase (glnA). The glutamine synthetase activity can also be enhanced by disruption of the glutamine adenylyltransferase gene (glnE) or disruption of the PII control protein gene (glnB) (EP1229121).

Examples of the method for imparting, increasing, or enhancing an ability to produce L-glutamine also can include, for example, a method of modifying a bacterium so that the activity or activities of one or more kinds of enzymes that catalyze a reaction branching away from the biosynthesis pathway of L-glutamine to generate a compound other than L-glutamine are reduced. Examples of such enzymes can include, but are not particularly limited to, glutaminase.

Specific examples of bacteria able to produce L-glutamine and parent strains that can be used to derive them can include, for example, coryneform bacteria in which the activity or activities of glutamate dehydrogenase (gdhA) and/or glutamine synthetase (glnA) (EP1229121, EP1424398) are enhanced, and coryneform bacteria in which the glutaminase activity (Japanese Patent Laid-open (Kokai) No. 2004-187684) is reduced. Examples of bacteria able to produce L-glutamine and parental strains that can be used to derive them can include a strain belonging to the genus *Escherichia* and having a mutant glutamine synthetase in which the tyrosine residue at position 397 of glutamine synthetase has been replaced with another amino acid residue (US2003/0148474A).

Examples of the methods for imparting, increasing, or enhancing an ability to produce L-glutamine to or in coryneform bacteria also can include the method of imparting 6-diazo-5-oxo-norleucine resistance (Japanese Patent Laid-open (Kokai) No. 3-232497), the method of imparting purine analogue resistance and methionine sulfoxide resistance (Japanese Patent Laid-open (Kokai) No. 61-202694), and the method of imparting α-ketomalonic acid resistance (Japanese Patent Laid-open (Kokai) No. 56-151495). Specific examples of coryneform bacteria able to produce L-glutamine can include, for example, the following strains:

*Corynebacterium glutamicum* (*Brevibacterium flavum*) AJ11573 (FERM P-5492, Japanese Patent Laid-open (Kokai) No. 56-151495)

*Corynebacterium glutamicum* (*Brevibacterium flavum*) AJ11576 (FERM BP-10381, Japanese Patent Laid-open (Kokai) No. 56-151495)

*Corynebacterium glutamicum* (*Brevibacterium flavum*) AJ12212 (FERM P-8123, Japanese Patent Laid-open (Kokai) No. 61-202694)

<L-Proline-Producing Bacteria>

Examples of methods for imparting, increasing, or enhancing an ability to produce L-proline can include, for example, a method of modifying a bacterium so that the bacterium has an increased activity or activities of one or more kinds of L-proline biosynthesis enzymes. Examples of such enzymes can include glutamate-5-kinase (proB), γ-glutamylphosphate reductase, and pyroline-5-carboxylate reductase (putA). For enhancing the activity of such an enzyme, for example, the proB gene encoding a glutamate kinase desensitized to feedback inhibition by L-proline (German Patent No. 3127361) can be used.

Examples of methods for imparting, increasing, or enhancing an ability to produce L-proline also can include, for example, a method of modifying a bacterium so that the bacterium has a reduced activity of an enzyme involved in decomposition of L-proline. Examples of such an enzyme can include proline dehydrogenase and ornithine aminotransferase.

Specific examples of bacteria able to produce L-proline and parental strains that can be used to derive them can include, for example, *E. coli* NRRL B-12403 and NRRL B-12404 (British Patent No. 2075056), *E. coli* VKPM B-8012 (Russian Patent Application No. 2000124295), *E. coli* plasmid mutant strains described in German Patent No. 3127361, *E. coli* plasmid mutant strains described by Bloom F. R. et al. (The 15th Miami winter symposium, 1983, p. 34), *E. coli* 702 strain (VKPM B-8011), which is a 3,4-dehydroxyproline and azetidine-2-carboxylate resistant strain, and *E. coli* 702ilvA strain (VKPM B-8012), which is an ilvA gene-deficient strain of the 702 strain (EP1172433).

<L-Threonine-Producing Bacteria>

Examples of methods for imparting, increasing, or enhancing an ability to produce L-threonine can include, for example, a method of modifying a bacterium so that the bacterium has an increased activity or activities of one or more of the L-threonine biosynthesis enzymes. Examples of such enzymes can include, but not particularly limited to, aspartokinase III (lysC), aspartate semialdehyde dehydrogenase (asd), aspartokinase I (thrA), homoserine kinase (thrB), threonine synthase (thrC), and aspartate aminotransferase (aspartate transaminase) (aspC). Among these enzymes, it is preferable to enhance activity or activities of one or more of aspartokinase III, aspartate semialdehyde dehydrogenase, aspartokinase I, homoserine kinase, aspartate aminotransferase, and threonine synthase. Any of the genes encoding the L-threonine biosynthesis enzymes can be introduced into a bacterium having a reduced ability to decompose threonine. Examples of such a strain in which threonine decomposition is suppressed can include, for example, the *E. coli* TDH6 strain, which is deficient in the threonine dehydrogenase activity (Japanese Patent Laid-open (Kokai) No. 2001-346578).

The activities of the L-threonine biosynthesis enzymes are inhibited by the endproduct, L-threonine. Therefore, when constructing strains to be used in production of L-threonine, the genes of the L-threonine biosynthesis enzymes can be modified so that the enzymes are desensitized to feedback inhibition by L-threonine. The aforementioned thrA, thrB, and thrC genes constitute the threonine operon, which forms an attenuator structure. The expression of the threonine operon is inhibited by isoleucine and threonine in the culture broth and also suppressed by attenuation. Therefore, expression of the threonine operon can be enhanced by removing the leader sequence or the attenuator in the attenuation region (Lynn, S. P., Burton, W. S., Donohue, T. J., Gould, R. M., Gumport, R. L, and Gardner, J. F., J. Mol. Biol. 194:59-69 (1987); WO02/26993; WO2005/049808; and WO2003/097839).

The native promoter of the threonine operon is present upstream of the threonine operon, and can be replaced with a non-native promoter (WO98/04715). Also, the threonine operon may be constructed so that the threonine biosynthesis genes are expressed under the control of the repressor and promoter of λ-phage (EP0593792B). Furthermore, a bacterium can be modified so that it is desensitized to feedback inhibition by L-threonine also by selecting a strain resistant to α-amino-β-hydroxyisovaleric acid (AHV), which is an L-threonine analogue.

The expression of the threonine operon that is modified so that it is desensitized to feedback inhibition by L-threonine as described above can be increased in a host by increasing the copy number thereof or by ligating it to a potent promoter. The copy number can be increased by introducing a plasmid containing the threonine operon into a host. The copy number can also be increased by transferring the threonine operon to the genome of a host using a transposon, Mu-phage, or the like.

Examples of methods for imparting, increasing, or enhancing an ability to produce L-threonine also can include, for example, a method of imparting L-threonine resistance to a host, and a method of imparting L-homoserine resistance to a host. Such resistance can be imparted by, for example, enhancing the expression of a gene that imparts L-threonine resistance or a gene that imparts L-homoserine resistance. Examples of the genes that impart the above-mentioned resistance can include the rhtA gene (Res. Microbiol. 154:123-135 (2003)), rhtB gene (EP0994190A), rhtC gene (EP1013765A), yfiK gene, and yeaS gene (EP1016710A). Methods for imparting L-threonine resistance to a host are described in EP0994190A and WO90/04636.

Specific examples of bacteria able to produce L-threonine and parental strains that can be used to derive them can include, for example, *E. coli* TDH-6/pVIC40 (VKPM B-3996, U.S. Pat. Nos. 5,175,107 and 5,705,371), *E. coli* 472T23/pYN7 (ATCC 98081, U.S. Pat. No. 5,631,157), *E. coli* NRRL-21593 (U.S. Pat. No. 5,939,307), *E. coli* FERM BP-3756 (U.S. Pat. No. 5,474,918), *E. coli* FERM BP-3519 and FERM BP-3520 (U.S. Pat. No. 5,376,538), *E. coli* MG442 (Gusyatiner et al., Genetika (in Russian), 14, 947-956 (1978)), *E. coli* VL643 and VL2055 (EP1149911A), and *E. coli* VKPM B-5318 (EP0593792B).

The VKPM B-3996 strain can be obtained by introducing the plasmid pVIC40 into the TDH-6 strain. The TDH-6 strain is able to assimilate sucrose, is deficient in the thrC gene, and the ilvA gene has a leaky mutation. The TDH-6 strain also has a mutation in the rhtA gene, which imparts resistance to a high concentration of threonine or homoserine. The plasmid pVIC40 is a plasmid obtained by inserting the thrA*BC operon containing a mutant thrA gene encoding an aspartokinase-homoserine dehydrogenase I that is resistant to feedback inhibition by threonine and the wild-type thrBC genes into an RSF1010-derived vector (U.S. Pat. No. 5,705,371). This mutant thrA gene encodes an aspartokinase-homoserine dehydrogenase I which is substantially desensitized to feedback inhibition by threonine. The B-3996 strain was deposited on Nov. 19, 1987 at the All-Union Scientific Center of Antibiotics (Nagatinskaya Street 3-A, 117105 Moscow, Russia) under the accession number RIA 1867. This strain was also deposited at the Russian National Collection of Industrial Microorganisms (VKPM, FGUP GosNII Genetika, 1 Dorozhny proezd., 1 Moscow 117545, Russia) on Apr. 7, 1987 under the accession number VKPM B-3996.

The VKPM B-5318 strain is prototrophic with regard to isoleucine, and harbors the plasmid pPRT614, which corresponds to the plasmid pVIC40 in which the regulatory region of the threonine operon is replaced with the temperature-sensitive λ-phage C1 repressor and PR promoter. The VKPM B-5318 strain was deposited at the Russian National Collection of Industrial Microorganisms (VKPM, FGUP GosNII Genetika, 1 Dorozhny proezd., 1 Moscow 117545, Russia) on May 3, 1990 under the accession number of VKPM B-5318.

The thrA gene which encodes aspartokinase-homoserine dehydrogenase I of *E. coli* has been elucidated (nucleotide numbers 337 to 2799, GenBank accession NC 000913.2, gi: 49175990). The thrA gene is located between the thrL and thrB genes on the chromosome of *E. coli* K-12. The thrB gene which encodes homoserine kinase of *Escherichia coli* has been elucidated (nucleotide numbers 2801 to 3733, GenBank accession NC 000913.2, gi: 49175990). The thrB gene is located between the thrA and thrC genes on the chromosome of *E. coli* K-12. The thrC gene which encodes threonine synthase of *E. coli* has been elucidated (nucleotide numbers 3734 to 5020, GenBank accession NC 000913.2, gi: 49175990). The thrC gene is located between the thrB gene and the yaaX open reading frame on the chromosome of *E. coli* K-12. The thrA*BC operon containing a mutant thrA gene which encodes an aspartokinase-homoserine dehydrogenase I that is resistant to feedback inhibition by threonine and the wild-type thrBC genes can be obtained from the well-known plasmid pVIC40, which is present in the threonine-producing *E. coli* strain VKPM B-3996 (U.S. Pat. No. 5,705,371).

The rhtA gene of *E. coli* is located at 18 min on the *E. coli* chromosome close to the glnHPQ operon, which encodes components of the glutamine transport system. The rhtA gene is identical to ORF1 (ybiF gene, nucleotide numbers 764 to 1651, GenBank accession number AAA218541, gi:440181) and locates between the pexB and ompX genes. The unit expressing a protein encoded by the ORF1 has been designated the rhtA gene (rht: resistance to homoserine and threonine). It has also been revealed that the rhtA23 mutation that imparts resistance to a high concentration of threonine or homoserine is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, abstract No. 457; EP1013765A).

The asd gene of E. coli has already been elucidated (nucleotide numbers 3572511 to 3571408, GenBank accession NC 000913.1, gi:16131307), and can be obtained by PCR (White, T. J., et al., Trends Genet, 5:185-189, 1989) utilizing primers prepared on the basis of the nucleotide sequence of the gene. The asd genes of other microorganisms can also be obtained in a similar manner.

The aspC gene of E. coli has also already been elucidated (nucleotide numbers 983742 to 984932, GenBank accession NC 000913.1, gi:16128895), and can be obtained by PCR utilizing primers prepared on the basis of the nucleotide sequence of the gene. The aspC genes of other microorganisms can also be obtained in a similar manner.

Furthermore, examples of coryneform bacteria having L-threonine-producing ability can include, for example, Corynebacterium acetoacidophilum AJ12318 (FERM BP-1172, U.S. Pat. No. 5,188,949).

<L-Lysine-Producing Bacteria>

Examples of methods for imparting, increasing, or enhancing an ability to produce L-lysine can include, for example, a method of modifying a bacterium so that the bacterium has an increased activity or activities of one or more of the L-lysine biosynthesis enzymes. Examples of such enzymes can include, but are not particularly limited to, dihydrodipicolinate synthase (dapA), aspartokinase III (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), aspartate aminotransferase (aspartate transaminase) (aspC), diaminopimelate epimerase (dapF), tetrahydrodipicolinate succinylase (dapD), succinyl diaminopimelate deacylase (dapE), and aspartase (aspA) (EP1253195A). The activity or activities of one or more of, for example, dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyl diaminopimelate deacylase can be enhanced. Furthermore, bacteria with an ability to produce L-lysine and parental strains that can be used to derive them can express an increased level of the gene involved in energy efficiency (cyo) (EP1170376A), the gene encoding nicotinamide nucleotide transhydrogenase (pntAB) (U.S. Pat. No. 5,830,716), the ybjE gene (WO2005/073390), or combinations of these. Since aspartokinase III (lysC) is subject to feedback inhibition by L-lysine, a mutant lysC gene encoding an aspartokinase III that is desensitized to feedback inhibition by L-lysine (U.S. Pat. No. 5,932,453) may be used to enhance the activity of this enzyme. Examples of the aspartokinase III that is desensitized to feedback inhibition by L-lysine can include Escherichia coli aspartokinase III that has one or more mutations that result in replacing the methionine residue at position 318 with an isoleucine residue; a mutation that results in replacing the glycine residue at position 323 with an aspartic acid residue; and a mutation that results in replacing the threonine residue at position 352 with an isoleucine residue (U.S. Pat. Nos. 5,661,012 and 6,040,160). Furthermore, since dihydrodipicolinate synthase (dapA) is subject to feedback inhibition by L-lysine, a mutant dapA gene encoding a dihydrodipicolinate synthase that is desensitized to feedback inhibition by L-lysine may be used to enhance the activity of this enzyme. Examples of the dihydrodipicolinate synthase that is desensitized to feedback inhibition by L-lysine can include Escherichia coli dihydrodipicolinate synthase having a mutation that results in replacing the histidine residue at position 118 with a tyrosine residue (U.S. Pat. No. 6,040, 160).

Examples of methods for imparting, increasing, or enhancing an ability to produce L-lysine also can include, for example, a method of modifying a bacterium so that it has a reduced activity or activities of one or more of the enzymes that catalyze a reaction branching away from the biosynthetic pathway of L-lysine to generate a compound other than L-lysine. Examples of such enzymes can include, but are not particularly limited to, homoserine dehydrogenase, lysine decarboxylase (U.S. Pat. No. 5,827,698), and malic enzyme (WO2005/010175).

Furthermore, examples of methods for imparting, increasing, or enhancing an ability to produce L-lysine to or in coryneform bacteria also can include a method of modifying the bacteria so that the activity of a lysine excretion system (lysE) is increased (WO97/23597). The lysE gene of Corynebacterium glutamicum ATCC 13032 corresponds to the sequence complementary to the sequence of the nucleotide numbers 1,329,712 to 1,330,413 in the genome sequence registered as Genbank Accession No. NC_006958 (VERSION NC_006958.1 GI:62388892) in the NCBI database. The LysE protein of Corynebacterium glutamicum ATCC 13032 is registered as GenBank accession No. YP_225551 (YP_225551.1 GI:62390149).

Examples of bacteria that can produce L-lysine bacteria and parental strains that can be used to derive them also can include mutant strains having resistance to an L-lysine analogue. L-Lysine analogues inhibit the growth of bacteria such as bacteria of the family Enterobacteriaceae and coryneform bacteria, but this inhibition is fully or partially released when L-lysine is present in the medium. Examples of these L-lysine analogues can include, but are not particularly limited to, oxalysine, lysine hydroxamate, S-(2-aminoethyl)-L-cysteine (AEC), γ-methyllysine, and α-chlorocaprolactam. Mutant strains that are resistant to these lysine analogues can be obtained by subjecting a bacterium to a conventional artificial mutagenesis treatment.

Specific examples of bacteria able to produce L-lysine bacteria and parental strains that can be used to derive them can include E. coli AJ11442 (FERM BP-1543, NRRL B-12185, U.S. Pat. No. 4,346,170) and E. coli VL611. In these strains, aspartokinase is desensitized to feedback inhibition by L-lysine.

Specific examples of bacteria able to produce L-lysine bacteria and parental strains that can be used to derive them also can include the E. coli WC196 strain. The WC196 strain was bred by imparting AEC resistance to the W3110 strain, which was derived from E. coli K-12 (U.S. Pat. No. 5,827, 698). The WC196 strain was designated E. coli AJ13069 and deposited at the National Institute of Bioscience and Human-Technology, Agency of Industrial Science and Technology (currently, independent administrative agency, National Institute of Technology and Evaluation, International Patent Organism Depositary, #120, 2-5-8 Kazusakamatari, Kisarazu-shi, Chiba-ken, 292-0818, Japan) on Dec. 6, 1994 and assigned an accession number of FERM P-14690. Then, the deposit was converted to an international deposit under the provisions of the Budapest Treaty on Sep. 29, 1995, and assigned an accession number of FERM BP-5252 (U.S. Pat. No. 5,827,698).

Examples of bacteria able to produce L-lysine can include *E. coli* WC196ΔcadAΔldc and *E. coli* WC196ΔcadAΔldc/pCABD2 (WO2010/061890). The strain *E. coli* WC196ΔcadAΔldc is constructed from the WC196 strain by disrupting the cadA and ldcC genes encoding lysine decarboxylase. The WC196ΔcadAΔldc/pCABD2 strain was constructed by introducing the plasmid pCABD2 containing the lysine biosynthesis enzyme genes (U.S. Pat. No. 6,040,160) into the WC196ΔcadAΔldc strain. The WC196ΔcadAΔldc strain, designated as AJ110692, was deposited at the independent administrative agency, National Institute of Advanced Industrial Science and Technology, International Patent Organism Depositary (currently, independent administrative agency, National Institute of Technology and Evaluation, International Patent Organism Depositary, #120, 2-5-8 Kazusakamatari, Kisarazu-shi, Chiba-ken, 292-0818, Japan) on Oct. 7, 2008 as an international deposit, and assigned an accession number of FERM BP-11027. The plasmid pCABD2 contains a mutant *Escherichia coli* dapA gene that encodes a dihydrodipicolinate synthase (DDPS) having a mutation that results in desensitization to feedback inhibition by L-lysine (H118Y), a mutant *Escherichia coli* lysC gene that encodes aspartokinase III having a mutation for desensitization to feedback inhibition by L-lysine (T352I), the *Escherichia coli* dapB gene that encodes dihydrodipicolinate reductase, and the *Brevibacterium lactofermentum* ddh gene that encodes diaminopimelate dehydrogenase.

Examples of bacteria able to produce L-lysine also can include *E. coli* AJIK01 (NITE BP-01520). The AJIK01 strain was designated *E. coli* AJ111046, and deposited at the independent administrative agency, National Institute of Technology and Evaluation, International Patent Organism Depositary (#122, 2-5-8 Kazusakamatari, Kisarazu-shi, Chiba-ken, 292-0818, Japan) on Jan. 29, 2013. Then, it was converted to an international deposit under the provisions of the Budapest Treaty on May 15, 2014, and assigned an accession number of NITE BP-01520.

Examples of coryneform bacteria able to produce L-lysine can include, for example, the AEC-resistant mutant strains (*Corynebacterium glutamicum* (*Brevibacterium lactofermentum* AJ11082) (NRRL B-11470) strain etc., Japanese Patent Publication (Kokoku) Nos. 56-1914, 56-1915, 57-14157, 57-14158, 57-30474, 58-10075, 59-4993, 61-35840, 62-24074, 62-36673, 5-11958, 7-112437, and 7-112438); mutant strains requiring an amino acid such as L-homoserine for their growth (Japanese Patent Publication Nos. 48-28078 and 56-6499); mutant strains resistant to AEC and further requiring an amino acid such as L-leucine, L-homoserine, L-proline, L-serine, L-arginine, L-alanine, and L-valine (U.S. Pat. Nos. 3,708,395 and 3,825,472); mutant strains resistant to DL-α-amino-ε-caprolactam, α-amino-lauryllactam, aspartic acid analogue, sulfa drug, quinoid, and N-lauroylleucine; mutant strains resistant to an oxaloacetate decarboxylase inhibitor or a respiratory chain enzyme inhibitor (Japanese Patent Laid-open (Kokai) Nos. 50-53588, 50-31093, 52-102498, 53-9394, 53-86089, 55-9783, 55-9759, 56-32995, 56-39778, Japanese Patent Publication Nos. 53-43591 and 53-1833); mutant strains requiring inositol or acetic acid (Japanese Patent Laid-open (Kokai) Nos. 55-9784 and 56-8692); mutant strains that are susceptible to fluoropyruvic acid or a temperature of 34° C. or higher (Japanese Patent Laid-open (Kokai) Nos. 55-9783 and 53-86090); and mutant strains resistant to ethylene glycol (U.S. Pat. No. 4,411,997).

<L-Arginine-Producing Bacteria>

Examples of methods for imparting, increasing, or enhancing an ability to produce L-arginine can include, for example, a method of modifying a bacterium so that the bacterium has an increased activity or activities of one or more of the L-arginine biosynthesis enzymes. Examples of such enzymes can include, but are not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyl transferase (argF, argI), argininosuccinate synthetase (argG), argininosuccinate lyase (argH), ornithine acetyl transferase (argJ), and carbamoyl phosphate synthetase (carAB). As the N-acetylglutamate synthase gene (argA), for example, a gene encoding a mutant N-acetylglutamate synthase that is desensitized to feedback inhibition by L-arginine by substitution for the amino acid residues corresponding to the positions 15 to 19 of the wild type enzyme (EP1170361A) can be used.

Specific examples of bacteria able to produce L-arginine and parental strains that can be used to derive them can include, for example, the *E. coli* 237 strain (VKPM B-7925, US2002/058315A1), derivative strains thereof introduced with the argA gene encoding a mutant N-acetyl glutamate synthase (Russian Patent Application No. 2001112869, EP1170361A1), *E. coli* 382 strain derived from the 237 strain and having an improved acetic acid-assimilating ability (VKPM B-7926, EP1170358A1), and *E. coli* 382ilvA+ strain, which was obtained from the 382 strain by introducing the wild-type ilvA gene from *E. coli* K-12 strain thereto. The *E. coli* strain 237 was deposited at the Russian National Collection of Industrial Microorganisms (VKPM, FGUP GosNII Genetika, 1 Dorozhny proezd., 1 Moscow 117545, Russia) on Apr. 10, 2000 under an accession number of VKPM B-7925, and the deposit was converted to an international deposit under the provisions of Budapest Treaty on May 18, 2001. The *E. coli* 382 strain was deposited at the Russian National Collection of Industrial Microorganisms (VKPM, FGUP GosNII Genetika, 1 Dorozhny proezd., 1 Moscow 117545, Russia) on Apr. 10, 2000 under accession number of VKPM B-7926.

Examples of bacteria able to produce L-arginine and parental strains that can be used to derive them also can include strains resistant to amino acid analogues, and so forth. Examples of such strains can include *E. coli* mutant strains resistant to α-methylmethionine, p-fluorophenylalanine, D-arginine, arginine hydroxamate, S-(2-aminoethyl)-cysteine, α-methylserine, β-2-thienylalanine, or sulfaguanidine (Japanese Patent Laid-open (Kokai) No. 56-106598).

Examples of bacteria able to produce L-arginine and parent strains that can be used to derive them also can include coryneform bacteria deficient in ArgR, which is an arginine repressor (US2002-0045223A), and a strain in which glutamine synthetase activity is increased (US2005-0014236A).

Examples of bacteria able to produce L-arginine and parent strains that can be used to derive them also can include mutant strains of coryneform bacteria, mutant strains resistant to an amino acid analogue or the like. Examples of such strains can include, for example, strains having resistance to 2-thiazolealanine and further exhibiting auxotrophy for L-histidine, L-proline, L-threonine, L-isoleucine, L-methionine, or L-tryptophan (Japanese Patent Laid-open (Kokai) No. 54-44096); strains resistant to ketomalonic acid, fluoromalonic acid, or monofluoroacetic acid (Japanese Patent Laid-open (Kokai) No. 57-18989); strains resistant to argininol (Japanese Patent Publication No. 62-24075); strains resistant to X-guanidine (X represents an aliphatic chain or a derivative thereof, Japanese Patent Laid-open (Kokai) No. 2-186995); and strains resistant to arginine hydroxamate and 6-azauracil (Japanese Patent Laid-open (Kokai) No. 57-150381). Specific examples of coryneform bacteria having L-arginine-producing ability can include the following strains:

*Corynebacterium glutamicum* (*Brevibacterium flavum*) AJ11169 (FERM BP-6892)

*Corynebacterium glutamicum* (*Brevibacterium lactofermentum*) AJ12092 (FERM BP-6906)

*Corynebacterium glutamicum* (*Brevibacterium flavum*) AJ11336 (FERM BP-6893)

*Corynebacterium glutamicum* (*Brevibacterium flavum*) AJ11345 (FERM BP-6894)

*Corynebacterium glutamicum* (*Brevibacterium lactofermentum*) AJ12430 (FERM BP-2228)

<L-Citrulline-Producing Bacteria and L-Ornithine-Producing Bacteria>

L-citrulline and L-ornithine are intermediates in the biosynthetic pathway of L-arginine. Hence, examples of methods for imparting, increasing, or enhancing an ability to produce L-citrulline and/or L-ornithine can include, for example, a method of modifying a bacterium to have an increased activity or activities of one or more of the L-arginine biosynthesis enzymes. Examples of such enzymes can include, but are not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), ornithine carbamoyl transferase (argF, argI), ornithine acetyl transferase (argJ), and carbamoyl phosphate synthetase (carAB), for L-citrulline. Furthermore, examples of such enzymes can include, but are not particularly limited to, N-acetylglutamate synthase (argA), N-acetylglutamate kinase (argB), N-acetylglutamyl phosphate reductase (argC), acetylornithine transaminase (argD), acetylornithine deacetylase (argE), and ornithine acetyl transferase (argJ), for L-ornithine.

A bacterium able to produce L-citrulline can be easily obtained from, for example, a bacterium that produces L-arginine such as the *E. coli* 382 strain (VKPM B-7926) by decreasing the activity of argininosuccinate synthetase encoded by argG gene. Also, a bacterium able to produce L-ornithine can be easily obtained from, for example, an L-arginine bacterium such as the *E. coli* 382 strain (VKPM B-7926) by decreasing the activity of ornithine carbamoyl transferase encoded by argF and argI genes.

Specific examples of bacteria able to produce L-citrulline and parental strains that can be used to derive them can include, for example, strains belonging to the genus *Escherichia*, such as the *E. coli* strains 237/pMADS11, 237/pMADS12, and 237/pMADS13, which have a mutant N-acetylglutamate synthase (Russian patent No. 2,215,783, U.S. Pat. No. 6,790,647, and EP1170361B1), *E. coli* strains 333 (VKPM B-8084) and 374 (VKPM B-8086), which have carbamoyl phosphate synthetase resistant to feedback inhibition (Russian patent No. 2,264,459), and *E. coli* strains having an increased activity of α-ketoglutarate synthase and having a modified activity of ferredoxin $NADP^+$ reductase, pyruvate synthase, and/or α-ketoglutarate dehydrogenase (EP2133417A).

<L-Histidine-Producing Bacteria>

Examples of methods for imparting, increasing, or enhancing an ability to produce L-histidine can include, for example, a method of modifying a bacterium to have an increased activity or activities of one or more of the L-histidine biosynthesis enzymes. Examples of such enzymes can include, but are not particularly limited to, ATP phosphoribosyltransferase (hisG), phosphoribosyl AMP cyclohydrolase (hisI), phosphoribosyl-ATP pyrophosphohydrolase (hisI), phosphoribosylformimino-5-aminoimidazole carboxamide ribotide isomerase (hisA), amidotransferase (hisH), histidinol phosphate aminotransferase (hisC), histidinol phosphatase (hisB), and histidinol dehydrogenase (hisD).

Among these enzymes, the L-histidine biosynthesis enzymes encoded by hisG and hisBHAFI are known to be inhibited by L-histidine. Therefore, the ability to produce L-histidine can be imparted or enhanced by, for example, introducing a mutation that confers resistance to feedback inhibition into the gene encoding ATP phosphoribosyltransferase (hisG) (Russian Patent Nos. 2,003,677 and 2,119,536).

Specific examples of bacteria able to produce L-histidine and parental strains that can be used to derive them can include, for example, strains belonging to the genus *Escherichia*, such as the *E. coli* 24 strain (VKPM B-5945, RU2003677), *E. coli* NRRL B-12116 to B-12121 (U.S. Pat. No. 4,388,405), *E. coli* H-9342 (FERM BP-6675) and H-9343 (FERM BP-6676, U.S. Pat. No. 6,344,347), *E. coli* H-9341 (FERM BP-6674, EP1085087), *E. coli* AI80/pFM201 (U.S. Pat. No. 6,258,554), *E. coli* FERM P-5038 and FERM P-5048, which have been introduced with a vector carrying a DNA encoding an L-histidine-biosynthesis enzyme (Japanese Patent Laid-open (Kokai) No. 56-005099), *E. coli* strains introduced with a gene for amino acid transport (EP1016710A), and *E. coli* 80 strain, which has been imparted with resistance to sulfaguanidine, DL-1, 2,4-triazole-3-alanine, and streptomycin (VKPM B-7270, Russian Patent No. 2119536).

<L-Cysteine-Producing Bacteria>

Examples of methods for imparting, increasing, or enhancing an ability to produce L-cysteine can include, for example, a method of modifying a bacterium to have an increased activity or activities of one or more of the L-cysteine biosynthesis enzymes. Examples of such enzymes can include, but are not particularly limited to, serine acetyltransferase (cysE) and 3-phosphoglycerate dehydrogenase (serA). The serine acetyltransferase activity can be enhanced by, for example, introducing a mutant cysE gene encoding a mutant serine acetyltransferase resistant to feedback inhibition by cysteine into a bacterium. Such a mutant serine acetyltransferase is disclosed in, for example, Japanese Patent Laid-open (Kokai) No. 11-155571 and US2005-0112731A. Furthermore, the 3-phosphoglycerate dehydrogenase activity can be enhanced by, for example, introducing a mutant serA gene encoding a mutant 3-phosphoglycerate dehydrogenase resistant to feedback inhibition by serine into a bacterium. Such a mutant 3-phosphoglycerate dehydrogenase is disclosed in, for example, U.S. Pat. No. 6,180,373.

Furthermore, examples of methods for imparting, increasing, or enhancing an ability to produce L-cysteine also can include, for example, a method of modifying a bacterium to have a reduced activity or activities of one or more of the enzymes that catalyze a reaction branching away from the biosynthesis pathway of L-cysteine to generate a compound other than L-cysteine. Examples of such enzymes can include, for example, enzymes involved in decomposition of L-cysteine. Examples of the enzymes involved in decomposition of L-cysteine can include, but are not particularly limited to, cystathionine-β-lyase (metC, Japanese Patent Laid-open (Kokai) No. 11-155571; Chandra et al., Biochemistry, 21 (1982) 3064-3069), tryptophanase (tnaA, Japanese Patent Laid-open (Kokai) No. 2003-169668; Austin Newton et al., J. Biol. Chem., 240 (1965) 1211-1218), 0-acetylserine sulfhydrylase B (cysM, Japanese Patent Laid-open (Kokai)

No. 2005-245311), the malY gene product (Japanese Patent Laid-open (Kokai) No. 2005-245311), the d0191 gene product of *Pantoea ananatis* (Japanese Patent Laid-open (Kokai) No. 2009-232844), and cysteine desulfhydrase (aecD, Japanese Patent Laid-open (Kokai) No. 2002-233384).

Furthermore, examples of methods for imparting, increasing, or enhancing an ability to produce L-cysteine also can include, for example, a method of enhancing the L-cysteine excretory system, and a method of enhancing the sulfate/thiosulfate transport system. Examples of proteins of the L-cysteine excretory system can include the protein encoded by the ydeD gene (Japanese Patent Laid-open (Kokai) No. 2002-233384), the protein encoded by the yfiK gene (Japanese Patent Laid-open (Kokai) No. 2004-49237), the proteins encoded by the emrAB, emrKY, yojIH, acrEF, bcr, and cusA genes (Japanese Patent Laid-open (Kokai) No. 2005-287333), and the protein encoded by the yeaS gene (Japanese Patent Laid-open (Kokai) No. 2010-187552). Examples of the proteins of the sulfate/thiosulfate transport system can include the proteins encoded by the cysPTWAM gene cluster.

Specific examples of bacteria able to produce L-cysteine bacteria and parental strains that can be used to derive them include, for example, *E. coli* JM15 transformed with different cysE alleles encoding feedback-resistant serine acetyltransferases (U.S. Pat. No. 6,218,168, Russian patent application 2003121601), *E. coli* W3110 having an overexpressed gene encoding a protein suitable for secretion of a cytotoxic substance (U.S. Pat. No. 5,972,663), *E. coli* strains having a reduced cysteine desulfohydrase activity (Japanese Patent Laid-open (Kokai) No. 11-155571), and *E. coli* W3110 having increased activity of a positive transcriptional regulator for cysteine regulon encoded by the cysB gene (WO01/27307A1).

Furthermore, examples of coryneform bacteria able to produce L-cysteine can include coryneform bacteria having serine acetyltransferase desensitized to feedback inhibition by L-cysteine thereby to show enhanced intracellular serine acetyltransferase activity (Japanese Patent Laid-open (Kokai) No. 2002-233384).

<L-Serine-Producing Bacteria>

Examples of methods for imparting, increasing, or enhancing an ability to produce L-serine can include, for example, a method of modifying a bacterium to have an increased activity or activities of one or more of the L-serine biosynthesis enzymes. Examples of such enzymes can include, but are not particularly limited to, 3-phosphoglycerate dehydrogenase (serA), phosphoserine transaminase (serC), and phosphoserine phosphatase (serB) (Japanese Patent Laid-open (Kokai) No. 11-253187). 3-phosphoglycerate dehydrogenase activity can be increased by, for example, introducing a mutant serA gene encoding a mutant 3-phosphoglycerate dehydrogenase resistant to feedback inhibition by L-serine into a bacterium. The mutant 3-phosphoglycerate dehydrogenase is disclosed in, for example, U.S. Pat. No. 6,180,373.

Examples of bacteria able to produce L-serine and parental strains that can be used to derive them can include, for example, coryneform bacteria resistant to azaserine or β-(2-thienyl)-DL-alanine and deficient in L-serine decomposition ability (Japanese Patent Laid-open (Kokai) No. 10-248588). Specific examples of such coryneform bacteria can include, for example, *Corynebacterium glutamicum* (*Brevibacterium flavum*) AJ13324 (FERM P-16128), which is resistant to azaserine and deficient in L-serine decomposition ability, and *Corynebacterium glutamicum* (*Brevibacterium flavum*) AJ13325 (FERM P-16129), which is resistant to β-(2-thienyl)-DL-alanine and deficient in L-serine decomposition ability (Japanese Patent Laid-open (Kokai) No. 10-248588).

<L-Methionine-Producing Bacteria>

Examples of bacteria able to produce L-methionine and parental strains that can be used to derive them can include L-threonine auxotrophic strains and mutant strains resistant to norleucine (Japanese Patent Laid-open (Kokai) No. 2000-139471). Examples of bacteria able to produce L-methionine and parental strains that can be used to derive them also can include a strain containing a mutant homoserine transsuccinylase resistant to feedback inhibition by L-methionine (Japanese Patent Laid-open (Kokai) No. 2000-139471, US2009-0029424A). Since L-methionine is biosynthesized via L-cysteine as an intermediate, L-methionine-producing ability can also be improved by improving L-cysteine-producing ability (Japanese Patent Laid-open (Kokai) No. 2000-139471, US2008-0311632A).

Specific examples of bacteria that are able to produce L-methionine and parental strains that can be used to derive them can include, for example, *E. coli* AJ11539 (NRRL B-12399), *E. coli* AJ11540 (NRRL B-12400), *E. coli* AJ11541 (NRRL B-12401), *E. coli* AJ11542 (NRRL B-12402, British Patent No. 2075055), the *E. coli* 218 strain (VKPM B-8125, Russian Patent No. 2209248) and the 73 strain (VKPM B-8126, Russian Patent No. 2215782), which are resistant to norleucine, which is an analogue of L-methionine, and *E. coli* AJ13425 (FERMP-16808, Japanese Patent Laid-open (Kokai) No. 2000-139471). The AJ13425 strain is an L-threonine auxotrophic strain derived from the *E. coli* W3110, in which the methionine repressor is deleted, the intracellular S-adenosylmethionine synthetase activity is attenuated, and the intracellular homoserine transsuccinylase activity, cystathionine γ-synthase activity, and aspartokinase-homoserine dehydrogenase II activity are enhanced.

<L-Leucine-Producing Bacteria>

Examples of methods for imparting, increasing, or enhancing an ability to produce L-leucine can include, for example, a method of modifying a bacterium to have an increased activity or activities of one or more of the L-leucine biosynthesis enzymes. Examples of such enzymes can include, but are not particularly limited to, the enzymes encoded by the genes of the leuABCD operon. Furthermore, to enhance the activity of such an enzyme, for example, the mutant leuA gene encoding an isopropyl maleate synthase desensitized to feedback inhibition by L-leucine (U.S. Pat. No. 6,403,342) can be used.

Specific examples of bacteria able to produce L-leucine and parental strains that can be used to derive them can include, for example, strains belonging to the genus *Escherichia*, such as *E. coli* strains resistant to leucine (for example, the 57 strain (VKPM B-7386, U.S. Pat. No. 6,124,121)), *E. coli* strains resistant to an leucine analogue such as β-2-thienylalanine, 3-hydroxyleucine, 4-azaleucine, and 5,5,5-trifluoroleucine (Japanese Patent Publication (Kokoku) No. 62-34397 and Japanese Patent Laid-open (Kokai) No. 8-70879), *E. coli* strains obtained by a gene engineering technique described in WO96/06926, and *E. coli* H-9068 (Japanese Patent Laid-open (Kokai) No. 8-70879).

Examples of coryneform bacteria able to produce L-leucine can include, for example, *Corynebacterium glutamicum* (*Brevibacterium lactofermentum*) AJ3718 (FERM P-2516), which is resistant to 2-thiazole alanine and β-hydroxyleucine and auxotrophic for isoleucine and methionine.

<L-Isoleucine-Producing Bacteria>

Examples of methods for imparting, increasing, or enhancing an ability to produce L-isoleucine can include, for example, a method of modifying a bacterium to have increased activity or activities of one or more of the L-isoleucine biosynthesis enzymes. Examples of such enzymes can include, but are not particularly limited to, threonine deaminase and acetohydroxy acid synthase (Japanese Patent Laid-open (Kokai) No. 2-458, EP0356739A, U.S. Pat. No. 5,998,178).

Specific examples of bacteria able to produce L-isoleucine and parental strains that can be used to derive them can include, for example, *Escherichia* bacteria such as mutant strains resistant to 6-dimethylaminopurine (Japanese Patent Laid-open (Kokai) No. 5-304969), mutant strains resistant to an isoleucine analogue such as thiaisoleucine and isoleucine hydroxamate, and mutant strains resistant to such an isoleucine analogue and further having resistance to DL-ethionine and/or arginine hydroxamate (Japanese Patent Laid-open (Kokai) No. 5-130882).

Examples of coryneform bacteria able to produce L-isoleucine can include, for example, a coryneform bacterium in which brnE gene encoding a branched chain amino acid excretion protein is amplified (Japanese Patent Laid-open (Kokai) No. 2001-169788), a coryneform bacterium to which L-isoleucine-producing ability is imparted by protoplast fusion with an L-lysine-producing bacterium (Japanese Patent Laid-open (Kokai) No. 62-74293), a coryneform bacterium in which homoserine dehydrogenase is enhanced (Japanese Patent Laid-open (Kokai) No. 62-91193), the threonine hydroxamate-resistant strain (Japanese Patent Laid-open (Kokai) No 62-195293), the α-ketomalonic acid-resistant strain (Japanese Patent Laid-open (Kokai) No. 61-15695), the methyllysine-resistant strain (Japanese Patent Laid-open (Kokai) No. 61-15696), and *Corynebacterium glutamicum* (*Brevibacterium flavum*) AJ12149 (FERM BP-759, U.S. Pat. No. 4,656,135).

<L-Valine-Producing Bacteria>

Examples of methods for imparting, increasing, or enhancing an ability to produce L-valine can include, for example, a method of modifying a bacterium to have an increased activity or activities of one or more of the L-valine biosynthesis enzymes. Examples of such enzymes can include, but are not particularly limited to, the enzymes encoded by the genes of the ilvGMEDA operon and the enzymes encoded by the ilvBNC operon. The ilvBN gene encodes acetohydroxy acid synthase, and the ilvC gene encodes isomeroreductase (WO00/50624). Expressions of the ilvGMEDA operon and the ilvBNC operon are suppressed (attenuated) by L-valine, L-isoleucine, and/or L-leucine. Therefore, to enhance the activity of such an enzyme, the suppression of expression by the produced L-valine can be released by removing or modifying a region required for the attenuation. Furthermore, the threonine deaminase encoded by the ilvA gene catalyzes the deamination reaction of L-threonine resulting 2-ketobutyric acid, which is the rate-limiting step of the L-isoleucine biosynthesis system. Therefore, for L-valine production, the ilvA gene can be, for example, disrupted, and thereby the threonine deaminase activity is decreased.

Examples of methods for imparting, increasing, or enhancing an ability to produce L-valine also can include, for example, a method of modifying a bacterium to have a reduced activity or activities of one or more of the enzymes that catalyze a reaction branching away from the biosynthesis pathway of L-valine to generate a compound other than L-valine. Examples of such enzymes can include, but are not particularly limited to, threonine dehydratase involved in the L-leucine synthesis, and the enzymes involved in the D-pantothenic acid synthesis (WO00/50624).

Specific examples of bacteria able to produce L-valine and parental strains that can be used to derive them can include, for example, *E. coli* strains that have been modified so as to overexpress the ilvGMEDA operon (U.S. Pat. No. 5,998,178).

Examples of bacteria able to produce L-valine and parental strains that can be used to derive them also can include mutant strains having a mutation in amino-acyl t-RNA synthetase (U.S. Pat. No. 5,658,766). Examples of such strains can include, for example, *E. coli* VL1970, which has a mutation in the ileS gene encoding isoleucine t-RNA synthetase. *E. coli* VL1970 was deposited at the Russian National Collection of Industrial Microorganisms (VKPM, FGUP GosNII Genetika, 1 Dorozhny Proezd, 1 Moscow 117545, Russia) on Jun. 24, 1988 under the accession number of VKPM B-4411. Examples of L-valine-producing bacteria and parental strains that can be used to derive them also can include mutant strains requiring lipoic acid for growth and/or lacking HtATPase (WO96/06926).

Examples of L-valine-producing bacteria and parental strains that can be used to derive them also can include strains resistant to an amino acid analogue or the like. Examples of such strains can include, for example, the coryneform bacterium strains which are auxotrophic for L-isoleucine and L-methionine, and resistant to D-ribose, purine ribonucleoside, or pyrimidine ribonucleoside, and have an ability to produce L-valine (FERM P-1841, FERM P-29) (Japanese Patent Publication No. 53-025034), coryneform bacterium strains resistant to polyketides (FERM β-1763, FERM P-1764) (Japanese Patent Publication No. 06-065314), and coryneform bacterium strains resistant to L-valine in a medium containing acetic acid as the sole carbon source and sensitive to pyruvic acid analogues (fluoropyruvic acid etc.) in a medium containing glucose as the sole carbon source (FERM BP-3006, BP-3007) (Japanese Patent No. 3006929).

<L-Alanine-producing bacteria>

Examples of bacteria able to produce L-alanine and parental strains that can be used to derive them can include the coryneform bacteria deficient in the HtATPase (Appl. Microbiol. Biotechnol., 2001 November, 57(4):534-40) and coryneform bacteria in which the aspartate β-decarboxylase activity is enhanced (Japanese Patent Laid-open (Kokai) No. 07-163383).

<L-Tryptophan-Producing Bacteria, L-Phenylalanine-Producing Bacteria, and L-Tyrosine-Producing Bacteria>

Examples of methods for imparting, increasing, or enhancing an ability to produce L-tryptophan, L-phenylalanine, and/or L-tyrosine can include, for example, a method of modifying a bacterium to have an increased activity or activities of one or more of the L-tryptophan, L-phenylalanine, and/or L-tyrosine biosynthesis enzymes.

Examples of enzymes common to the biosynthesis systems of these aromatic amino acids can include, but are not particularly limited to, 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), and chorismate synthase (aroC) (EP763127B). The expressions of the genes encoding these enzymes are controlled by the tyrosine repressor (tyrR), and the activities of these enzymes may be enhanced by deleting the tyrR gene (EP763127B).

Examples of the L-tryptophan biosynthesis enzymes can include, but are not limited to, anthranilate synthase (trpE), tryptophan synthase (trpAB), and phosphoglycerate dehydrogenase (serA). For example, by introducing a DNA containing the tryptophan operon, L-tryptophan-producing ability can be imparted or enhanced. Tryptophan synthase has α and β subunits encoded by the trpA and trpB genes, respectively. Since anthranilate synthase is subject to feedback inhibition by L-tryptophan, the activity of this enzyme can be increased by mutating the gene encoding this enzyme so that the encoded protein is desensitized to feedback inhibition. Since phosphoglycerate dehydrogenase is subject to feedback inhibition by L-serine, the activity of this enzyme can be increased by mutating the gene encoding this enzyme so that the encoded protein is desensitized to feedback inhibition. Furthermore, by increasing the expression of the operon (ace operon) that includes the maleate synthase gene (aceB), isocitrate lyase gene (aceA), and isocitrate dehydrogenase kinase/phosphatase gene (aceK), the ability to produce L-tryptophan may be imparted or enhanced (WO2005/103275).

Examples of the L-phenylalanine biosynthesis enzymes can include, but are not particularly limited to, chorismate mutase and prephenate dehydratase. Chorismate mutase and prephenate dehydratase are encoded by the pheA gene as a bifunctional enzyme. Since the chorismate mutase and prephenate dehydratase are subject to feedback inhibition by L-phenylalanine, the activities of these enzymes may be increased by mutating the genes encoding these enzymes so that the encoded enzymes are desensitized to feedback inhibition.

Examples of the L-tyrosine biosynthesis enzymes can include, but are not particularly limited to, chorismate mutase and prephenate dehydrogenase. The chorismate mutase and prephenate dehydrogenase are encoded by the tyrA gene as a bifunctional enzyme. Since the chorismate mutase and prephenate dehydrogenase are subject to feedback inhibition by L-tyrosine, the activities of these enzymes can be increased by mutating the genes encoding these enzymes so that the encoded enzymes are desensitized to feedback inhibition.

The bacteria that are able to produce L-tryptophan, L-phenylalanine, and/or L-tyrosine may be modified so that biosynthesis of an aromatic amino acid other than the objective aromatic amino acid is reduced. Furthermore, the bacteria able to produce L-tryptophan, L-phenylalanine, and/or L-tyrosine may be modified so that a by-product uptake system is enhanced. Examples of the by-product can include aromatic amino acids other than the objective aromatic amino acid. Examples of the gene encoding such a by-product uptake system can include, for example, tnaB and mtr, which are genes encoding the L-tryptophan uptake system, pheP, which is a gene encoding the L-phenylalanine uptake system, and tyrP, which is a gene encoding the L-tyrosine uptake system (EP1484410).

Specific examples of bacteria able to produce L-tryptophan and parental strains that can be used to derive them can include, for example, E. coli JP4735/pMU3028 (DSM10122) and JP6015/pMU91 (DSM10123), which have a mutant trpS gene encoding a partially inactivated tryptophanyl-tRNA synthetase (U.S. Pat. No. 5,756,345), E. coli SV164, which has a trpE allele encoding an anthranilate synthase desensitized to feedback inhibition by tryptophan, E. coli SV164 (pGH5), which has a serA allele encoding a phosphoglycerate dehydrogenase desensitized to feedback inhibition by serine and a trpE allele encoding an anthranilate synthase desensitized to feedback inhibition by tryptophan (U.S. Pat. No. 6,180,373), a strain introduced with a tryptophan operon containing a trpE allele encoding an anthranilate synthase desensitized to feedback inhibition by tryptophan (Japanese Patent Laid-open (Kokai) Nos. 57-71397 and 62-244382, U.S. Pat. No. 4,371,614), E. coli AGX17(pGX44) (NRRL B-12263) and AGX6(pGX50)aroP (NRRL B-12264), which are deficient tryptophanase (U.S. Pat. No. 4,371,614), E. coli AGX17/pGX50, pACKG4-pps, which has an increased phosphoenolpyruvate-producing ability (WO97/08333, U.S. Pat. No. 6,319,696), and strains belonging to the genus Escherichia having an increased activity of the protein encoded by the yedA or yddG gene (US2003-0148473A1 and US2003-0157667A1).

Examples of coryneform bacteria that are able to produce L-tryptophan can include, for example, Corynebacterium glutamicum AJ12118 (FERM BP-478, Japanese Patent No. 1681002), which is resistant to sulfaguanidine, the strain introduced with the tryptophan operon (Japanese Patent Laid-open (Kokai) No. 63-240794), and the strain introduced with a gene encoding shikimate kinase derived from a coryneform bacterium (Japanese Patent No. 1994749).

Specific examples of bacteria able to produce L-phenylalanine and parental strains that can be used to derive them can include, for example, E. coli AJ12739 (tyrA::Tn10, tyrR) (VKPM B-8197), which is deficient in the chorismate mutase-prephenate dehydrogenase and the tyrosine repressor (WO03/044191), E. coli HW1089 (ATCC 55371), which contains a mutant pheA34 gene encoding a chorismate mutase-prephenate dehydratase desensitized to feedback inhibition (U.S. Pat. No. 5,354,672), E. coli MWEC101-b (KR8903681), E. coli NRRL B-12141, NRRL B-12145, NRRL B-12146, and NRRL B-12147 (U.S. Pat. No. 4,407,952). Specific examples of bacteria able to produce L-phenylalanine and parental strains that can be used to derive them also can include, for example, E. coli K-12<W3110 (tyrA)/pPHAB> (FERM BP-3566), E. coli K-12<W3110 (tyrA)/pPHAD> (FERM BP-12659), E. coli K-12<W3110 (tyrA)/pPHATerm> (FERM BP-12662), and E. coli K-12 AJ12604<W3110(tyrA)/pBR-aroG4, pACMAB> (FERM BP-3579), which contains a gene encoding a chorismate mutase-prephenate dehydratase desensitized to feedback inhibition (EP488424B1). Specific examples of bacteria able to produce L-phenylalanine and parental strains that can be used to derive them further can include, for example, strains belonging to the genus Escherichia having an increased activity of the protein encoded by the yedA gene or the yddG gene (US2003-0148473A, US2003-0157667A, WO03/044192).

Examples of coryneform bacteria able to produce L-phenylalanine can include, for example, the Corynebacterium glutamicum strains BPS-13 (FERM BP-1777), K77 (FERM BP-2062), and K78 (FERM BP-2063) (EP331145A, Japanese Patent Laid-open (Kokai) No. 02-303495), in which phosphoenolpyruvate carboxylase or pyruvate kinase activity is reduced, and the tyrosine-auxotrophic strain (Japanese Patent Laid-open (Kokai) No. 05-049489).

Examples of coryneform bacteria able to produce L-tyrosine can include, for example, Corynebacterium glutamicum AJ11655 (FERM P-5836, Japanese Patent Publication No. 2-6517), and Corynebacterium glutamicum (Brevibacterium lactofermentum) AJ12081 (FERM P-7249, Japanese Patent Laid-open (Kokai) No. 60-70093).

Furthermore, examples of methods for imparting, increasing, or enhancing an ability to produce an L-amino acid can include, for example, a method of modifying a bacterium to have an increased activity for secreting an L-amino acid from a bacterial cell. Such an activity for secreting an L-amino acid can be increased by, for example, increasing the expression of a gene encoding a protein responsible for secretion of the L-amino acid. Examples of genes encoding the proteins responsible for secretion of various amino acids can include, for example, b2682 gene (ygaZ), b2683 gene (ygaH), b1242 gene (ychE), and b3434 gene (yhgN) (Japanese Patent Laid-open (Kokai) No. 2002-300874).

Furthermore, examples of methods for imparting, increasing, or enhancing an ability to produce L-amino acid also can include, for example, a method of modifying a bacterium so that the bacterium has an increased activity or activities of one or more proteins involved in the glycometabolism and proteins involved in the energy metabolism.

Examples of the proteins involved in the glycometabolism can include proteins involved in uptake of saccharides and the glycolysis system enzymes. Examples of genes encoding a protein involved in the glycometabolism can include glucose-6-phosphate isomerase gene (pgi, WO01/02542), pyruvate carboxylase gene (pyc, WO99/18228, EP1092776A), phosphoglucomutase gene (pgm, WO03/04598), fructose bisphosphate aldolase gene (pfkB, fbp, WO03/04664), transaldolase gene (talB, WO03/008611), fumarase gene (fum, WO01/02545), non-PTS sucrose uptake gene (csc, EP1149911A), and sucrose assimilation gene (scrAB operon, U.S. Pat. No. 7,179,623).

Examples of genes encoding the proteins involved in the energy metabolism can include the transhydrogenase gene (pntAB, U.S. Pat. No. 5,830,716) and cytochrome bo-type oxidase gene (cyoB, EP1070376A).

Furthermore, examples of methods for imparting, increasing, or enhancing an ability to produce useful substances such as L-amino acids can include, for example, a method of modifying a bacterium so that the activity of phosphoketolase is increased (WO2006/016705). Hence, the bacterium can also be modified so that the activity of phosphoketolase is increased. This method may be effective particularly for imparting, increasing, or enhancing an ability to produce an L-amino acid of glutamate family such as L-glutamic acid. Examples of phosphoketolase can include D-xylulose-5-phosphate phosphoketolase and fructose-6-phosphate phosphoketolase. Either one of the D-xylulose-5-phosphate phosphoketolase activity and the fructose-6-phosphate phosphoketolase activity may be enhanced, or both may be enhanced.

The term "D-xylulose-5-phosphate phosphoketolase activity" can refer to an activity for converting xylulose-5-phosphate into glycelaldehyde-3-phosphate and acetyl phosphate with consuming phosphoric acid to release one molecule of $H_2O$. This activity can be measured by the method described by Goldberg, M. et al. (Methods Enzymol., 9, 515-520, 1996) or the method described by L. Meile (J. Bacteriol., 183:2929-2936, 2001). Examples of D-xylulose-5-phosphate phosphoketolase can include those of bacteria belonging to the genera *Acetobacter, Bifidobacterium, Lactobacillus, Thiobacillus, Streptococcus, Methylococcus, Butyrivibrio*, and *Fibrobacter*, and yeast belonging to the genera *Candida, Rhodotorula, Rhodosporidium, Pichia, Yarrowia, Hansenula, Kluyveromyces, Saccharomyces, Trichosporon*, and *Wingea*. Specific examples of D-xylulose-5-phosphate phosphoketolase and genes encoding them are disclosed in WO2006/016705.

The term "fructose-6-phosphate phosphoketolase activity" can refer to the activity of converting fructose-6-phosphate into erythrose-4-phosphate and acetyl phosphate while consuming phosphoric acid to release one molecule of $H_2O$. This activity can be measured by the method described by Racker, E. (Methods Enzymol., 5, 276-280, 1962) or the method described by L. Meile (J. Bacteriol., 183:2929-2936, 2001). Examples of fructose-6-phosphate phosphoketolase can include enzymes of bacteria belonging to the genera *Acetobacter, Bifidobacterium, Chlorobium, Brucella, Methylococcus*, and *Gardnerella*, and yeast belonging to the genera *Rhodotorula, Candida*, and *Saccharomyces*. Specific examples of fructose-6-phosphate phosphoketolase and genes encoding them are disclosed in WO2006/016705.

Both the D-xylulose-5-phosphate phosphoketolase activity and the fructose-6-phosphate phosphoketolase activity may also be retained by a single enzyme, for example, D-xylulose-5-phosphate phosphoketolase/fructose-6-phosphate phosphoketolase.

The nucleotide sequence of the phosphoketolase gene (xfp gene) of *Bifidobacterium longum* JCM1217 and the amino acid sequence of the phosphoketolase encoded by the gene (Xfp protein) are shown in SEQ ID NOS: 13 and 14, respectively.

The genes and proteins used for breeding bacteria able to produce L-amino acids may have, for example, the nucleotide sequences and amino acid sequences of known genes and proteins, such as those exemplified above, respectively. Also, the genes and proteins used for breeding bacteria able to produce L-amino acid may be conservative variants of known genes and proteins, such as those exemplified above, respectively. Specifically, for example, the genes used for breeding bacteria able to produce L-amino acid may each encode a protein having an amino acid sequence of a known protein, but can include substitution, deletion, insertion, or addition of one or several amino acid residues at one or several positions, so long as the original function of the encoded protein is maintained. For conservative variants of genes and proteins, the descriptions concerning conservative variants of the non-PTS fructose-uptake carrier and fructokinase and genes encoding them mentioned later can be applied, mutatis mutandis.

<1-2> Enhancement of Non-PTS Fructose-Uptake Carrier Activity and Fructokinase Activity The bacterium can be modified so that the activity of a non-PTS fructose-uptake carrier and the activity of fructokinase are increased. The bacterium can be modified specifically so that the activity of a non-PTS fructose-uptake carrier and the activity of fructokinase are increased as compared with a non-modified strain. The bacterium can be obtained by modifying a bacterium having an L-amino acid-producing ability so that the activity of a non-PTS fructose-uptake carrier and the activity of fructokinase are increased. The bacterium can also be obtained by modifying a bacterium so that the activity of a non-PTS fructose-uptake carrier and the activity of fructokinase are increased, and then imparting, increasing, or enhancing the ability to produce L-amino acid. The bacterium may also have acquired the ability to produce L-amino acid by being modified so that the activity of a non-PTS fructose-uptake carrier and the activity of fructokinase are increased. The bacterium can have, as required, such a property possessed by an L-amino acid-producing bacterium as mentioned above, as well as being modified so that the activity of a non-PTS fructose-uptake carrier and the activity of fructokinase are increased. For example, the bacterium can be modified so that the activity of phosphoketolase is increased. For example, particularly, in *Pantoea* bacteria, a combination of enhancement of the activity of a non-PTS fructose-uptake carrier and the activity of fructokinase with enhancement of the activity of phosphoketolase, such as introduction of xfp gene, can result in a synergistic improvement in L-glutamic acid production. The modifications for constructing the bacterium can be performed in an arbitrary order.

By modifying a bacterium so that the activity of a non-PTS fructose-uptake carrier and the activity of fructokinase are increased, the ability of the bacterium to produce L-amino acids can be improved, and that is, production of an L-amino acid by using the bacterium can be increased. Particularly, by modifying a bacterium so that the activity of a non-PTS fructose-uptake carrier and the activity of fructokinase are increased, an L-amino acid-producing ability of the bacterium under conditions of using fructose as a carbon source can be improved, and that is, production of an L-amino acid by using the bacterium can be increased.

Hereinafter, the non-PTS fructose-uptake carrier and fructokinase, and genes encoding them will be explained.

The term "non-PTS fructose-uptake carrier" can refer to a protein having non-PTS fructose-uptake activity. The term "non-PTS fructose-uptake activity" can refer to an activity to uptake fructose from outside of a cell to inside of the cell not via the Phosphotransferase System (PTS). The term "Phosphotransferase System (PTS)" can refer to a saccharide-uptake system that takes up a saccharide while phosphorylating it. For example, fructose is taken up via PTS in the form of fructose-1-phosphate. That is, the term "non-PTS fructose-uptake activity" may refer to, specifically, an activity to uptake fructose from outside of a cell to inside of the cell without phosphorylating fructose, or more specifically, an activity to uptake fructose from outside of a cell to inside of the cell without phosphorylating the Pt position of fructose. A gene encoding a non-PTS fructose-uptake carrier can also be referred to as "non-PTS fructose-uptake carrier gene".

Examples of the non-PTS fructose-uptake carrier gene can include the fucP gene. A protein (non-PTS fructose-uptake carrier) encoded by fucP gene can also be referred to as "FucP protein". The FucP protein is known as an L-fucose permease, which is a fucose-uptake carrier, while it also has fructose-uptake activity. The activity of a non-PTS fructose-uptake carrier can be increased by, for example, increasing the expression of a non-PTS fructose-uptake carrier gene. That is, the expression "the activity of a non-PTS fructose-uptake carrier is increased" may mean that, for example, the expression of a non-PTS fructose-uptake carrier gene is increased. The expression "the activity of a non-PTS fructose-uptake carrier is increased" may also mean that, specifically, for example, the expression of fucP gene is increased.

The term "fructokinase" can refer to a protein having fructokinase activity. The term "fructokinase activity" refers to an activity of catalyzing the reaction of phosphorylating 6th position of fructose to generate fructose-6-phosphate (EC 2.7.1.4). Phosphate group-donors such as ATP can be used for phosphorylation of fructose by fructokinase. A gene encoding fructokinase can also be referred to as "fructokinase gene".

Examples of the fructokinase gene can include frk gene. The frk gene can also be referred to as the mak gene, scrK gene, sacK gene, cscK gene, etc. A protein (fructokinase) encoded by frk gene can also be referred to as a "Frk protein". The activity of fructokinase can be increased by, for example, increasing the expression of a fructokinase gene. That is, the expression "the activity of fructokinase is increased" may mean that, for example, the expression of a fructokinase gene is increased. The expression "the activity of fructokinase is increased" may also mean that, specifically, for example, the expression of frk gene is increased.

Examples of the non-PTS fructose-uptake carrier gene and fructokinase gene can include genes of various organisms such as bacteria belonging to the family Enterobacteriaceae, coryneform bacteria, and lactic acid bacteria. The nucleotide sequences of the non-PTS fructose-uptake carrier genes and fructokinase genes derived from various organisms and the amino acid sequences of the non-PTS fructose-uptake carriers and fructokinases encoded thereby can be obtained from, for example, public databases such as NCBI. Specific examples of fucP gene can include, for example, the fucP gene of *Corynebacterium ammoniagenes* and the fucP gene of *Pantoea ananatis*. The nucleotide sequence of the fucP gene of *C. ammoniagenes* ATCC 6872 and the amino acid sequence of the protein encoded by the gene are shown in SEQ ID NOS: 26 and 27, respectively. The nucleotide sequence of the fucP gene of *P. ananatis* AJ13355 and the amino acid sequence of the protein encoded by the gene are shown in SEQ ID NOS: 28 and 29, respectively. Specific examples of frk gene can include, for example, frk gene of *Bifidobacterium longum* and frk (mak) and frk (scrK) genes of *Pantoea ananatis*. The nucleotide sequence of the frk gene of *B. longum* JCM1217 and the amino acid sequence of the protein encoded by the gene are shown in SEQ ID NOS: 30 and 31, respectively. The nucleotide sequence of the frk (mak) gene of *P. ananatis* AJ13355 and the amino acid sequence of the protein encoded by the gene are shown in SEQ ID NOS: 32 and 33, respectively. The nucleotide sequence of the frk (scrK) gene of *P. ananatis* AJ13355 and the amino acid sequence of the protein encoded by the gene are shown in SEQ ID NOS: 34 and 35, respectively. That is, the non-PTS fructose-uptake carrier gene may be, for example, a gene having the nucleotide sequence of any of the non-PTS fructose-uptake carrier genes exemplified above, such as the nucleotide sequence shown as SEQ ID NO: 26 or 28. Also, the non-PTS fructose-uptake carrier may be, for example, a protein having the amino acid sequence of any of the non-PTS fructose-uptake carriers exemplified above, such as the amino acid sequence shown as SEQ ID NO: 27 or 29. Also, the fructokinase gene may be, for example, a gene having the nucleotide sequence of any of the fructokinase genes exemplified above, such as the nucleotide sequence shown as SEQ ID NO: 30, 32, or 34. Also, fructokinase may be, for example, a protein having the amino acid sequence of any of the fructokinases exemplified above, such as the amino acid sequence shown as SEQ ID NO: 31, 33, or 35. The expression "a gene or protein has a nucleotide or amino acid sequence" can mean that the gene or protein includes the nucleotide or amino acid sequence unless otherwise stated, and also can mean gene or protein includes only the nucleotide or amino acid sequence.

The non-PTS fructose-uptake carrier gene may be a variant of any of the non-PTS fructose-uptake carrier genes exemplified above, that is, a gene having the nucleotide sequence shown as SEQ ID NO: 26 or 28, so long as the original function thereof is maintained. Similarly, the non-PTS fructose-uptake carrier may be a variant of any of the non-PTS fructose-uptake carriers exemplified above (e.g. a protein having the amino acid sequence shown as SEQ ID NO: 27 or 29), so long as the original function thereof is maintained. Also, the fructokinase gene may be a variant of any of the fructokinase genes exemplified above, that is, a gene having the nucleotide sequence shown as SEQ ID NO: 30, 32, or 34, so long as the original function thereof is maintained. Similarly, fructokinase may be a variant of any of the fructokinases exemplified above, that is, a protein having the amino acid sequence shown as SEQ ID NO: 31, 33, or 35, so long as the original function thereof is maintained. Such a variant that maintains the original function thereof can also be referred to as a "conservative variant". The terms "fucP gene" and "frk gene" can include not only the fucP genes and frk genes exemplified above, respectively, but also can include conservative variants thereof. Similarly, the terms "FucP protein" and "Frk protein" can include not only the FucP proteins and Frk proteins exemplified above, respectively, but also can include conservative variants thereof. Examples of the conservative variants can include, for example, homologues and artificially modified versions of the non-PTS fructose-uptake carrier genes, fructokinase genes, non-PTS fructose-uptake carriers, and fructokinases exemplified above.

The expression "the original function is maintained" can mean that a variant of gene or protein has a function (such as activity or property) corresponding to the function (such as activity or property) of the original gene or protein. The expression "the original function is maintained" in relation to a gene can mean that a variant of the gene encodes a protein that maintains the original function. That is, the expression "the original function is maintained" in relation to the non-PTS fructose-uptake carrier gene can mean that a variant of the gene encodes a protein having non-PTS fructose-uptake activity. Furthermore, the expression "the original function is maintained" in relation to the non-PTS fructose-uptake carrier can mean that a variant of the protein has non-PTS fructose-uptake activity. Also, the expression "the original function is maintained" in relation to the fructokinase gene can mean that a variant of the gene encodes a protein having fructokinase activity. Furthermore, the expression "the original function is maintained" in relation to fructokinase can mean that a variant of the protein has fructokinase activity.

The non-PTS fructose-uptake activity of a protein can be measured by, for example, incubating bacterial cells expressing the protein with fructose, and measuring the protein-dependent uptake of fructose into the cells.

The fructokinase activity of a protein can be measured by, for example, incubating the protein with the substrate, such as fructose, in the presence of ATP, and measuring the protein- and substrate-dependent generation of fructose-6-phosphate.

Hereinafter, examples of the conservative variants will be explained.

Homologues of the non-PTS fructose-uptake carrier genes or fructokinase genes or homologues of the non-PTS fructose-uptake carriers or fructokinases can be easily obtained from public databases by, for example, a BLAST search or FASTA search using any of the nucleotide sequences of the non-PTS fructose-uptake carrier genes or fructokinase genes exemplified above or any of the amino acid sequences of the non-PTS fructose-uptake carriers or fructokinases exemplified above as a query sequence. Furthermore, homologues of the non-PTS fructose-uptake carrier genes or fructokinase genes can be obtained by, for example, PCR using a chromosome of various organisms as the template, and oligonucleotides prepared on the basis of any of the nucleotide sequences of these known non-PTS fructose-uptake carrier genes or fructokinase genes as primers.

The non-PTS fructose-uptake carrier gene or fructokinase gene may be a gene encoding a protein having any of the aforementioned amino acid sequences, that is, the amino acid sequence shown as SEQ ID NO: 27 or 29 for the non-PTS fructose-uptake carrier, or the amino acid sequence shown as SEQ ID NO: 31, 33, or 35 for fructokinase, but which can include substitution, deletion, insertion, and/or addition of one or several amino acid residues at one or several positions, so long as the original function is maintained. For example, the N-terminus and/or the C-terminus of the encoded protein may be elongated or shortened. Although the number meant by the term "one or several" may differ depending on the positions of amino acid residues in the three-dimensional structure of the protein or the types of amino acid residues, specifically, it is, for example, 1 to 50, 1 to 40, 1 to 30, 1 to 20, 1 to 10, 1 to 5, or 1 to 3.

The aforementioned substitution, deletion, insertion, and/or addition of one or several amino acid residues can be a conservative mutation that maintains the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions can include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, or addition of amino acid residues as mentioned above can include a naturally occurring mutation due to an individual difference, or a difference of species of the organism from which the gene is derived (mutant or variant).

The non-PTS fructose-uptake carrier gene or fructokinase gene may be a gene encoding a protein having an amino acid sequence having a homology of, for example, 50% or more, 65% or more, or 80% or more, 90% or more, 95% or more, 97% or more, or 99% or more, to the total amino acid sequence of any of the aforementioned amino acid sequences, so long as the original function is maintained. In this description, "homology" means "identity".

The non-PTS fructose-uptake carrier gene or fructokinase gene may also be a DNA that is able to hybridize under stringent conditions with a probe that can be prepared from any of the aforementioned nucleotide sequences, that is, the nucleotide sequence shown as SEQ ID NO: 26 or 28 for the non-PTS fructose-uptake carrier gene, or the nucleotide sequence shown as SEQ ID NO: 30, 32, or 34 for the fructokinase gene, such as a sequence complementary to a partial or entire sequence of any of the aforementioned nucleotide sequences, so long as the original function is maintained. The term "stringent conditions" can refer to conditions under which a so-called specific hybrid is formed, and a non-specific hybrid is not formed. Examples of stringent conditions can include those under which highly homologous DNAs hybridize to each other, for example, DNAs not less than 50%, 65%, 80%, 90%, 95%, 97%, 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C.; 0.1×SSC, 0.1% SDS at 60° C.; or 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing any of the aforementioned genes as a template. As the probe, for example, a DNA fragment having a length of about 300 bp can be used. When a DNA fragment having a length of about 300 bp is used as the probe, the washing conditions of the hybridization may be, for example, 50° C., 2×SSC and 0.1% SDS.

Furthermore, since the degeneracy of codons differs depending on the host, arbitrary codons in the non-PTS fructose-uptake carrier gene or fructokinase gene may be replaced with respective equivalent codons. That is, the non-PTS fructose-uptake carrier gene or fructokinase gene may be a variant of any of the non-PTS fructose-uptake carrier genes or fructokinase genes exemplified above due to the degeneracy of the genetic code. For example, the non-PTS fructose-uptake carrier gene or fructokinase gene may be a gene modified so that it has optimal codons according to codon frequencies in a host to be used.

The percentage of the sequence identity between two sequences can be determined by, for example, using a mathematical algorithm. Non-limiting examples of such a mathematical algorithm include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison, for example, alignment, for determining the sequence identity can be performed. The program can be appropriately executed by a computer. Examples of such a program can include, but are not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program, that is, BLASTN for nucleotide sequences, and BLASTX for amino acid sequences, can be used. Alignment can also be manually performed.

The sequence identity between two sequences is calculated as the ratio of residues matching in the two sequences when aligning the two sequences so as to fit maximally with each other.

The aforementioned descriptions concerning conservative variants of the genes and proteins can be applied mutatis mutandis to variants of arbitrary proteins such as L-amino acid biosynthesis system enzymes and genes encoding them.

<1-3> Methods for Increasing Activity of Protein

Hereinafter, the methods for increasing the activity of a protein such as the non-PTS fructose-uptake carrier and fructokinase will be explained.

The expression "the activity of a protein is increased" can mean that the activity of the protein is increased as compared with a non-modified strain. Specifically, the expression "the activity of a protein is increased" can mean that the activity of the protein per cell is increased as compared with that of a non-modified strain. The term "non-modified strain" can refer to a control strain that has not been modified so that the activity of an objective protein is increased. Examples of the non-modified strain can include a wild-type strain and parental strain. Specific examples of the non-modified strain can include strains that are the same as the species of the modified bacteria. Specific examples of the non-modified strain can also include strains exemplified above in relation to the description of modified bacteria. That is, in an embodiment, the activity of a protein may be increased as compared with a non-modified strain which is the same strain as that that was modified to make the objective modified bacteria. In another embodiment, the activity of a protein may also be increased as compared with the *C. glutamicum* ATCC 13032 strain. In another embodiment, the activity of a protein may also be increased as compared with the *C. glutamicum* 2256 strain (ATCC 13869). In another embodiment, the activity of a protein may also be increased as compared with the *E. coli* K-12 MG1655 strain. The state that "the activity of a protein is increased" may also be expressed as "the activity of a protein is enhanced". More specifically, the expression "the activity of a protein is increased" may mean that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene (i.e. the amount of mRNA) encoding the protein, or the translation amount of the gene (i.e. the amount of the protein). Furthermore, the state that "the activity of a protein is increased" can include not only a when the activity of an objective protein is increased in a strain inherently having the activity of the objective protein, but also when the activity of an objective protein is imparted to a strain that does not inherently have the activity of the objective protein. Furthermore, so long as the activity of the protein is eventually increased, the activity of an objective protein inherently present in a host may be attenuated and/or eliminated, and then an appropriate type of the objective protein may be imparted to the host.

The degree of the increase in the activity of a protein is not particularly limited, so long as the activity of the protein is increased as compared with a non-modified strain. The activity of the protein may be increased to, for example, 1.5 times or more, 2 times or more, or 3 times or more of that of a non-modified strain. Furthermore, when the non-modified strain does not have the activity of the objective protein, it is sufficient that the protein is produced as a result of introduction of the gene encoding the protein, and for example, the protein may be produced to such an extent that the activity thereof can be measured.

The modification for increasing the activity of a protein can be attained by, for example, increasing the expression of a gene encoding the protein. The phrase "the expression of a gene is increased" can mean that the expression of the gene is increased as compared with a non-modified strain such as a wild-type strain or a parental strain. Specifically, the phrase "the expression of a gene is increased" can mean that the expression amount of the gene per cell is increased as compared with that of a non-modified strain. More specifically, the phrase "the expression of a gene is increased" may mean that the transcription amount of the gene (i.e. the amount of mRNA) is increased, and/or the translation amount of the gene (i.e. the amount of the protein expressed from the gene) is increased. The state that "the expression of a gene is increased" may also be referred to as "the expression of a gene is enhanced". The expression of a gene may be increased to, for example, 1.5 times or more, 2 times or more, or 3 times or more of that of a non-modified strain. Furthermore, the state that "the expression of a gene is increased" can include not only when the expression amount of an objective gene is increased in a strain that inherently expresses the objective gene, but also when the gene is introduced into a strain that does not inherently express the objective gene, and expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination can include, for example, a method of using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome can include repetitive DNAs, and inverted repeats located at the both ends of a transposon. Alternatively, homologous recombination may be performed by using an appropriate sequence on a chromosome such as a gene unnecessary for production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP805867B1).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector can be a multi-copy vector. Furthermore, the vector can have a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in Enterobacteriaceae bacteria such as *Escherichia coli* can include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pCold TF DNA (Takara Bio), pACYC series vectors, and the broad host spectrum vector RSF1010. Specific examples of vector autonomously replicable in coryneform bacteria can include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 (Japanese Patent Laid-open (Kokai) No. 3-210184); plasmids pCRY21, pCRY2KE, pCRY2KX, pCRY31, pCRY3KE, and pCRY3KX (Japanese Patent Laid-open (Kokai) No. 2-72876 and U.S. Pat. No. 5,185,262); plasmids pCRY2 and pCRY3 (Japanese Patent Laid-open (Kokai) No. 1-191686); pAJ655, pAJ611, and pAJ1844 (Japanese Patent Laid-open (Kokai) No. 58-192900); pCG1 (Japanese Patent Laid-open (Kokai) No. 57-134500); pCG2 (Japanese Patent Laid-open (Kokai) No. 58-35197); pCG4 and pCG11 (Japanese Patent Laid-open (Kokai) No. 57-183799); pVK7 (Japanese Patent Laid-open (Kokai) No. 10-215883); pVK9 (US2006-0141588); pVC7 (Japanese Patent Laid-open (Kokai) No. 9-070291); pVS7 (WO2013/069634).

When a gene is introduced, it is sufficient that the gene is expressibly harbored by a host. Specifically, it is sufficient that the gene is harbored by a host so that it is expressed under control by a promoter that functions in the host. The promoter is not particularly limited so long as it functions in the host. The term "promoter that functions in a host" can refer to a promoter that shows a promoter activity in the host. The promoter may be a promoter derived from the host, or a heterogenous promoter. The promoter may be the native promoter of the gene to be introduced, or a promoter of another gene. As the promoter, for example, such a stronger promoter as mentioned later may also be used.

A terminator for termination of gene transcription may be located downstream of the gene. The terminator is not particularly limited so long as it functions in the host. The terminator may be a terminator derived from the host, or a heterogenous terminator. The terminator may be the native terminator of the gene to be introduced, or a terminator of another gene. Specific examples of the terminator can include, for example, T7 terminator, T4 terminator, fd phage terminator, tet terminator, and trpA terminator.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Furthermore, when two or more of genes are introduced, it is sufficient that the genes each are expressibly harbored by the host. For example, all the genes may be carried by a single expression vector or a chromosome. Furthermore, the genes may be separately carried by two or more expression vectors, or separately carried by a single or two or more expression vectors and a chromosome. An operon constituted by two or more genes may also be introduced. The phrase "introducing two or more genes" can include, for example, introducing genes encoding two or more kinds of proteins, such as enzymes, introducing genes encoding two or more subunits constituting a single protein complex, such as enzyme complex, and a combination of these.

The gene to be introduced is not particularly limited so long as it encodes a protein that functions in the host. The gene to be introduced may be a gene native to the host, that is, homologous to the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene (Gene, 60(1), 115-127 (1987)). The obtained gene can be used as it is, or after being modified as required. That is, a gene can be modified to obtain a variant thereof. A gene can be modified by a known technique. For example, an objective mutation can be introduced into an objective site of DNA by the site-specific mutation method. That is, the coding region of a gene can be modified by the site-specific mutation method so that a specific site of the encoded protein can include substitution, deletion, insertion, and/or addition of amino acid residues. Examples of the site-specific mutation method can include the method utilizing PCR (Higuchi, R., 61, in PCR Technology, Erlich, H. A. Eds., Stockton Press (1989); Carter, P., Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a variant of a gene may be totally synthesized.

Incidentally, when a protein functions as a complex made up of a plurality of subunits, some or all of the subunits may be modified, so long as the activity of the protein is eventually increased. That is, for example, when the activity of a protein is increased by increasing the expression of a gene, the expression of some or all of the genes that encode the subunits may be enhanced. It is usually preferable to enhance the expression of all of the genes encoding the subunits. Furthermore, the subunits making up the complex may be native to a single kind of organism or two or more kinds of organisms, so long as the complex has a function of the objective protein. That is, for example, genes of the same organism encoding a plurality of subunits may be introduced into a host, or genes of different organisms encoding a plurality of subunits may be introduced into a host.

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively can refer to sites that affect the expression of a gene. Examples of the expression control sequence can include, for example, a promoter, Shine-Dalgarno (SD) sequence (also referred to as ribosome binding site (RBS)), and spacer region between RBS and the start codon. Expression control sequences can be identified by using a promoter search vector or gene analysis software such as GENETYX. These expression control sequences can be modified by, for example, a method of using a temperature sensitive vector, or the Red driven integration method (WO2005/010175).

The transcription efficiency of a gene can be improved by, for example, replacing the promoter of the gene on a chromosome with a stronger promoter. The term "stronger promoter" can refer to a promoter providing an improved transcription of a gene compared with an inherent wild-type promoter of the gene. Examples of stronger promoters can include, for example, the known high expression promoters such as T7 promoter, trp promoter, lac promoter, thr promoter, tac promoter, trc promoter, tet promoter, araBAD promoter, rpoH promoter, msrA promoter, Pm1 promoter (derived from the genus *Bifidobacterium*), PR promoter, and PL promoter. Examples of stronger promoters usable in coryneform bacteria can include, for example, the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 December; 71 (12):8587-96), as well as lac promoter, tac promoter, and trc promoter. Furthermore, as the stronger promoter, a highly-active inherent promoter may also be obtained by using various reporter genes. For example, by making the −35 and −10 regions in a promoter region closer to the consensus sequence, the activity of the promoter can be enhanced (WO00/18935). Examples of highly active-type promoter can include various tac-like promoters (Katashkina J I et al., Russian Federation Patent Application No. 2006134574) and pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" can mean a SD sequence that provides an improved translation of mRNA compared with the inherent wild-type SD sequence of the gene. Examples of stronger SD sequences can include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying them.

The translation efficiency of a gene can also be improved by, for example, modifying codons. For example, the translation efficiency of the gene can be improved by replacing a rare codon present in the gene with a synonymous codon that is more frequently used. That is, the gene to be introduced may be modified, for example, so as to contain optimal codons according to the frequencies of codons observed in the chosen host. Codons can be replaced by, for example, the site-specific mutation method. Alternatively, a gene fragment in which objective codons are replaced may be totally synthesized. Frequencies of codons in various organisms are disclosed in the "Codon Usage Database" (kazusa.or.jp/codon; Nakamura, Y. et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

Furthermore, the modification that increases the activity of a protein can also be attained by, for example, enhancing the specific activity of the enzyme. Enhancement of the specific activity also can include desensitization to feedback inhibition. That is, when a protein is subject to feedback inhibition by a metabolite, the activity of the protein can be increased by making the bacterium harbor a gene encoding a mutant protein that has been desensitized to the feedback inhibition. The phrase "desensitization to feedback inhibition" can include complete elimination of the feedback inhibition, and attenuation of the feedback inhibition, unless otherwise stated. Also, a state of "being desensitized to feedback inhibition", for example, a state that feedback inhibition is eliminated or attenuated, may also be referred to as "tolerant to feedback inhibition". A protein showing an enhanced specific activity can be obtained by, for example, searching various organisms. Furthermore, a highly-active type of an existing protein may also be obtained by introducing a mutation into the existing protein. The mutation to be introduced may be, for example, substitution, deletion, insertion, or addition of one or several amino acid residues at one or several positions of the protein. The mutation can be introduced by, for example, such a site-specific mutation method as mentioned above. The mutation may also be introduced by, for example, a mutagenesis treatment. Examples of the mutagenesis treatment can include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Furthermore, a random mutation may be induced by directly treating DNA in vitro with hydroxylamine. Enhancement of the specific activity may be independently used, or may be used in an arbitrary combination with such methods for enhancing gene expression as mentioned above.

The method for the transformation is not particularly limited, and can include conventionally known methods. Such methods can include, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternatively, such methods also can include a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Furthermore, the electric pulse method reported for coryneform bacteria (Japanese Patent Laid-open (Kokai) No. 2-207791) can also be used.

An increase in the activity of a protein can be confirmed by measuring the activity of the protein.

An increase in the activity of a protein can also be confirmed by confirming an increase in the expression of a gene encoding the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA can include Northern hybridization, RT-PCR, microarray, RNA-seq, and so forth (Sambrook, J., et al., Molecular Cloning A Laboratory Manual/Third Edition, Cold Spring Harbor Laboratory Press, Cold Spring Harbor (USA), 2001). The amount of mRNA may increase to, for example, 1.5 times or more, 2 times or more, or 3 times or more of that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein, such as the number of molecules of the protein per cell, may increase to, for example, 1.5 times or more, 2 times or more, or 3 times or more of that of a non-modified strain.

The aforementioned methods for increasing the activity of a protein can be used for enhancement of the activities of arbitrary proteins such as L-amino acid biosynthesis enzymes, and enhancement of the expression of arbitrary genes such as genes encoding those arbitrary proteins, besides enhancement of non-PTS fructose-uptake carrier activity and fructokinase activity.

<1-4> Method for Reducing Activity of Protein

Hereinafter, the methods for reducing the activity of a protein will be described.

The expression "the activity of a protein is reduced" can mean that the activity of the protein is reduced as compared with a non-modified strain. Specifically, the expression "the activity of a protein is reduced" can mean that the activity of the protein per cell is reduced as compared with that of a non-modified strain. The term "non-modified strain" can refer to a control strain that has not been modified so that the activity of an objective protein is reduced. Examples of the non-modified strain can include a wild-type strain and parental strain. Specific examples of the non-modified strain can include the same strain of the species of bacteria chosen to be modified. Specific examples of the non-modified strain also can include strains exemplified above in relation to the description of bacteria. That is, in an embodiment, the activity of a protein may be reduced as compared with same strain as the chosen bacterium to be modified. In another embodiment, the activity of a protein may also be reduced as compared with the *C. glutamicum* ATCC 13032 strain. In another embodiment, the activity of a protein may also be reduced as compared with the *C. glutamicum* 2256 strain (ATCC 13869). In another embodiment, the activity of a protein may also be reduced as compared with the *E. coli* K-12 MG1655 strain. The state that "the activity of a protein is reduced" also can include when the activity of the protein has completely disappeared. More specifically, the expression "the activity of a protein is reduced" may mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the gene (i.e. the amount of the protein). The state that "the number of molecules of the protein per cell is reduced" also can include a state that the protein does not exist at all. The state that "the function of each molecule of the protein is reduced" also can include a state that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The phrase "the expression of a gene is reduced" can mean that the expression of the gene is reduced as compared with a non-modified strain such as a wild-type strain and parental strain. Specifically, the phrase "the expression of a gene is reduced" can mean that the expression of the gene per cell is reduced as compared with that of a non-modified strain. More specifically, the phrase "the expression of a gene is reduced" may mean that the transcription amount of the gene (i.e. the amount of mRNA) is reduced, and/or the translation amount of the gene (i.e. the amount of the protein expressed from the gene) is reduced. The state that "the expression of a gene is reduced" also can include a state that the gene is not expressed at all. The state that "the expression of a gene is reduced" can also be referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as a promoter, Shine-Dalgarno (SD) sequence (also referred to as ribosome-binding site (RBS)), and spacer region between RBS and the start codon of the gene. When an expression control sequence is modified, one or more nucleotides, two or more nucleotides, three or more nucleotides, of the expression control sequence are modified. For example, the transcription efficiency of a gene can be reduced by, for example, replacing the promoter of the gene on a chromosome with a weaker promoter. The term "weaker promoter" can mean a promoter providing an attenuated transcription of a gene compared with an inherent wild-type promoter of the gene. Examples of weaker promoters can include, for example, inducible promoters. That is, an inducible promoter may function as a weaker promoter under a non-induced condition, such as in the absence of the corresponding inducer. Furthermore, a part or the whole of an expression control sequence may be deleted. The expression of a gene can also be reduced by, for example, manipulating a factor responsible for expression control. Examples of the factor responsible for expression control can include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. The expression "a gene is disrupted" can mean that a gene is modified so that a protein that can normally function is not produced. The state that "a protein that normally functions is not produced" can include a state that the protein is not produced at all from the gene, and a state that the protein of which the function (such as activity or property) per molecule is reduced or eliminated is produced from the gene.

Disruption of a gene can be attained by, for example, deleting the gene on a chromosome. The term "deletion of a gene" can refer to deletion of a partial or entire region of the coding region of the gene. Furthermore, the entire gene including sequences upstream and downstream from the coding region of the gene on a chromosome may be deleted. The region to be deleted may be any region such as an N-terminal region (region encoding an N-terminal region of a protein), an internal region, or a C-terminal region (region encoding a C-terminal region of a protein), so long as the activity of the protein can be reduced. Deletion of a longer region can usually more surely inactivate the gene. The region to be deleted may be, for example, a region having a length of 10% or more, 20% or more, 30% or more, 40% or more, 50% or more, 60% or more, 70% or more, 80% or more, 90% or more, or 95% or more of the total length of the coding region of the gene. Furthermore, it is preferred that reading frames of the sequences upstream and downstream from the region to be deleted are not the same. Inconsistency of reading frames may cause a frameshift downstream of the region to be deleted.

Disruption of a gene can also be attained by, for example, introducing a mutation for an amino acid substitution (missense mutation), a stop codon (nonsense mutation), addition or deletion of one or two nucleotide residues (frame shift mutation), or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another nucleotide sequence into a coding region of the gene on a chromosome. Site of the insertion may be in any region of the gene, and insertion of a longer nucleotide sequence can usually more surely inactivate the gene. It is preferred that reading frames of the sequences upstream and downstream from the insertion site are not the same. Inconsistency of reading frames may cause a frameshift downstream of the region to be deleted. The other nucleotide sequence is not particularly limited so long as a sequence that reduces or eliminates the activity of the encoded protein is chosen, and examples thereof can include, for example, a marker gene such as antibiotic resistance genes, and a gene useful for production of an objective substance.

Particularly, disruption of a gene may be carried out so that the amino acid sequence of the encoded protein is deleted. In other words, the modification for reducing the activity of a protein can be attained by, for example, deleting the amino acid sequence of the protein, specifically, modifying a gene so as to encode a protein of which the amino acid sequence is deleted. The term "deletion of the amino acid sequence of a protein" can refer to deletion of a partial or entire region of the amino acid sequence of the protein. In addition, the term "deletion of the amino acid sequence of a protein" can mean that the original amino acid sequence disappears in the protein, and also can include cases where the original amino acid sequence is changed to another amino acid sequence. That is, for example, a region that was changed to another amino acid sequence by frameshift may be regarded as a deleted region. When the amino acid sequence of a protein is deleted, the total length of the protein is typically shortened, but there can also be cases where the total length of the protein is not changed or is extended. For example, by deletion of a partial or entire region of the coding region of a gene, a region encoded by the deleted region can be deleted in the encoded protein. In addition, for example, by introduction of a stop codon into the coding region of a gene, a region encoded by the downstream region of the introduction site can be deleted in the encoded protein. In addition, for example, by frameshift in the coding region of a gene, a region encoded by the frameshift region can be deleted in the encoded protein. The aforementioned descriptions concerning the position and length of the region to be deleted in deletion of a gene can be applied mutatis mutandis to the position and length of the region to be deleted in deletion of the amino acid sequence of a protein.

Such modification of a gene on a chromosome as described above can be attained by, for example, preparing a disruption-type gene modified so that it is unable to produce a protein that normally functions, and transforming a host with a recombinant DNA containing the disruption-type gene to cause homologous recombination between the disruption-type gene and the wild-type gene on a chromosome and thereby substitute the disruption-type gene for the wild-type gene on the chromosome. In this procedure, if a marker gene selected according to the characteristics of the host such as auxotrophy is included in the recombinant DNA, the operation becomes easier. Examples of the disruption-type gene can include a gene of which a partial or entire region of the coding region is deleted, gene including a missense mutation, gene including a nonsense mutation, gene including a frame shift mutation, and gene introduced with an insertion sequence such as a transposon or marker gene. The protein encoded by the disruption-type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

The modification for reducing activity of a protein can also be attained by, for example, a mutagenesis treatment. Examples of the mutagenesis treatment can include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

Such methods for reducing the activity of a protein as mentioned above may be used independently or in an arbitrary combination.

When a protein functions as a complex having a plurality of subunits, some or all of the subunits may be modified, so long as the activity of the protein is eventually reduced. That is, for example, some or all of the genes that encode the respective subunits may be disrupted or the like. Furthermore, when there is a plurality of isozymes of a protein, some or all of the activities of the isozymes may be reduced, so long as the activity of the protein is eventually reduced. That is, for example, some or all of the genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA can include Northern hybridization, RT-PCR, microarray, RNA-seq, and so forth (Molecular Cloning, Cold Spring Harbor Laboratory Press, Cold Spring Harbor (USA), 2001). The amount of mRNA can be reduced to, for example, 50% or less, 20% or less, 10% or less, 5% or less, or 0% of that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein, such as the number of molecules of the protein per cell, can be reduced to, for example, 50% or less, 20% or less, 10% or less, 5% or less, or 0% of that of a non-modified strain.

Disruption of a gene can be confirmed by determining the nucleotide sequence of a part or the entire gene, restriction enzyme map, full length, or the like of the gene depending on the means used for the disruption.

The aforementioned methods for reducing the activity of a protein as mentioned above can be applied to reduction in the activities of arbitrary proteins such as an enzyme that catalyzes a reaction branching away from the biosynthesis pathway of an objective L-amino acid to generate a compound other than the objective L-amino acid, and reduction in the expression of arbitrary genes such as genes encoding those arbitrary proteins.

<2> Method for Producing L-Amino Acid

The method as described herein is a method for producing an L-amino acid that includes the steps of culturing the bacterium as described herein in a medium containing fructose to produce and cause accumulation of an L-amino acid in the medium and/or cells of the bacterium, and collecting the L-amino acid from the medium and/or cells of the bacterium. One kind of L-amino acid may be produced, or two or more kinds of L-amino acids may be produced.

The chosen medium is not particularly limited, so long as it contains fructose, the bacterium as described herein can proliferate in it, and an objective L-amino acid can be produced. As the medium, for example, a usual medium used for culture of bacteria such as coryneform bacteria and Enterobacteriaceae bacteria can be used. As the medium, for example, a medium containing carbon source, nitrogen source, phosphorus source, and sulfur source, as well as components selected from other various organic components and inorganic components as required can be used, in addition to fructose. Types and concentrations of the medium components can be appropriately determined according to various conditions such as the type of chosen bacterium.

In the method, fructose may be or may not be used as the sole carbon source. That is, fructose and another carbon source may be used in combination. Specific examples of the other carbon source can include, for example, saccharides such as glucose, sucrose, lactose, galactose, xylose, arabinose, blackstrap molasses, hydrolysates of starches, and hydrolysates of biomass, organic acids such as acetic acid, fumaric acid, citric acid, and succinic acid, alcohols such as glycerol, crude glycerol, and ethanol, and aliphatic acids. Particular examples of the other carbon source can include glucose. As the other carbon source, plant-derived materials can be used. Examples of the plant can include, for example, corn, rice, wheat, soybean, sugarcane, beet, and cotton. Examples of the plant-derived materials can include, for example, organs such as root, stem, trunk, branch, leaf, flower, and seed, plant bodies including them, and decomposition products of these plant organs. The forms of the plant-derived materials at the time of use thereof are not particularly limited, and they can be used in any form such as unprocessed product, juice, ground product, and purified product. Pentoses such as xylose, hexoses such as glucose, or mixtures of them can be obtained from, for example, plant biomass, and used. Specifically, these saccharides can be obtained by subjecting a plant biomass to such a treatment as steam treatment, hydrolysis with concentrated acid, hydrolysis with diluted acid, hydrolysis with an enzyme such as cellulase, and alkaline treatment. Since hemicellulose is generally more easily hydrolyzed compared with cellulose, hemicellulose in a plant biomass may be hydrolyzed beforehand to liberate pentoses, and then cellulose may be hydrolyzed to generate hexoses. Furthermore, xylose may be supplied by conversion from hexoses by, for example, imparting a pathway for converting hexose such as glucose to xylose to the chosen bacterium. As the other carbon source, a single kind of carbon source may be used, or two or more kinds of carbon sources may be used in combination.

Specific examples of the nitrogen source can include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas or aqueous ammonia used for adjusting pH may also be used as the nitrogen source. As the nitrogen source, a single kind of nitrogen source may be used, or two or more kinds of nitrogen sources may be used in combination.

Specific examples of the phosphate source can include, for example, phosphoric acid salts such as potassium dihydrogenphosphate and dipotassium hydrogenphosphate, and phosphoric acid polymers such as pyrophosphoric acid. As the phosphate source, a single kind of phosphate source may be used, or two or more kinds of phosphate sources may be used in combination.

Specific examples of the sulfur source can include, for example, inorganic sulfur compounds such as sulfates, thiosulfates, and sulfites, and sulfur-containing amino acids such as cysteine, cystine, and glutathione. As the sulfur source, a single kind of sulfur source may be used, or two or more kinds of sulfur sources may be used in combination.

Specific examples of other various organic components and inorganic components can include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing those such as peptone, casamino acid, yeast extract, and soybean protein decomposition product. As other various organic components and inorganic components, a single kind of component may be used, or two or more kinds of components may be used in combination.

Furthermore, when an auxotrophic mutant that requires an amino acid or the like for growth thereof is used, it is preferable to supply a required nutrient to the medium.

Furthermore, it is also preferable to, for example, restrict the amount of biotin in the medium, or add a surfactant or penicillin to the medium.

The culture conditions are not particularly limited so long as the bacterium as described herein can proliferate, and an objective L-amino acid can be produced. The culture can be performed, for example, under typical conditions used for culturing bacteria such as coryneform bacteria and Enterobacteriaceae bacteria. The culture conditions can be appropriately set according to various conditions such as the type of chosen bacterium.

The culture can be performed by using a liquid medium. At the time of the culture, the bacterium as described herein cultured on a solid medium such as agar medium may be directly inoculated into a liquid medium, or the bacterium cultured in a liquid medium as seed culture may be inoculated into a liquid medium for main culture. That is, the culture may be performed separately as seed culture and main culture. In such a case, the culture conditions of the seed culture and the main culture may be or may not be the same. The amount of the bacterium present in the medium at the time of the start of the culture is not particularly limited. The main culture may be performed by, for example, inoculating a seed culture broth to a medium for main culture at an amount of 1 to 50% (v/v).

The culture can be performed as batch culture, fed-batch culture, continuous culture, or a combination of these. The medium used at the time of the start of the culture can also be referred to as "starting medium". The medium supplied to a culture system (fermentation tank) in fed-batch culture or continuous culture can also be referred to as "feed medium". Furthermore, to supply a feed medium to a culture system in fed-batch culture or continuous culture can also be referred to as to "feed". Furthermore, when the culture is performed separately as seed culture and main culture, for example, both the seed culture and the main culture may be performed as batch culture. Alternatively, for example, the seed culture may be performed as batch culture, and the main culture may be performed as fed-batch culture or continuous culture.

The medium components each may be present in the starting medium, feed medium, or the both. The types of the components present in the starting medium may be or may not be the same as the types of the components present in the feed medium. The concentration of each component present in the starting medium may be or may not be the same as the concentration of the component present in the feed medium. Furthermore, two or more kinds of feed media containing different types and/or different concentrations of components may be used. For example, when medium is intermittently fed a plurality of times, the types and/or concentrations of components present in the feed media may be or may not be the same for each feeding.

The concentration of the carbon source in the medium is not particularly limited, so long as the bacterium can proliferate and produce an L-amino acid. The concentration of the carbon source in the medium may be as high as possible within such a range that production of the L-amino acid is not inhibited. The concentration of the carbon source in the medium may be, as the initial concentration (the concentration in the starting medium), for example, 1 to 30% (w/v), or 3 to 10% (w/v). Furthermore, the carbon source may be additionally supplied to the medium as required. For example, the carbon source may be additionally supplied to the medium in proportion to consumption of the carbon source accompanying progress of the fermentation.

When fructose and another carbon source are used in combination, the ratio of the amount of fructose with respect to the total amount of the carbon sources is not particularly limited, so long as the bacterium can utilize fructose as a carbon source. The ratio of the amount of fructose with respect to the total amount of the carbon sources may be, for example, 5% by weight or more, 10% by weight or more, 20% by weight or more, 30% by weight or more, 40% by weight or more, or 50% by weight or more. The ratio of the amount of fructose with respect to the total amount of the carbon sources may be within the above-exemplified range in terms of, for example, the initial amount (i.e. the amount in the starting medium), the fed amount (i.e. the amount in the feed medium), or the total use amount (i.e. the total amount of initial amount and fed amount).

The concentration of fructose in the medium is not particularly limited, so long as the bacterium as described herein can utilize fructose as a carbon source. Fructose may be contained in the medium, for example, at a concentration of 0.2 w/v % or higher, 0.5 w/v % or higher, or 1.0 w/v % or higher, or at a concentration of 30 w/v % or lower, 20 w/v % or lower, 10 w/v % or lower, 5 w/v % or lower, or 2 w/v % or lower, or at a concentration within the range defined with a combination thereof. Fructose may be present in the starting medium, feed medium, or the both at a concentration within the range exemplified above.

When fructose is present in the feed medium, fructose may be present in the feed medium at such a concentration that, for example, the fructose concentration in the medium after feeding is 0.01 w/v % or higher, 0.02 w/v % or higher, or 0.05 w/v % or higher, or becomes 5 w/v % or lower, 2 w/v % or lower, or 1 w/v % or lower, or is within the range defined with a combination thereof.

Fructose may be present in the medium at a concentration within the range exemplified above, when fructose is used as the sole carbon source. Alternatively, fructose may also be present in the medium at a concentration within the range exemplified above, when another carbon source is used in combination. Alternatively, fructose may also be present in the medium at a concentration within a range defined by appropriately modifying the range exemplified above on the basis of, for example, the ratio of the amount of fructose with respect to the total amount of the carbon sources, or the like, when another carbon source is used in combination.

Fructose may be or may not be present in the medium over the whole period of culture. For example, fructose may be or may not be present in the medium within a certain range, such as the range exemplified above, over the whole period of culture. For example, fructose may run short during a partial period of culture. The term "run short" can mean that the amount of fructose is smaller than the required amount, and it may mean that, for example, the concentration in the medium is zero. For example, fructose may be or may not be present in the medium from the start of culture. When fructose is not present in the medium at the start of culture, fructose is supplied to the medium after the start of culture. The timing of supplying fructose can be appropriately determined according to various conditions such as the length of the culture period. Furthermore, for example, fructose may be consumed during the culture, and thereby the concentration thereof in the medium may become zero. The term "partial period of culture" may refer to, for example, 1% or less, 5% or less, 10% or less, 20% or less, 30% or less, or 50% or less of the whole period of the culture. When the culture is performed as separate seed culture and main culture, the term "whole period of the culture" may mean the whole period of the main culture. It is preferred that, during a period when fructose runs short, another carbon source is present in a sufficient amount. Even if fructose runs short during a partial period of culture as described above, so long as there is a culture period using a medium containing fructose, the culture falls within the scope of the expression "culture of a bacterium in a medium containing fructose".

The concentrations of various components such as fructose can be measured by gas chromatography (Hashimoto, K. et al., Biosci. Biotechnol. Biochem., 1996, 70:22-30) or HPLC (Lin, J. T. et al., J. Chromatogr. A., 1998, 808:43-49).

The culture can be performed, for example, under an aerobic condition. The term "aerobic condition" can refer to a condition where the dissolved oxygen concentration in the liquid medium is not lower than 0.33 ppm, which is the detection limit for the detection with an oxygen membrane electrode, or may refer to a condition where the dissolved oxygen concentration in the liquid medium is not lower than 1.5 ppm. The oxygen concentration can be controlled to, for example, 5 to 50%, or about 10%, of the saturated oxygen concentration. Specifically, the culture under an aerobic condition can be performed by aeration culture, shaking culture, stirring culture, or a combination thereof. The pH of the medium may be, for example, 3 to 10, or 4.0 to 9.5. During the culture, the pH of the medium can be adjusted as required. The pH of the medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, calcium hydroxide, and magnesium hydroxide. The culture temperature may be, for example, 20 to 45° C., or 25 to 37° C. The culture period may be, for example, 10 to 120 hours. The culture may be continued, for example, until the carbon source contained in the medium is consumed, or until the bacterium loses the activity. By culturing the bacterium under such conditions as described above, an L-amino acid accumulates in the medium and/or cells of the bacterium.

Moreover, when L-glutamic acid is produced, the culture can be performed by using a liquid medium adjusted to satisfy a condition under which L-glutamic acid is precipitated, while precipitating L-glutamic acid in the medium. Examples of the condition under which L-glutamic acid is precipitated can include, for example, pH 5.0 to 4.0, pH 4.5 to 4.0, pH 4.3 to 4.0, or around pH 4.0 (EP1078989A).

Production of an L-amino acid can be confirmed by known methods used for detection or identification of compounds. Examples of such methods can include, for example, HPLC, LC/MS, GC/MS, and NMR. These methods can be independently used, or can be used in an appropriate combination.

The produced L-amino acid can be collected from the fermentation broth by known methods used for separation and purification of compounds. Examples of such methods can include, for example, ion-exchange resin method (Nagai, H. et al., Separation Science and Technology, 39(16), 3691-3710), precipitation, membrane separation (Japanese Patent Laid-open (Kokai) No. 9-164323 and Japanese Patent Laid-open (Kokai) No. 9-173792), and crystallization (WO2008/078448 and WO2008/078646). These methods can be independently used, or can be used in an appropriate combination. When the L-amino acid is accumulated in cells of the bacterium, for example, the cells can be disrupted with ultrasonic waves or the like, a supernatant can be obtained by removing the cells from the cell-disrupted suspension by centrifugation, and the L-amino acid can be collected from the supernatant by the ion exchange resin method or the like. The L-amino acid may be a free compound, a salt thereof, or a mixture thereof. Examples of the salt can include, for example, sulfate, hydrochloride, carbonate, ammonium salt, sodium salt, and potassium salt. When L-glutamic acid is produced, L-glutamic acid may specifically be, for example, free L-glutamic acid, sodium L-glutamate (monosodium L-glutamate, MSG), ammonium L-glutamate (monoammonium L-glutamate), or a mixture of these. For example, monosodium L-glutamate (MSG) can be obtained by adding an acid to the fermentation broth to crystallize ammonium L-glutamate contained therein, and then by adding an equimolar of sodium hydroxide to the crystals. In addition, decolorization can be performed by using activated carbon before and/or after the crystallization (see, Tetsuya KAWAKITA, "Industrial Crystallization for Monosodium L-Glutamate.", Bulletin of the Society of Sea Water Science, Japan, Vol. 56:5). The monosodium L-glutamate crystal can be used as, for example, an umami seasoning. The monosodium L-glutamate crystal may also be used as a seasoning in combination with a nucleic acid such as sodium guanylate and sodium inosinate, which also have umami taste.

When the L-amino acid is precipitated in the medium, it can be collected by centrifugation, filtration, or the like. The L-amino acid precipitated in the medium may also be isolated together with the L-amino acid dissolving in the medium, after the L-amino acid dissolving in the medium is crystallized.

The collected L-amino acid may contain such components as bacterial cells, medium components, moisture, and by-product metabolites of the bacterium in addition to the L-amino acid. The collected L-amino acid may also be purified at a desired extent. Purity of the collected L-amino acid may be, for example, 50% (w/w) or higher, 85% (w/w) or higher, or 95% (w/w) or higher (JP1214636B, U.S. Pat. Nos. 5,431,933, 4,956,471, 4,777,051, 4,946,654, 5,840, 358, 6,238,714, and US2005/0025878).

EXAMPLES

Hereinafter, the present invention will be more specifically explained with reference to non-limiting examples.

Example: Glutamic Acid Production Using *Corynebacterium Glutamicum* Strain Having Enhanced Expression of fucP-frk Genes In this example, glutamic acid production was carried out by using a glutamic acid-producing strain of *C. glutamicum* introduced with a non-PTS fructose-uptake carrier gene (fucP) and a fructokinase gene (Irk), and the effect of an enhanced expression of the fucP-frk genes on glutamic acid production was evaluated.

(1) Materials

Materials used in this Example are as follows.

TABLE 1

| | | <Primers> |
|---|---|---|
| Primer | SEQ ID NO | Nucleotide Sequence (5'→3') |
| 1 | 1 | CCAAGCTTGCATGCCATTTGCGCCTGCAA CGTAGGTTG |
| 2 | 2 | AACAGGAATGTTCCTTTCGAAAA |
| 3 | 3 | AGGAACATTCCTGTTATGACTTCAAATAT CCAAACCAGCG |
| 4 | 4 | TATAATCCTCCTTTAAGCATGTGATTCTT CCTTTGTC |
| 5 | 5 | GAATCACATGCTTAAAGGAGGATTATAAT GACTACCCCGATCGTTCTGAG |
| 6 | 6 | CCAAGCTTGCATGCCAGGAGGATTATAAT GACTACCCCGATCGTTCTGAG |
| 7 | 7 | CCAAGCTTGCATGCCCGGGGTGCTACGCG |
| 8 | 8 | CGGTACCCGGGGATCAGCACAGGACCGTT TGCCATTG |

<Plasmids>
pVK9 (Km$^R$; US2006-0141588)
pVK9-xfp (Km$^R$; WO2006/016705)
pVK9-PmsrA-fucP-frk (Km$^R$; present application)
pVS7 (Spc$^R$; WO2013/069634)
pVS7-xfp (Spc$^R$; present application)

<Strains>
*C. glutamicum* 2256ΔsucAΔldhA yggB*(WO2014/185430)
*C. glutamicum* 2256ΔsucAΔldhA yggB*/pVK9/pVS7 (present application)
*C. glutamicum* 2256ΔsucAΔldhA yggB*/pVK9-PmsrA-fucP-frk/pVS7 (present application)
*C. glutamicum* 2256ΔsucAΔldhA yggB*/pVK9/pVS7-xfp (present application)
*C. glutamicum* 2256ΔsucAΔldhA yggB*/pVK9-PmsrA-fucP-frk/pVS7-xfp (present application)

(2) Construction of Plasmids and Strains

PCR was carried out by using genomic DNA of the *C. glutamicum* 2256 strain (ATCC 13869) as the template, and primers 1 and 2, to amplify a DNA fragment containing an upstream region of the msrA gene of *C. glutamicum* (including a promoter region; 369 bp). PCR was carried out by using genomic DNA of *Corynebacterium ammoniagenes* ATCC 6872 as the template, and primers 3 and 4, to amplify a DNA fragment containing the fucP gene of *C. ammoniagenes* (GenBank: AMJ44784.1; 1335 bp). PCR was carried out by using genomic DNA of *Bifidobacterium longum* JCM1217 as the template, and primers 5 and 6, to amplify a DNA fragment containing the frk gene of *B. longum* (GenBank: BAJ66931.1; 897 bp). The obtained DNA fragments and pVK9 (US2006-0141588) digested with BamHI and PstI were mutually ligated by using Clontech In-fusion HD Cloning Kit (TaKaRa Inc.), to construct pVK9-PmsrA-fucP-frk, which is an expression plasmid of the fucP-frk genes.

PCR was carried out by using pVK9-xfp (WO2006/016705) as the template, and primers 7 and 8, to amplify a DNA fragment containing the phosphoketolase gene (xfp) of *B. longum* JCM1217. The obtained DNA fragment and pVS7 (WO2013/069634) digested with BamHI and PstI were mutually ligated by using Clontech In-fusion HD Cloning Kit (TaKaRa Inc.), to construct pVS7-xfp, which is an expression plasmid of the xfp gene.

The constructed plasmids were introduced into the *C. glutamicum* 2256ΔsucAΔldhA yggB* strain (WO2014/185430), to construct a strain having an enhanced expression of the fucP-frk genes and the xfp gene. The other strains used were also constructed by introduction of the respective plasmids. The 2256ΔsucAΔldhA yggB* strain is a glutamic acid-producing strain derived from the *C. glutamicum* 2256 strain (ATCC 13869). The 2256ΔsucAΔldhA yggB* strain is deficient in ldhA and sucA genes, and has an IS mutation (V419::IS) in yggB gene. The nucleotide sequence of this mutant yggB gene (V419::IS) and the amino acid sequence of the mutant YggB protein (V419::IS) encoded by the gene are shown in SEQ ID NOS: 11 and 12, respectively.

(3) Glutamic Acid Production Culture

Glutamic acid production culture was carried out by using the constructed strains. The compositions of media used are shown in Table 2.

TABLE 2

| Media composition CM2G medium | |
|---|---|
| Pepton | 10 g/L |
| Yeast Extract | 10 g/L |
| NaCl | 5 g/L |
| Biotin | 10 µg/L |
| Glucose | 5 g/L |

The medium of the aforementioned composition adjusted to pH7.0 with KOH was prepared, sterilized by autoclave (120° C., 20 min), and used for culture.

| Medium 1 | |
|---|---|
| Fructose | 80 g/L |
| $(NH_4)_2SO_4$ | 30 g/L |
| $KH_2PO_4$ | 1 g/L |
| $MgSO_4·7H_2O$ | 0.4 g/L |
| $FeSO_4·7H_2O$ | 0.01 g/L |
| $MnSO_4·5H_2O$ | 0.01 g/L |
| $VB_1$ | 200 µg/L |
| Biotin | 60 µg/L |
| Mameno | 0.48 g/L |

The medium of the aforementioned composition adjusted to pH8.0 with KOH was prepared, and sterilized by autoclave (115° C., 15 min). The sterilized medium was added with $CaCO_3$ at a concentration of 50 g/L, and used for culture.

| Medium 2 | |
|---|---|
| Glucose | 40 g/L |
| Fructose | 40 g/L |
| $(NH_4)_2SO_4$ | 30 g/L |
| $KH_2PO_4$ | 1 g/L |
| $MgSO_4·7H_2O$ | 0.4 g/L |
| $FeSO_4·7H_2O$ | 0.01 g/L |
| $MnSO_4·5H_2O$ | 0.01 g/L |
| $VB_1$ | 200 µg/L |
| Biotin | 60 µg/L |
| Mameno | 0.48 g/L |

The medium of the aforementioned composition adjusted to pH8.0 with KOH was prepared, and sterilized by autoclave (115° C., 15 min). The sterilized medium was added with $CaCO_3$ at a concentration of 50 g/L, and used for culture.

<Culture Evaluation 1: Evaluation with a Medium Containing Fructose as a Carbon Source>

Each strain was cultured on a CM2G plate added with the corresponding antibiotic(s) overnight at 31.5° C. Cells at an amount corresponding to ⅙ of the plate were scraped off, inoculated into 20 mL of Medium 1 contained in a Sakaguchi flask, and cultured at 30° C. with shaking at 120 rpm. A culture broth was sampled at 18 hr after the start of the culture, and the concentration of glutamic acid was measured by using a Biotech-analyzer AS-310 (SAKURA SI).

Results are shown in FIG. 1. It was confirmed that an enhanced expression of the fucP-frk genes improves accumulation of glutamic acid. In addition, it was also confirmed that an enhanced expression of the fucP-frk genes in combination with the xfp gene further improves accumulation of glutamic acid. Hence, it was concluded that the fucP-frk genes are effective elements for glutamic acid production using fructose as a carbon source.

<Culture Evaluation 2: Evaluation with a Medium Containing Glucose and Fructose as Carbon Sources>

Each strain was cultured on a CM2G plate added with the corresponding antibiotic(s) overnight at 31.5° C. Cells at an amount corresponding to ⅙ of the plate were scraped off, inoculated into 20 mL of Medium 2 contained in a Sakaguchi flask, and cultured at 30° C. with shaking at 120 rpm. A culture broth was sampled at 18 hr after the start of the culture, and the amount of cells (OD value at 620 nm; 101-fold diluted) and the concentration of glutamic acid were measured. The concentration of glutamic acid was measured by using a Biotech-analyzer AS-310 (SAKURA SI).

Figure 2:
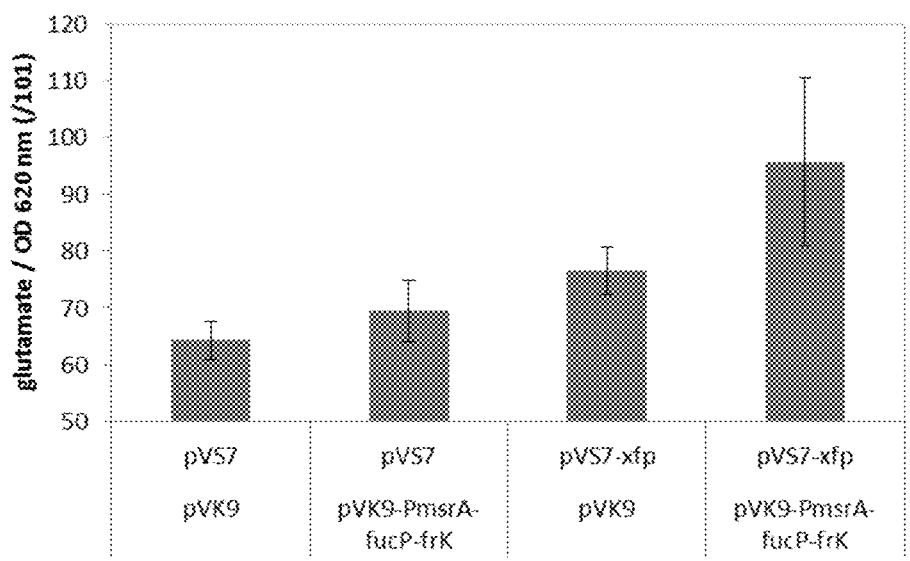
FIG. 2 shows a diagram showing results of glutamic acid production culture in a medium containing glucose and fructose as carbon sources using a *C. glutamicum* strain having increased expression of the fucP-frk genes.

Results are shown in FIG. 2. It was confirmed that enhanced expression of the fucP-frk genes improves accumulation of glutamic acid per amount of cells. In addition, it was also confirmed that enhanced expression of the fucP-frk genes in combination with the xfp gene further improves accumulation of glutamic acid per amount of cells. Hence, it was concluded that the fucP-frk genes are effective elements for glutamic acid production using glucose and fructose as carbon sources.

Explanation of Sequence Listing

SEQ ID NOS:

1-8: Primers

9: Nucleotide sequence of yggB gene of *Corynebacterium glutamicum* 2256 (ATCC 13869)

10: Amino acid sequence of YggB protein of *Corynebacterium glutamicum* 2256 (ATCC 13869)

11: Nucleotide sequence of mutant yggB gene (V419::IS) of *Corynebacterium glutamicum* 2256 (ATCC 13869)

12: Amino acid sequence of protein encoded by mutant yggB gene (V419::IS) of *Corynebacterium glutamicum* 2256 (ATCC 13869)
13: Nucleotide sequence of xfp gene of *Bifidobacterium longum* JCM1217
14: Amino acid sequence of Xfp protein of *Bifidobacterium longum* JCM1217
15-25: Primers
26: Nucleotide sequence of fucP gene of *Corynebacterium ammoniagenes* ATCC 6872
27: Amino acid sequence of FucP protein of *Corynebacterium ammoniagenes* ATCC 6872
28: Nucleotide sequence of fucP gene of *Pantoea ananatis* AJ13355
29: Amino acid sequence of FucP protein of *Pantoea ananatis* AJ13355
30: Nucleotide sequence of frk gene of *Bifidobacterium longum* JCM1217
31: Amino acid sequence of Frk protein of *Bifidobacterium longum* JCM1217
32: Nucleotide sequence of frk (mak) gene of *Pantoea ananatis* AJ13355
33: Amino acid sequence of Frk (Mak) protein of *Pantoea ananatis* AJ13355
34: Nucleotide sequence of frk (scrK) gene of *Pantoea ananatis* AJ13355
35: Amino acid sequence of Frk (ScrK) protein of *Pantoea ananatis* AJ13355

The invention claimed is:

1. A method for producing an L-amino acid, the method comprising:
   A) culturing a bacterium that is able to produce an L-amino acid in a medium containing fructose so that an L-amino acid is produced and accumulates in the medium and/or the bacterium; and
   B) collecting the L-amino acid from the medium and/or the bacterium,
   wherein the L-amino acid is selected from the group consisting of L-glutamic acid, L-glutamine, L-proline, L-arginine, L-citrulline, and L-ornithine,
   wherein the bacterium has been modified so that the activity of both a non-PTS fructose-uptake carrier and a fructokinase are increased as compared with a non-modified bacterium by increasing the expression of a gene encoding the non-PTS fructose-uptake carrier and a gene encoding the fructokinase, respectively,
   wherein the non-PTS fructose-uptake carrier is a protein selected from the group consisting of:
   (1a) a protein comprising the amino acid sequence of SEQ ID NO: 27 or 29;
   (1b) a protein comprising the amino acid sequence of SEQ ID NO: 27 or 29, but which includes substitution, deletion, insertion, and/or addition of 1 to 10 amino acid residues, and wherein said protein comprises non-PTS fructose-uptake activity; and
   (1c) a protein comprising an amino acid sequence having an identity of 90% or higher to the amino acid sequence of SEQ ID NO: 27 or 29, and wherein said protein comprises non-PTS fructose-uptake activity, and
   wherein the fructokinase is a protein selected from the group consisting of:
   (2a) a protein comprising the amino acid sequence of SEQ ID NO: 31, 33, or 35;
   (2b) a protein comprising the amino acid sequence of SEQ ID NO: 31, 33, or 35, but which includes substitution, deletion, insertion, and/or addition of 1 to 10 amino acid residues, and wherein said protein comprises fructokinase activity; and
   (2c) a protein comprising an amino acid sequence having an identity of 90% or higher to the amino acid sequence of SEQ ID NO: 31, 33, or 35, and wherein said protein comprises fructokinase activity.

2. The method according to claim 1, wherein the non-PTS fructose-uptake carrier is a protein encoded by a fucP gene.

3. The method according to claim 1, wherein the fructokinase is a protein encoded by a frk gene.

4. The method according to claim 1, wherein said increasing the expression comprises increasing the copy number of the gene(s) and/or replacing a promoter of the gene(s) with a stronger promoter.

5. The method according to claim 1, wherein the bacterium has further been modified so that the activity of phosphoketolase is increased as compared with a non-modified bacterium by increasing the expression of a gene encoding the phosphoketolase.

6. The method according to claim 5, wherein the phosphoketolase is D-xylulose-5-phosphate phosphoketolase and/or fructose-6-phosphate phosphoketolase.

7. The method according to claim 1, wherein the bacterium is a coryneform bacterium or a bacterium of the family Enterobacteriaceae.

8. The method according to claim 1, wherein the bacterium is a bacterium of the genus *Corynebacterium*.

9. The method according to claim 8, wherein the bacterium is *Corynebacterium glutamicum*.

10. The method according to claim 1, wherein the bacterium is a bacterium of the genus *Pantoea* or *Escherichia*.

11. The method according to claim 10, wherein the bacterium is *Pantoea ananatis* or *Escherichia coli*.

12. The method according to claim 1, wherein the L-amino acid is L-glutamic acid.

13. The method according to claim 12, wherein the L-glutamic acid is monoammonium L-glutamate or monosodium L-glutamate.

14. The method according to claim 1, wherein the bacterium has further been modified so that the activity of α-ketoglutarate dehydrogenase and/or succinate dehydrogenase is/are reduced as compared with a non-modified bacterium by disrupting a gene encoding the α-ketoglutarate dehydrogenase and/or a gene encoding the succinate dehydrogenase.

15. The method according to claim 12,
wherein the bacterium is a coryneform bacterium, and
wherein the bacterium has further been modified so as to harbor a mutant yggB gene.

16. The method according to claim 15, wherein the mutant yggB gene comprises a mutation selected from the group consisting of:
(1) a mutation in the region coding for the amino acid residues at positions 419 to 533 of a wild-type YggB protein,
(2) a mutation in the region coding for a transmembrane region of a wild-type YggB protein, and
(3) a combination thereof, and
wherein the wild-type YggB protein is selected from the group consisting of:
(a) a protein comprising the amino acid sequence of SEQ ID NO: 10;
(b) a protein comprising the amino acid sequence of SEQ ID NO: 10, but which includes substitution, deletion, insertion, and/or addition of 1 to 10 amino acid residues, and wherein said protein, when overexpressed in the coryneform bacterium, provides an improved ability of the coryneform bacterium to produce L-glutamic acid; and
(c) a protein comprising an amino acid sequence having an identity of 90% or higher to the amino acid sequence of SEQ ID NO: 10, and wherein said protein, when overexpressed in the coryneform bacterium, provides an improved ability of the coryneform bacterium to produce L-glutamic acid.

17. The method according to claim 1, wherein the medium further contains a carbon source other than fructose.

18. The method according to claim 17, wherein the carbon source is glucose.

* * * * *

SEQUENCE LISTING

```
<160> NUMBER OF SEQ ID NOS: 35

<210> SEQ ID NO 1
<211> LENGTH: 38
<212> TYPE: DNA
<213> ORGANISM: Artificial Sequence
<220> FEATURE:
<223> OTHER INFORMATION: primer

<400> SEQUENCE: 1
ccaagcttgc atgccatttg cgcctgcaac gtaggttg                          38

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
aacaggaatg ttcctttcga aaa                                          23

<210> SEQ ID NO 3
<211> LENGTH: 40
<212> TYPE: DNA
<213> ORGANISM: Artificial Sequence
<220> FEATURE:
<223> OTHER INFORMATION: primer

<400> SEQUENCE: 3
aggaacattc ctgttatgac ttcaaatatc caaaccagcg                        40

<210> SEQ ID NO 4
<211> LENGTH: 37
<212> TYPE: DNA
<213> ORGANISM: Artificial Sequence
<220> FEATURE:
<223> OTHER INFORMATION: primer

<400> SEQUENCE: 4
tataatcctc ctttaagcat gtgattcttc ctttgtc                           37

<210> SEQ ID NO 5
<211> LENGTH: 50
<212> TYPE: DNA
<213> ORGANISM: Artificial Sequence
<220> FEATURE:
<223> OTHER INFORMATION: primer

<400> SEQUENCE: 5
gaatcacatg cttaaaggag gattataatg actaccccga tcgttctgag              50
```

<210> SEQ ID NO 6
<211> LENGTH: 50
<212> TYPE: DNA
<213> ORGANISM: Artificial Sequence
<220> FEATURE:
<223> OTHER INFORMATION: primer

<400> SEQUENCE: 6
ccaagcttgc atgccaggag gattataatg actaccccga tcgttctgag          50

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7
ccaagcttgc atgcccgggg tgctacgcg                                 29

<210> SEQ ID NO 8
<211> LENGTH: 37
<212> TYPE: DNA
<213> ORGANISM: Artificial Sequence
<220> FEATURE:
<223> OTHER INFORMATION: primer

<400> SEQUENCE: 8
cggtacccgg ggatcagcac aggaccgttt gccattg                        37

<210> SEQ ID NO 9
<211> LENGTH: 1602
<212> TYPE: DNA
<213> ORGANISM: Corynebacterium glutamicum

<400> SEQUENCE: 9
atgattttag gcgtacccat tcaatatttg ctctattcat tgtggaattg gattgtcgat      60
accggttttg atgtagcaat tatcctggtc ttggcgtttt tgattccacg tatcggccga     120
ctggccatgc gtattatcaa gcagcgagtg gagtctgcag ccgatgcgga caccactaag     180
aaccagctcg cgttcgctgg cgttggcgtt tatatcgcgc aaattgtggc gttttcatg      240 cttgccgtct ccgcgatgca ggcttttggt ttctctctcg cgggcgctgc gattccggca     300
accattgcgt cagctgccat tggtcttggt gcgcagtcga ttgttgcgga cttcttggcc     360
ggatttttca tcctgacgga aaagcaattc ggcgtgggtg actgggtgcg ctttgagggc     420
aacggcatcg ttgttgaagg caccgtcatt gagatcacca tgcgcgcgac caaaattcgc     480
acgattgcac aagagaccgt gatcatcccg aactccacgg cgaaagtgtg catcaacaat     540
tctaataact ggtcgcgtgc ggttgtcgtt attccgatcc ccatgttggg ttctgaaaac     600
atcacagatg tcatcgcgcg ctctgaagct gcgactcgtc gcgcacttgg ccaggagaaa     660
atcgcaccgg aaatcctcgg tgaactcgat gtgcacccag ccacggaagt cacaccgcca     720
acggtggtcg gcatgccgtg gatggtcacc atgcgtttcc tcgtgcaagt caccgccggc     780
aatcaatggc tggtcgaacg cgccatccgc acagaaatca tcaacgaatt ctgggaagaa     840
tacggcagcg caaccactac atcgggaacc ctcattgatt ccttacacgt tgagcatgaa     900
gagccaaaga cctcgcttat cgacgcctcc ccccaggctc ttaaggaacc gaagccggag     960
gctgcggcga cggttgcatc gctagctgca tcgtctaacg acgatgcaga caatgcagac    1020

-continued

```
gcctcggcga tcaatgcagg caatccagag aaggaacttg attccgatgt gctggaacaa      1080
gaactctcca gcgaagaacc ggaagaaaca gcaaaaccag atcactctct ccgaggcttc      1140
ttccgcactg attactaccc aaatcggtgg cagaagatcc tgtcgtttgg cggacgtgtc      1200
cgcatgagca cttccctgtt gttgggtgcg ctgctcttgc tgtcactatt taaggtcatg      1260
actgtggaac aagtgagaa ttggcaaaac tccagtggat ggctgtcacc aagcactgcc       1320
acctcaactg cggtgaccac ctccgaaact tccgcgccag caagcacgcc ttcgatgaca      1380
gtgcccacta cggtggagga daccccaacg atggaatcta gcgtcgaaac gcagcaggaa      1440
acctcaaccc ctgcaaccgc aacgccccag cgagccgaca ccatcgaacc gaccgaggaa      1500
gccacgtcgc aggaggaaac gactgcatcg cagacgcagt ctccagcagt ggaagcacca      1560
accgcggtcc aagaaacagt tgcgccgacg tccaccccct tag                       1602
```

<210> SEQ ID NO 10
<211> LENGTH: 533
<212> TYPE: PRT
<213> ORGANISM: Corynebacterium glutamicum

<400> SEQUENCE: 10

```
Met Ile Leu Gly Val Pro Ile Gln Tyr Leu Leu Tyr Ser Leu Trp Asn
1               5                  10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270
```

```
Ile Ile Asn Glu Phe Trp Glu Glu Tyr Gly Ser Ala Thr Thr Thr Ser
            275                 280                 285

Gly Thr Leu Ile Asp Ser Leu His Val Glu His Glu Glu Pro Lys Thr
        290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Ala Gly Asn Pro Glu Lys Glu
                340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
    370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Ser Glu Asn Trp Gln Asn Ser Ser
            420                 425                 430

Gly Trp Leu Ser Pro Ser Thr Ala Thr Ser Thr Ala Val Thr Thr Ser
        435                 440                 445

Glu Thr Ser Ala Pro Ala Ser Thr Pro Ser Met Thr Val Pro Thr Thr
    450                 455                 460

Val Glu Glu Thr Pro Thr Met Glu Ser Ser Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Thr Thr Ala Ser Gln Thr
            500                 505                 510

Gln Ser Pro Ala Val Glu Ala Pro Thr Ala Val Gln Glu Thr Val Ala
    515                 520                 525

Pro Thr Ser Thr Pro
    530

<210> SEQ ID NO 11
<211> LENGTH: 3063
<212> TYPE: DNA
<213> ORGANISM: Corynebacterium glutamicum
<220> FEATURE:
<221> NAME/KEY: CDS
<222> LOCATION: (1)..(1269)

<400> SEQUENCE: 11 atg att tta ggc gta ccc att caa tat ttg ctc tat tca ttg tgg aat    48
Met Ile Leu Gly Val Pro Ile Gln Tyr Leu Leu Tyr Ser Leu Trp Asn
1               5                   10                  15 tgg att gtc gat acc ggt ttt gat gta gca att atc ctg gtc ttg gcg    96
Trp Ile Val Asp Thr Gly Phe Asp Val Ala Ile Ile Leu Val Leu Ala
            20                  25                  30 ttt ttg att cca cgt atc ggc cga ctg gcc atg cgt att atc aag cag   144
Phe Leu Ile Pro Arg Ile Gly Arg Leu Ala Met Arg Ile Ile Lys Gln
        35                  40                  45 cga gtg gag tct gca gcc gat gcg gac acc act aag aac cag ctc gcg   192
Arg Val Glu Ser Ala Ala Asp Ala Asp Thr Thr Lys Asn Gln Leu Ala
    50                  55                  60 ttc gct ggc gtt ggc gtt tat atc gcg caa att gtg gcg ttt ttc atg   240
```

```
                Phe Ala Gly Val Gly Val Tyr Ile Ala Gln Ile Val Ala Phe Phe Met
                 65                  70                  75                  80 ctt gcc gtc tcc gcg atg cag gct ttt ggt ttc tct ctc gcg ggc gct            288
Leu Ala Val Ser Ala Met Gln Ala Phe Gly Phe Ser Leu Ala Gly Ala
                     85                  90                  95 gcg att ccg gca acc att gcg tca gct gcc att ggt ctt ggt gcg cag            336
Ala Ile Pro Ala Thr Ile Ala Ser Ala Ala Ile Gly Leu Gly Ala Gln
                    100                 105                 110 tcg att gtt gcg gac ttc ttg gcc gga ttt ttc atc ctg acg gaa aag            384
Ser Ile Val Ala Asp Phe Leu Ala Gly Phe Phe Ile Leu Thr Glu Lys
                    115                 120                 125 caa ttc ggc gtg ggt gac tgg gtg cgc ttt gag ggc aac ggc atc gtt            432
Gln Phe Gly Val Gly Asp Trp Val Arg Phe Glu Gly Asn Gly Ile Val
        130                 135                 140 gtt gaa ggc acc gtc att gag atc acc atg cgc gcg acc aaa att cgc            480
Val Glu Gly Thr Val Ile Glu Ile Thr Met Arg Ala Thr Lys Ile Arg
145                 150                 155                 160 acg att gca caa gag acc gtg atc atc ccg aac tcc acg gcg aaa gtg            528
Thr Ile Ala Gln Glu Thr Val Ile Ile Pro Asn Ser Thr Ala Lys Val
                    165                 170                 175 tgc atc aac aat tct aat aac tgg tcg cgt gcg gtt gtc gtt att ccg            576
Cys Ile Asn Asn Ser Asn Asn Trp Ser Arg Ala Val Val Val Ile Pro
                180                 185                 190 atc ccc atg ttg ggt tct gaa aac atc aca gat gtc atc gcg cgc tct            624
Ile Pro Met Leu Gly Ser Glu Asn Ile Thr Asp Val Ile Ala Arg Ser
            195                 200                 205 gaa gct gcg act cgt cgc gca ctt ggc cag gag aaa atc gca ccg gaa            672
Glu Ala Ala Thr Arg Arg Ala Leu Gly Gln Glu Lys Ile Ala Pro Glu
        210                 215                 220 atc ctc ggt gaa ctc gat gtg cac cca gcc acg gaa gtc aca ccg cca            720
Ile Leu Gly Glu Leu Asp Val His Pro Ala Thr Glu Val Thr Pro Pro
225                 230                 235                 240 acg gtg gtc ggc atg ccg tgg atg gtc acc atg cgt ttc ctc gtg caa            768
Thr Val Val Gly Met Pro Trp Met Val Thr Met Arg Phe Leu Val Gln
                    245                 250                 255 gtc acc gcc ggc aat caa tgg ctg gtc gaa cgc gcc atc cgc aca gaa            816
Val Thr Ala Gly Asn Gln Trp Leu Val Glu Arg Ala Ile Arg Thr Glu
                260                 265                 270 atc atc aac gaa ttc tgg gaa gaa tac ggc agc gca acc act aca tcg            864
Ile Ile Asn Glu Phe Trp Glu Glu Tyr Gly Ser Ala Thr Thr Thr Ser
            275                 280                 285 gga acc ctc att gat tcc tta cac gtt gag cat gaa gag cca aag acc            912
Gly Thr Leu Ile Asp Ser Leu His Val Glu His Glu Glu Pro Lys Thr
        290                 295                 300 tcg ctt atc gac gcc tcc ccc cag gct ctt aag gaa ccg aag ccg gag            960
Ser Leu Ile Asp Ala Ser Pro Gln Ala Leu Lys Glu Pro Lys Pro Glu
305                 310                 315                 320 gct gcg gcg acg gtt gca tcg cta gct gca tcg tct aac gac gat gca           1008
Ala Ala Ala Thr Val Ala Ser Leu Ala Ala Ser Ser Asn Asp Asp Ala
                    325                 330                 335 gac aat gca gac gcc tcg gcg atc aat gca ggc aat cca gag aag gaa           1056
Asp Asn Ala Asp Ala Ser Ala Ile Asn Ala Gly Asn Pro Glu Lys Glu
                340                 345                 350 ctt gat tcc gat gtg ctg gaa caa gaa ctc tcc agc gaa gaa ccg gaa           1104
Leu Asp Ser Asp Val Leu Glu Gln Glu Leu Ser Ser Glu Glu Pro Glu
            355                 360                 365 gaa aca gca aaa cca gat cac tct ctc cga ggc ttc ttc cgc act gat           1152
Glu Thr Ala Lys Pro Asp His Ser Leu Arg Gly Phe Phe Arg Thr Asp
        370                 375                 380
```

| tac tac cca aat cgg tgg cag aag atc ctg tcg ttt ggc gga cgt gtc | 1200 |
| Tyr Tyr Pro Asn Arg Trp Gln Lys Ile Leu Ser Phe Gly Gly Arg Val | |
| 385                 390                 395                 400 | |

| cgc atg agc act tcc ctg ttg ttg ggt gcg ctg ctc ttg ctg tca cta | 1248 |
| Arg Met Ser Thr Ser Leu Leu Leu Gly Ala Leu Leu Leu Leu Ser Leu | |
|             405                 410                 415         | |

| ttt aag ggg ctc ttc ctg ttt tagagtgcat tgatcttatg gaccaactgc | 1299 |
| Phe Lys Gly Leu Phe Leu Phe | |
|         420 | |

| cctgaatgga taaggcaccg cagaatgtag tggttcaaat tacggaaacc tagagcaatc | 1359 |
| ccacgcaaat gctccaaccg tccgttgatc gcttcgaccg gaccgttgga dacaccaaca | 1419 |
| tcgaaatacg ccaacacatc accaagtcgt ttaaacaaac tacgacccaa ctgcgcgagt | 1479 |
| tccttattcg gccccttcaa cacccgaagc tgatcaataa tggtccgcat tttcttcttc | 1539 |
| gcttcacgct tattacccat ctgataacaa tcaataatcg cctgatacgc aagccacgca | 1599 |
| agctttaaca ccccgtagtc tttgtcatac gcccacaact gctccaagct ttcttgctga | 1659 |
| cgaggactca accacttgtg cgtggtcaac aaggtcttcc ggtttttata caacggatcc | 1719 |
| tggcttaaac cacgacgctg gtatttctcc cgctggaggc gttgccggca ggcggtgagc | 1779 |
| ttgtcaccag caagccgcac aacatggaat ggatccatca cgcgacgagc agaaggaatg | 1839 |
| agttctttac ttgctgtggc gtagccttgg aacccatcca tggacacgat ccgtatctga | 1899 |
| ttgcggaact gttcaccgcg gaaccaagc caggaccgta aagcatcagc actacgacct | 1959 |
| gggacgacat ctaataaccg ggcaggacac cgtgagtcat accgatgccc ggtcatatcg | 2019 |
| acaatcacgg tgacaaaccc atcaccatgc ttagccctat tatgtgacca cttatgctca | 2079 |
| tccaccccaa tgacatacac tccatcaaga tggtgaggat cgttatagac cagctcacgg | 2139 |
| cacatatcga gggctagttg gcaggttaaa tcccaccta gcccaagtgc tttcgcggtt | 2199 |
| gcgtgaacac tcatccggtc aatagcaagg cgttgcaaaa tccagcgggt gacccggtgg | 2259 |
| gtgaccttt taccgtggtc agcgcagctt agttctgctt ggaaatactt ttgcttacat | 2319 |
| gtcgggttgg tgcagcggta gcgaggtaga cggataaaca gtttggtggg aaacccgacg | 2379 |
| atgggtaaat caatgagcat ccggtgggtg tgatgacgaa acaccccagg ttgggagcat | 2439 |
| tctgggcagg tggaggtata gtcgagtgcg tctgcttcga tcagggtgta atcacctgca | 2499 |
| tcggaagcgc cggtgatggt gagtcctagt tccgcagtgc ggcagatggt gtcagcgatg | 2559 |
| atgttgccgg tagacttcat gggtagagcc ttttgttggt gtttggttag cttagatacc | 2619 |
| taaaccttaa ccctgacaaa aggctcgttt attttcgggt ctacaccgct agcccaggtt | 2679 |
| ctgtgatgta ccccaaaacc ggaagggcca tttaaggtca tgactgtgga accaagtgag | 2739 |
| aattggcaaa actccagtgg atggctgtca ccaagcactg ccacctcaac tgcggtgacc | 2799 |
| acctccgaaa cttccgcgcc agcaagcacg ccttcgatga cagtgcccac tacggtggag | 2859 |
| gagaccccaa cgatggaatc tagcgtcgaa acgcagcagg aaacctcaac ccctgcaacc | 2919 |
| gcaacgcccc agcgagccga caccatcgaa ccgaccgagg aagccacgtc gcaggaggaa | 2979 |
| acgactgcat cgcagacgca gtctccagca gtggaagcac caaccgcggt ccaagaaaca | 3039 |
| gttgcgccga cgtccacccc ttag | 3063 |

<210> SEQ ID NO 12
<211> LENGTH: 423
<212> TYPE: PRT
<213> ORGANISM: Corynebacterium glutamicum

<400> SEQUENCE: 12

```
Met Ile Leu Gly Val Pro Ile Gln Tyr Leu Tyr Ser Leu Trp Asn
1               5                   10                  15

Trp Ile Val Asp Thr Gly Phe Asp Val Ala Ile Ile Leu Val Leu Ala
                20                  25                  30

Phe Leu Ile Pro Arg Ile Gly Arg Leu Ala Met Arg Ile Ile Lys Gln
                35                  40                  45

Arg Val Glu Ser Ala Ala Asp Ala Asp Thr Thr Lys Asn Gln Leu Ala
        50                  55                  60

Phe Ala Gly Val Gly Val Tyr Ile Ala Gln Ile Val Ala Phe Phe Met
65                      70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
                100                 105                 110

Ser Ile Val Ala Asp Phe Leu Ala Gly Phe Phe Ile Leu Thr Glu Lys
            115                 120                 125

Gln Phe Gly Val Gly Asp Trp Val Arg Phe Glu Gly Asn Gly Ile Val
        130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
                180                 185                 190

Ile Pro Met Leu Gly Ser Glu Asn Ile Thr Asp Val Ile Ala Arg Ser
            195                 200                 205

Glu Ala Ala Thr Arg Arg Ala Leu Gly Gln Glu Lys Ile Ala Pro Glu
        210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
                260                 265                 270

Ile Ile Asn Glu Phe Trp Glu Glu Tyr Gly Ser Ala Thr Thr Thr Ser
                275                 280                 285

Gly Thr Leu Ile Asp Ser Leu His Val Glu His Glu Glu Pro Lys Thr
        290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Glu Pro Glu
        355                 360                 365

Glu Thr Ala Lys Pro Asp His Ser Leu Arg Gly Phe Phe Arg Thr Asp
        370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415
```

Phe Lys Gly Leu Phe Leu Phe
            420

<210> SEQ ID NO 13
<211> LENGTH: 2478
<212> TYPE: DNA
<213> ORGANISM: Bifidobacterium longum

<400> SEQUENCE: 13

| | | | | | |
|---|---|---|---|---|---|
| atgacgagtc | ctgttattgg | cacccttgg | aagaagctca | acgctccggt | ttccgaggaa | 60 |
| gccctcgaag | gcgttgacaa | gtactggcgc | gttgccaact | acctttccat | cggccagatt | 120 |
| tatctgcgtt | ccaacccgct | gatgaaggag | cccttcaccc | gcgaagatgt | gaagcaccgt | 180 |
| ctggtgggcc | actggggcac | tacccctggc | ctgaacttcc | tcatcggcca | catcaaccgt | 240 |
| ttcattgctg | accacggcca | gaacaccgtg | atcatcatgg | gcccgggcca | cggtggcccg | 300 |
| gccggtacct | cccagtccta | cctggacggc | acctacaccg | agaccttccc | gaagatcacc | 360 |
| aaggacgaag | ctggtctgca | gaagttcttc | cgtcagttct | cttacccggg | cggcattccg | 420 |
| tcccacttcg | ctccggagac | cccgggctcc | atccacgagg | tggtgagct | gggttacgct | 480 |
| ctgtcccacg | cttacggcgc | catcatggac | aacccgagcc | tgtttgtccc | ggccatcgtc | 540 |
| ggcgacggcg | aggctgagac | cggcccgctg | gctaccggct | ggcagtccaa | caagctcgtg | 600 |
| aacccgcgca | ccgacggtat | cgtgctgccg | atcctgcacc | tcaacggcta | caagatcgcc | 660 |
| aacccgacca | tcctgtcccg | catctccgac | gaagagctcc | acgagttctt | ccacggcatg | 720 |
| ggttacgagc | cctacgagtt | cgtcgctggc | ttcgatgatg | aggaccacat | gtccatccac | 780 |
| cgtcgcttcg | ccgagctgtg | ggagaccatc | tgggacgaga | tctgcgacat | caaggccacc | 840 |
| gctcagaccg | acaacgtgca | ccgtccgttc | tacccgatgc | tgatcttccg | cacccccgaag | 900 |
| ggctggacct | gcccgaagta | catcgacggc | aagaagaccg | agggctcctg | gcgttcccac | 960 |
| caggtgccgc | tggcttccgc | ccgcgacacc | gaggcccact | cgaggttct | caagaactgg | 1020 |
| ctcgagtcct | acaagccgga | agagctgttc | gacgccaacg | gtgctgtcaa | ggacgacgtc | 1080 |
| cttgccttca | tgccgaaggg | cgagctgcgt | atcggtgcca | acccgaacgc | caacggtggt | 1140 |
| gtgatccgca | acgacctgaa | gctgccgaac | ctcgaggact | acgaggtcaa | ggaagtggct | 1200 |
| gagtacggcc | acggctgggg | ccagctcgag | gccacccgta | ccctgggtgc | ctacactcgc | 1260 |
| gacatcatca | gaacaaccc | gcgcgacttc | cgcatcttcg | accggatga | accgcttcc | 1320 |
| aaccgtctgc | aggcttccta | cgaagtcacc | aacaagcagt | gggatgccgg | ctacatctcc | 1380 |
| gacgaggtcg | acgagcacat | gcgtctcc | ggccaggtcg | ttgagcagct | gtccgagcac | 1440 |
| cagatggaag | cttcctcga | ggcttacctg | ctgaccggtc | gtcacggcat | ctggagctcc | 1500 |
| tacgagtcct | tcgtccacgt | gatcgactcc | atgctgaacc | agcacgccaa | gtggcttgag | 1560 |
| gctaccgtcc | gcgagattcc | gtggcgcaag | ccgattgcct | ccatgaacct | gctggtctcc | 1620 |
| tcccacgttt | ggcgtcagga | ccacaacggc | ttctcccacc | aggatccggg | tgtcacctcc | 1680 |
| gtcctgctga | acaagtgctt | ccacaacgac | cacgtcatcg | gcatctactt | cgccaccgat | 1740 |
| gcgaacatgc | tgctggccat | cgccgagaag | tgctacaagt | ccaccaacaa | gatcaacgcc | 1800 |
| atcatcgctg | gtaagcagcc | tgctgccacc | tggctgaccc | tggacgaggc | tcgtgccgag | 1860 |
| ctcgagaagg | gtgccgccgc | ttgggattgg | gcttccaccg | ccaagaacaa | cgatgaggcc | 1920 |
| gaggtcgtgc | ttgccgccgc | cggcgatgtc | ccgactcagg | agatcatggc | tgcttccgac | 1980 |
| aagctgaagg | aactgggcat | caagttcaag | gttgtgaacg | ttgccgacct | gctctccctg | 2040 |

-continued

```
cagtccgcca aggagaacga cgaggctctg accgacgagg agttcgccga catcttcacc   2100
gccgacaagc cggtgctgtt cgcgtaccac tcctacgctc acgacgtgcg tggcctgatc   2160
tacgaccgtc cgaaccacga caacttcaac gtccacggct acgaggagga gggctccacc   2220
accaccccgt acgacatggt tcgtgtcaac cgcatcgacc gctacgagct gaccgctgag   2280
gctctgcgca tgatcgacgc cgacaagtac gccgacaaga tcgacgagct cgagaagttc   2340
cgtgatgagg ccttccagtt cgccgtcgac aacggctacg atcacccgga ctacaccgac   2400
tgggtgtact ccggcgtgaa caccgacaag aagggtgccg tcaccgctac cgccgctacc   2460
gctggcgaca acgagtga                                                  2478
```

<210> SEQ ID NO 14
<211> LENGTH: 825
<212> TYPE: PRT
<213> ORGANISM: Bifidobacterium longum

<400> SEQUENCE: 14

```
Met Thr Ser Pro Val Ile Gly Thr Pro Trp Lys Lys Leu Asn Ala Pro
1               5                   10                  15

Val Ser Glu Glu Ala Leu Glu Gly Val Asp Lys Tyr Trp Arg Val Ala
            20                  25                  30

Asn Tyr Leu Ser Ile Gly Gln Ile Tyr Leu Arg Ser Asn Pro Leu Met
        35                  40                  45

Lys Glu Pro Phe Thr Arg Glu Asp Val Lys His Arg Leu Val Gly His
    50                  55                  60

Trp Gly Thr Thr Pro Gly Leu Asn Phe Leu Ile Gly His Ile Asn Arg
65                  70                  75                  80

Phe Ile Ala Asp His Gly Gln Asn Thr Val Ile Met Gly Pro Gly
                85                  90                  95

His Gly Gly Pro Ala Gly Thr Ser Gln Ser Tyr Leu Asp Gly Thr Tyr
            100                 105                 110

Thr Glu Thr Phe Pro Lys Ile Thr Lys Asp Glu Ala Gly Leu Gln Lys
        115                 120                 125

Phe Phe Arg Gln Phe Ser Tyr Pro Gly Gly Ile Pro Ser His Phe Ala
    130                 135                 140

Pro Glu Thr Pro Gly Ser Ile His Glu Gly Gly Glu Leu Gly Tyr Ala
145                 150                 155                 160

Leu Ser His Ala Tyr Gly Ala Ile Met Asp Asn Pro Ser Leu Phe Val
                165                 170                 175

Pro Ala Ile Val Gly Asp Gly Glu Ala Glu Thr Gly Pro Leu Ala Thr
            180                 185                 190

Gly Trp Gln Ser Asn Lys Leu Val Asn Pro Arg Thr Asp Gly Ile Val
        195                 200                 205

Leu Pro Ile Leu His Leu Asn Gly Tyr Lys Ile Ala Asn Pro Thr Ile
    210                 215                 220

Leu Ser Arg Ile Ser Asp Glu Glu Leu His Glu Phe Phe His Gly Met
225                 230                 235                 240

Gly Tyr Glu Pro Tyr Glu Phe Val Ala Gly Phe Asp Asp Glu Asp His
                245                 250                 255

Met Ser Ile His Arg Arg Phe Ala Glu Leu Trp Glu Thr Ile Trp Asp
            260                 265                 270

Glu Ile Cys Asp Ile Lys Ala Thr Ala Gln Thr Asp Asn Val His Arg
        275                 280                 285

Pro Phe Tyr Pro Met Leu Ile Phe Arg Thr Pro Lys Gly Trp Thr Cys
```

-continued

```
            290                 295                 300

Pro Lys Tyr Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
                    325                 330                 335

Leu Lys Asn Trp Leu Glu Ser Tyr Lys Pro Glu Leu Phe Asp Ala
                340                 345                 350

Asn Gly Ala Val Lys Asp Val Leu Ala Phe Met Pro Lys Gly Glu
                355                 360                 365

Leu Arg Ile Gly Ala Asn Pro Asn Ala Asn Gly Gly Val Ile Arg Asn
    370                 375                 380

Asp Leu Lys Leu Pro Asn Leu Glu Asp Tyr Glu Val Lys Glu Val Ala
385                 390                 395                 400

Glu Tyr Gly His Gly Trp Gly Gln Leu Glu Ala Thr Arg Thr Leu Gly
                    405                 410                 415

Ala Tyr Thr Arg Asp Ile Ile Lys Asn Asn Pro Arg Asp Phe Arg Ile
                420                 425                 430

Phe Gly Pro Asp Glu Thr Ala Ser Asn Arg Leu Gln Ala Ser Tyr Glu
                435                 440                 445

Val Thr Asn Lys Gln Trp Asp Ala Gly Tyr Ile Ser Asp Glu Val Asp
                450                 455                 460

Glu His Met His Val Ser Gly Gln Val Val Glu Gln Leu Ser Glu His
465                 470                 475                 480

Gln Met Glu Gly Phe Leu Glu Ala Tyr Leu Leu Thr Gly Arg His Gly
                    485                 490                 495

Ile Trp Ser Ser Tyr Glu Ser Phe Val His Val Ile Asp Ser Met Leu
                500                 505                 510

Asn Gln His Ala Lys Trp Leu Glu Ala Thr Val Arg Glu Ile Pro Trp
                515                 520                 525

Arg Lys Pro Ile Ala Ser Met Asn Leu Leu Val Ser Ser His Val Trp
530                 535                 540

Arg Gln Asp His Asn Gly Phe Ser His Gln Asp Pro Gly Val Thr Ser
545                 550                 555                 560

Val Leu Leu Asn Lys Cys Phe His Asn Asp His Val Ile Gly Ile Tyr
                565                 570                 575

Phe Ala Thr Asp Ala Asn Met Leu Leu Ala Ile Ala Glu Lys Cys Tyr
                580                 585                 590

Lys Ser Thr Asn Lys Ile Asn Ala Ile Ile Ala Gly Lys Gln Pro Ala
                595                 600                 605

Ala Thr Trp Leu Thr Leu Asp Glu Ala Arg Ala Glu Leu Glu Lys Gly
    610                 615                 620

Ala Ala Ala Trp Asp Trp Ala Ser Thr Ala Lys Asn Asn Asp Glu Ala
625                 630                 635                 640

Glu Val Val Leu Ala Ala Gly Asp Val Pro Thr Gln Glu Ile Met
                    645                 650                 655

Ala Ala Ser Asp Lys Leu Lys Glu Leu Gly Ile Lys Phe Lys Val Val
                660                 665                 670

Asn Val Ala Asp Leu Leu Ser Leu Gln Ser Ala Lys Glu Asn Asp Glu
                675                 680                 685

Ala Leu Thr Asp Glu Glu Phe Ala Asp Ile Phe Thr Ala Asp Lys Pro
    690                 695                 700

Val Leu Phe Ala Tyr His Ser Tyr Ala His Asp Val Arg Gly Leu Ile
705                 710                 715                 720
```

-continued

```
Tyr Asp Arg Pro Asn His Asp Asn Phe Asn Val His Gly Tyr Glu Glu
            725                 730                 735

Glu Gly Ser Thr Thr Thr Pro Tyr Asp Met Val Arg Val Asn Arg Ile
        740                 745                 750

Asp Arg Tyr Glu Leu Thr Ala Glu Ala Leu Arg Met Ile Asp Ala Asp
    755                 760                 765

Lys Tyr Ala Asp Lys Ile Asp Glu Leu Glu Lys Phe Arg Asp Glu Ala
770                 775                 780

Phe Gln Phe Ala Val Asp Asn Gly Tyr Asp His Pro Asp Tyr Thr Asp
785                 790                 795                 800

Trp Val Tyr Ser Gly Val Asn Thr Asp Lys Lys Gly Ala Val Thr Ala
            805                 810                 815

Thr Ala Ala Thr Ala Gly Asp Asn Glu
            820                 825
```

<210> SEQ ID NO 15
<211> LENGTH: 37
<212> TYPE: DNA
<213> ORGANISM: Artificial Sequence
<220> FEATURE:
<223> OTHER INFORMATION: primer

<400> SEQUENCE: 15
cgacaacgag tgatctagaa aacagaattt gcctggc            37

<210> SEQ ID NO 16
<211> LENGTH: 52
<212> TYPE: DNA
<213> ORGANISM: Artificial Sequence
<220> FEATURE:
<223> OTHER INFORMATION: primer

<400> SEQUENCE: 16
aacaggactc gtcatgtcga cctccttctt aaattggtta ataaccagtg ac            52

<210> SEQ ID NO 17
<211> LENGTH: 30
<212> TYPE: DNA
<213> ORGANISM: Artificial Sequence
<220> FEATURE:
<223> OTHER INFORMATION: primer

<400> SEQUENCE: 17
gtcgacatga cgagtcctgt tattggcacc            30

<210> SEQ ID NO 18
<211> LENGTH: 39
<212> TYPE: DNA
<213> ORGANISM: Artificial Sequence
<220> FEATURE:
<223> OTHER INFORMATION: primer

<400> SEQUENCE: 18
attctgtttt ctagatcact cgttgtcgcc agcggtagc            39

<210> SEQ ID NO 19
<211> LENGTH: 42
<212> TYPE: DNA
<213> ORGANISM: Artificial Sequence
<220> FEATURE:
<223> OTHER INFORMATION: primer

<400> SEQUENCE: 19
cgttgttgcc attgctgaag cctgcttttt tatactaact tg                42

<210> SEQ ID NO 20
<211> LENGTH: 31
<212> TYPE: DNA
<213> ORGANISM: Artificial Sequence
<220> FEATURE:
<223> OTHER INFORMATION: primer

<400> SEQUENCE: 20
gaagtcatgg cagtctcctt gtgtgaaatt g                            31

<210> SEQ ID NO 21
<211> LENGTH: 32
<212> TYPE: DNA
<213> ORGANISM: Artificial Sequence
<220> FEATURE:
<223> OTHER INFORMATION: primer

<400> SEQUENCE: 21
gactgccatg acttcaaata tccaaaccag cg                           32

<210> SEQ ID NO 22
<211> LENGTH: 40
<212> TYPE: DNA
<213> ORGANISM: Artificial Sequence
<220> FEATURE:
<223> OTHER INFORMATION: primer

<400> SEQUENCE: 22
atgacttggt tgagtttaag catgtgattc ttcctttgtc                   40

<210> SEQ ID NO 23
<211> LENGTH: 32
<212> TYPE: DNA
<213> ORGANISM: Artificial Sequence
<220> FEATURE:
<223> OTHER INFORMATION: primer

<400> SEQUENCE: 23
gtagtcatgg cagtctcctt gtgtgaaatt gt                           32

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
gactgccatg actaccccga tcgttctgag                              30

<210> SEQ ID NO 25
<211> LENGTH: 39
<212> TYPE: DNA
<213> ORGANISM: Artificial Sequence
<220> FEATURE:
<223> OTHER INFORMATION: primer

<400> SEQUENCE: 25
atgacttggt tgagtttact tgccgatttc agccagata                    39

<210> SEQ ID NO 26
<211> LENGTH: 1335
<212> TYPE: DNA

<213> ORGANISM: Corynebacterium ammoniagenes

<400> SEQUENCE: 26

```
atgacttcaa atatccaaac cagcgaaaca tcttcagaac aaggtggcgg aagtctaaa      60
gaagggttcg tttaccctgg acttctattg ccctttgcat tgatcgtaac ctgctttgca    120
gcgtggggaa tttctaccga cttgaccgcc cccatggtca acgttttag ttccgtattc     180
gatatgagcg cattccaatc tgcgctcgtg cagtctgcat actatggcgc atacttcctg    240
ctcgcgattc cagctgccat gctcaacacc cgcttcggct tcaagggcgg tgtcgttatc    300
ggcatgacgc tagcagccat cggcgcattt ctgttcttcc ctgcggcaga aattatgact    360
ttcggaaccct tcctgctcgc acttttcgtt ctcgcaggtg acttcaat tgttgaaact     420
tccgctaatc cgttcgtaat gtccttaggg cctgagaaaa cgctacgcg acgcttgaac    480
tttgcgcaag catttaaccc tattggttcc aacatcggtg ttctcatggc aacacttctg    540
gtggctccac acatcggaag tgcggttgaa cgtgcatccc tttcagaggc agaagccttg    600
gctcaaacct cctctgaact cgaaaaagtc atggttccat acatcatctt gggtgtactg    660
tacgcgggtc tagcaatcgc tatcttcttt gtaagaatcc ccaagaataa gcgcatgcaa    720
gaaaccgact ccaatacggt tgccaaaggt gtattccttc gcttgtggaa caaccgaact    780
taccgattcg gtgtgattgc acaatttttc aacattgcag cacaaacctg tatctggaca    840
ttcattccgt tctacgtcca gcacacgctc ggagcctcac acgaaacggc cggatggtgg    900
cttcagctat cgcttatctt cttttctcgtc atgcgttttg tcatggtctg gttgatggga    960
aagtacgacg gccgcaagct gttgatattt atgtgtgctt gggagttgt tttcacactc   1020
atcggtgtcc tgtcggagaa cgtggtcggt gctgtggcca ttgctgcact ctctggctgc   1080
atttcgctac tcttcccccac catttacgga gtctctctaa gcggtgtcgg cgctgacacg   1140
aagtttgcct cttctggatt ggtcatggcc atcgtcggcg gcgcagttgc tcctatgatt   1200
cagggcgcga ttacggatgc gaccaaccct cagatcggtt tctcgttcgt aatcctctgc   1260
ttcgtaatca ttggcgcttt tggcctttat gccatcaaga accaagtgga gacaaaggaa   1320
gaatcacatg cttaa                                                     1335
```

<210> SEQ ID NO 27
<211> LENGTH: 444
<212> TYPE: PRT
<213> ORGANISM: Corynebacterium ammoniagenes

<400> SEQUENCE: 27

```
Met Thr Ser Ile Ser Lys Pro Ser Pro Asn Glu Ala Ala Glu Glu Asp
1               5                   10                  15

Lys Lys Ser Lys Gly Ser Phe Val Tyr Pro Gly Leu Leu Leu Pro Phe
            20                  25                  30

Gly Leu Ile Val Ala Cys Phe Ala Ala Trp Gly Ile Ser Thr Asp Leu
        35                  40                  45

Thr Ala Pro Met Val Asn Val Phe Ser Val Phe Asp Met Ser Ala
    50                  55                  60

Phe Gln Ser Ala Leu Val Gln Phe Ala Tyr Tyr Gly Ala Tyr Phe Leu
65                  70                  75                  80

Leu Ala Ile Pro Ala Ala Met Leu Asn Thr Arg Phe Gly Phe Lys Gly
                85                  90                  95

Gly Val Val Ile Gly Met Ser Leu Ala Ala Ile Gly Ala Phe Leu Phe
            100                 105                 110
```

```
Phe Pro Ala Ala Glu Ile Met Thr Tyr Gly Thr Phe Leu Leu Ala Leu
            115                 120                 125
Phe Val Leu Ala Gly Gly Leu Ser Ile Val Glu Thr Ser Ala Asn Pro
        130                 135                 140
Phe Val Met Ser Leu Gly Pro Glu Lys Asn Ala Thr Arg Arg Leu Asn
145                 150                 155                 160
Phe Ala Gln Ala Phe Asn Pro Ile Gly Ser Asn Leu Gly Val Leu Met
                165                 170                 175
Ala Thr Leu Leu Val Ala Pro His Ile Gly Asn Ala Ala Glu Arg Ala
            180                 185                 190
Ser Leu Pro Glu Ala Glu Ala Leu Ala Gln Thr Ser Ser Glu Leu Glu
        195                 200                 205
Arg Val Met Val Pro Tyr Ile Ile Leu Gly Val Leu Tyr Ala Val Leu
        210                 215                 220
Ala Ile Ser Ile Phe Phe Val Lys Ile Pro Lys Asn Lys Arg Met Glu
225                 230                 235                 240
Gln Thr Asp Ser Asn Thr Val Thr Lys Gly Val Phe Arg Arg Leu Trp
                245                 250                 255
Asn Asn Gly Asn Tyr Arg Phe Gly Val Ile Ala Gln Phe Phe Asn Ile
            260                 265                 270
Ala Ala Gln Thr Cys Ile Trp Thr Phe Ile Pro Phe Tyr Val Gln His
        275                 280                 285
Thr Leu Gly Ala Ser His Glu Ala Ala Asp Trp Leu Gln Leu Ser
        290                 295                 300
Leu Ile Phe Phe Leu Val Met Arg Phe Val Met Val Trp Leu Met Gly
305                 310                 315                 320
Lys Phe Asp Ser Lys Lys Leu Leu Val Val Met Cys Val Leu Gly Thr
                325                 330                 335
Val Phe Thr Ile Ile Gly Ile Val Ser Gly Asn Val Ile Gly Ala Val
            340                 345                 350
Ala Ile Ala Ala Leu Ser Gly Cys Ile Ser Leu Leu Phe Pro Thr Ile
        355                 360                 365
Tyr Gly Val Ala Leu Ser Gly Val Gly Ala Asp Thr Lys Phe Ala Ser
        370                 375                 380
Ser Gly Leu Val Met Ala Ile Val Gly Gly Ala Ile Ala Pro Met Leu
385                 390                 395                 400
Gln Gly Ala Leu Thr Asp Ala Thr Asn Pro Gln Ile Gly Phe Ser Phe
                405                 410                 415
Val Val Ile Cys Phe Leu Val Ile Gly Ala Phe Gly Ile Tyr Ser Ile
            420                 425                 430
Lys Asn Gly Ile His Thr His Glu Asp Ala Asn Ala
        435                 440

<210> SEQ ID NO 28
<211> LENGTH: 1326
<212> TYPE: DNA
<213> ORGANISM: Pantoea ananatis

<400> SEQUENCE: 28
atgcaccaga acattgttca gcaaaatgac ggttatctaa ataagactcc gctgttccag      60
ttcattctgc tttcctgcct gttccccttg tggggctgtg cggcaagcct gaatgacatt     120
ctgattacgc agtttaaaag cgttttcgcc ctgagcgatt ttgccagcgc cctggtgcag     180
agcgcctttt acggcggcta ttttctgatt gcgattcctg cctcgctggt gatccgtaaa     240
```

```
accagttaca agctggctat attagccggt ctggcgttgt acatcctggg ctgcctgctg      300
ttttatcccg cctcgcatat ggcaacctac accatgtttc tggcggcgat ttttgccatt      360
gccattgggt taagctttct ggagacggcg gcgaacacct acagctcaat gatcggacag      420
cgtcagcatg ccacgctgcg tcttaacatc agtcagacgt tttatccggt ggggcgctg       480 atgggcattg tgctgggaaa atatctggtg tttcaggatg gagaaagcct ggaaacgcaa      540
atggcaaaca tgacggcggc gcaggcgcat gctttccgcc tgtccatgct ggaacatacc      600
ctggaaccct ataaatatct ggtgatggtg ctggtggttg tcatgctgct gtttatgttc      660
acccgctatc cacgctgcaa gccgcaaagc aacgaaaaat cgctgccaac gctgggggaa      720
acctttcgct atctggctaa aaatcgccat tttaaacgcg gtattctggc gcagttttg       780 tacgtcggta tgcaggtggc ggtgtggtcc tttaccatcc gtctggcgct tacgttggga      840
gctgccaatg agcgcgaggc atccagcttt atgatttaca gctttatctg tttctttatt      900
ggcaagtttg tcgccaacat tttaatgacg cgtttccggc cagagaaagt gcttatcgcc      960
ttttcactcc ttggcatcgc aacgctgggc tacgtgatgc tggtgcccaa tttcacagca     1020
gtctacgccg cggtgtttgt cagcgtgctg tttggcccgt gctgggcgac gatctatgcc     1080
gggacgctcg cgaccgttga cagtaaatac accgaagtcg cgggagcatt tattgtgatg     1140
tccattgtgg gtgcggcctt tgtgcccgcg ctgcagggct tgtttccga tcacctggga      1200 tcgatgcagc tggcattcgg cgtatcgctg ctgtgtttcg catgggttgg gttctatttt     1260
tggggcgagc tgcgccacaa aaagcagcct cgccttagcg gaaacctggc ggaggagggg     1320
cgatga                                                                1326
```

<210> SEQ ID NO 29
<211> LENGTH: 441
<212> TYPE: PRT
<213> ORGANISM: Pantoea ananatis

<400> SEQUENCE: 29

```
Met His Gln Asn Ile Val Gln Gln Asn Asp Gly Tyr Leu Asn Lys Thr
1               5                   10                  15

Pro Leu Phe Gln Phe Ile Leu Leu Ser Cys Leu Phe Pro Leu Trp Gly
            20                  25                  30

Cys Ala Ala Ser Leu Asn Asp Ile Leu Ile Thr Gln Phe Lys Ser Val
        35                  40                  45

Phe Ala Leu Ser Asp Phe Ala Ser Ala Leu Val Gln Ser Ala Phe Tyr
    50                  55                  60

Gly Gly Tyr Phe Leu Ile Ala Ile Pro Ala Ser Leu Val Ile Arg Lys
65                  70                  75                  80

Thr Ser Tyr Lys Leu Ala Ile Leu Ala Gly Leu Ala Leu Tyr Ile Leu
                85                  90                  95

Gly Cys Leu Leu Phe Tyr Pro Ala Ser His Met Ala Thr Tyr Thr Met
            100                 105                 110

Phe Leu Ala Ala Ile Phe Ala Ile Ala Ile Gly Leu Ser Phe Leu Glu
        115                 120                 125

Thr Ala Ala Asn Thr Tyr Ser Ser Met Ile Gly Gln Arg Gln His Ala
    130                 135                 140

Thr Leu Arg Leu Asn Ile Ser Gln Thr Phe Tyr Pro Val Gly Ala Leu
145                 150                 155                 160

Met Gly Ile Val Leu Gly Lys Tyr Leu Val Phe Gln Asp Gly Glu Ser
                165                 170                 175
```

```
Leu Glu Thr Gln Met Ala Asn Met Thr Ala Ala Gln Ala His Ala Phe
            180                 185                 190

Arg Leu Ser Met Leu Glu His Thr Leu Glu Pro Tyr Lys Tyr Leu Val
        195                 200                 205

Met Val Leu Val Val Val Met Leu Leu Phe Met Phe Thr Arg Tyr Pro
    210                 215                 220

Arg Cys Lys Pro Gln Ser Asn Glu Lys Ser Leu Pro Thr Leu Gly Glu
225                 230                 235                 240

Thr Phe Arg Tyr Leu Ala Lys Asn Arg His Phe Lys Arg Gly Ile Leu
            245                 250                 255

Ala Gln Phe Leu Tyr Val Gly Met Gln Val Ala Val Trp Ser Phe Thr
        260                 265                 270

Ile Arg Leu Ala Leu Thr Leu Gly Ala Ala Asn Glu Arg Glu Ala Ser
    275                 280                 285

Ser Phe Met Ile Tyr Ser Phe Ile Cys Phe Phe Ile Gly Lys Phe Val
        290                 295                 300

Ala Asn Ile Leu Met Thr Arg Phe Arg Pro Glu Lys Val Leu Ile Ala
305                 310                 315                 320

Phe Ser Leu Leu Gly Ile Ala Thr Leu Gly Tyr Val Met Leu Val Pro
            325                 330                 335

Asn Phe Thr Ala Val Tyr Ala Ala Val Phe Ser Val Leu Phe Gly
        340                 345                 350

Pro Cys Trp Ala Thr Ile Tyr Ala Gly Thr Leu Ala Thr Val Asp Ser
    355                 360                 365

Lys Tyr Thr Glu Val Ala Gly Ala Phe Ile Val Met Ser Ile Val Gly
        370                 375                 380

Ala Ala Phe Val Pro Ala Leu Gln Gly Phe Val Ser Asp His Leu Gly
385                 390                 395                 400

Ser Met Gln Leu Ala Phe Gly Val Ser Leu Leu Cys Phe Ala Trp Val
            405                 410                 415

Gly Phe Tyr Phe Trp Gly Glu Leu Arg His Lys Lys Gln Pro Arg Leu
        420                 425                 430

Ser Gly Asn Leu Ala Glu Glu Gly Arg
        435                 440

<210> SEQ ID NO 30
<211> LENGTH: 897
<212> TYPE: DNA
<213> ORGANISM: Bifidobacterium longum

<400> SEQUENCE: 30
atgactaccc cgatcgttct gagcctcggt gaactgctgt gggacatgct gccgagcggc      60
aagcgagccg gcggcgcccc cgtcaacttc gcctaccacg cgatgaagaa cggcaccgaa     120
ggctgggcca tcagcgcggt cggcgaggat gaactcggcg acgaactgat tgccaaggcc     180
gacgaggccg gcatcaacac cgttcttcag cgcaacgcct ggccgacctc caccgtcgaa     240
gtcgcactga agaacggtat cccggagtac accatcgtca agggcgtggc ttgggaccac     300
atcctgtaca cccgccagct catcgacgtg gtctccaagg ccgacgccgt ctgcttcggc     360
accctggccc tgcgctcccc cgaatcgcac gccaccatca cggagctgct caagcacacc     420
aagccgggcg cgatgaagtt cttcgacatc aacctgcgcg cgaccactac tccaaggaa     480 cttatcgagg aactcctcaa ggcggccacc gtcttcaaga tcaacgacga ggaactcctg     540
ctgctgcgcg acatgttcga cattcgcggc acctccggcg aagacgcctc ccgctggttc     600
```

```
ctcgaggaat cgacctcga ctacgtgatt ctgaccgccg gctccgccta ctccaccatc    660
atctcccgca agggcgaggt ctccacgctg acactccgc acgtcgaggt gaacgacacc    720
gtgggtgcag gtgactcctt ctccggcacc ttcaccgcac gcatcctgct gggtgacacg    780
ctcgccgaag cccaccgcaa ggccgtcaac accgccgcct cgtctgcac ccaggccggt    840 gcctggcccg agtacccggc cgagatgccc gactatctgg ctgaaatcgg caagtaa      897
```

<210> SEQ ID NO 31
<211> LENGTH: 298
<212> TYPE: PRT
<213> ORGANISM: Bifidobacterium longum
<400> SEQUENCE: 31

```
Met Thr Thr Pro Ile Val Leu Ser Leu Gly Glu Leu Leu Trp Asp Met
1               5                   10                  15

Leu Pro Ser Gly Lys Arg Ala Gly Gly Ala Pro Val Asn Phe Ala Tyr
            20                  25                  30

His Ala Met Lys Asn Gly Thr Glu Gly Trp Ala Ile Ser Ala Val Gly
        35                  40                  45

Glu Asp Glu Leu Gly Asp Glu Leu Ile Ala Lys Ala Asp Glu Ala Gly
    50                  55                  60

Ile Asn Thr Val Leu Gln Arg Asn Ala Trp Pro Thr Ser Thr Val Glu
65                  70                  75                  80

Val Ala Leu Lys Asn Gly Ile Pro Glu Tyr Thr Ile Val Lys Gly Val
                85                  90                  95

Ala Trp Asp His Ile Leu Tyr Thr Arg Gln Leu Ile Asp Val Val Ser
            100                 105                 110

Lys Ala Asp Ala Val Cys Phe Gly Thr Leu Ala Leu Arg Ser Pro Glu
        115                 120                 125

Ser His Ala Thr Ile Thr Glu Leu Leu Lys His Thr Lys Pro Gly Ala
    130                 135                 140

Met Lys Phe Phe Asp Ile Asn Leu Arg Gly Asp His Tyr Ser Lys Glu
145                 150                 155                 160

Leu Ile Glu Glu Leu Leu Lys Ala Ala Thr Val Phe Lys Ile Asn Asp
                165                 170                 175

Glu Glu Leu Leu Leu Leu Arg Asp Met Phe Asp Ile Arg Gly Thr Ser
            180                 185                 190

Gly Glu Asp Ala Ser Arg Trp Phe Leu Glu Glu Phe Asp Leu Asp Tyr
        195                 200                 205

Val Ile Leu Thr Ala Gly Ser Ala Tyr Ser Thr Ile Ile Ser Arg Lys
    210                 215                 220

Gly Glu Val Ser Thr Leu Asp Thr Pro His Val Glu Val Asn Asp Thr
225                 230                 235                 240

Val Gly Ala Gly Asp Ser Phe Ser Gly Thr Phe Thr Ala Arg Ile Leu
                245                 250                 255

Leu Gly Asp Thr Leu Ala Glu Ala His Arg Lys Ala Val Asn Thr Ala
            260                 265                 270

Ala Phe Val Cys Thr Gln Ala Gly Ala Trp Pro Glu Tyr Pro Ala Glu
        275                 280                 285

Met Pro Asp Tyr Leu Ala Glu Ile Gly Lys
    290                 295
```

<210> SEQ ID NO 32
<211> LENGTH: 906
<212> TYPE: DNA

<213> ORGANISM: Pantoea ananatis

<400> SEQUENCE: 32

```
gtgcgcatag gcattgattt gggcggcacc aaaacagaag tgattgcgct gtccggcgag    60
ggaaaagagc tgtttcgcca tcggatttcc acgccccgtg acgactaccg gcgaccgtg   120
caggccatcg ttgatttagt ccgcctcgcc gaagaaaaaa ccggccaaac cgggacggta   180
ggcttaggta ttccgggcac gatttcgccc tatacgcagc gggtgaaaaa cgcgaactcc   240
acctggctaa acggtcagcc gctggataaa gatttggcgc aggcgctgaa tcgtgacatc   300
cgcatagcca atgacgcgaa ttgtctggcc gtgtccgaag cggtcgatgg cgcaggcgcg   360
gggcaggcac tggtgtttgg ggtaatcatc ggcaccggtt cgggcgcagg cgtagcgata   420
aacggcgcgt cacgcattgg cggcaacggc aatgcgggcg aatggggtca taatcctttg   480
ccgtggatgg atgaagacga gttgcgttac cgcgcggaag tcccctgtta ttgtggccag   540
cagggctgca ttgaaaacctt tgtttccggt accggctttg ctatcgacta tcagcggtta   600
agcggtgtgg cgcgcaaagg cgctgagatt gtcaaactgc tggagcagca ggatcccgtg   660
gctgccctgg caatgagccg ctatgaaatc cgtctggcaa atccctggc tcaggttgtc   720
aacctgatcg atcccgacgt gattgtgctg ggcggcggca tgagcaacgt ggaccgcctg   780
taccagacgg tgcccacgct gatgaagaaa tgggttttg cggcgagtg tgaaacgccg   840
gtgctgaaag cgatgcacgg ggattcaagc ggtgtgcgcg cgcggcctg gctgtggccg   900
gaataa                                                              906
```

<210> SEQ ID NO 33
<211> LENGTH: 301
<212> TYPE: PRT
<213> ORGANISM: Pantoea ananatis

<400> SEQUENCE: 33

```
Met Arg Ile Gly Ile Asp Leu Gly Gly Thr Lys Thr Glu Val Ile Ala
1               5                  10                  15

Leu Ser Gly Glu Gly Lys Glu Leu Phe Arg His Arg Ile Ser Thr Pro
                20                  25                  30

Arg Asp Asp Tyr Arg Ala Thr Val Gln Ala Ile Val Asp Leu Val Arg
            35                  40                  45

Leu Ala Glu Glu Lys Thr Gly Gln Thr Gly Thr Val Gly Leu Gly Ile
        50                  55                  60

Pro Gly Thr Ile Ser Pro Tyr Thr Gln Arg Val Lys Asn Ala Asn Ser
65                  70                  75                  80

Thr Trp Leu Asn Gly Gln Pro Leu Asp Lys Asp Leu Ala Gln Ala Leu
                85                  90                  95

Asn Arg Asp Ile Arg Ile Ala Asn Asp Ala Asn Cys Leu Ala Val Ser
            100                 105                 110

Glu Ala Val Asp Gly Ala Gly Ala Gln Ala Leu Val Phe Gly Val
        115                 120                 125

Ile Ile Gly Thr Gly Ser Gly Ala Gly Val Ala Ile Asn Gly Ala Ser
    130                 135                 140

Arg Ile Gly Gly Asn Gly Asn Ala Gly Glu Trp Gly His Asn Pro Leu
145                 150                 155                 160

Pro Trp Met Asp Glu Asp Glu Leu Arg Tyr Arg Ala Glu Val Pro Cys
                165                 170                 175

Tyr Cys Gly Gln Gln Gly Cys Ile Glu Thr Phe Val Ser Gly Thr Gly
            180                 185                 190
```

Phe Ala Ile Asp Tyr Gln Arg Leu Ser Gly Val Ala Arg Lys Gly Ala
            195                 200                 205

Glu Ile Val Lys Leu Leu Glu Gln Gln Asp Pro Val Ala Ala Leu Ala
        210                 215                 220

Met Ser Arg Tyr Glu Ile Arg Leu Ala Lys Ser Leu Ala Gln Val Val
225                 230                 235                 240

Asn Leu Ile Asp Pro Asp Val Ile Val Leu Gly Gly Met Ser Asn
            245                 250                 255

Val Asp Arg Leu Tyr Gln Thr Val Pro Thr Leu Met Lys Lys Trp Val
            260                 265                 270

Phe Gly Gly Glu Cys Glu Thr Pro Val Leu Lys Ala Met His Gly Asp
            275                 280                 285

Ser Ser Gly Val Arg Gly Ala Ala Trp Leu Trp Pro Glu
            290                 295                 300

<210> SEQ ID NO 34
<211> LENGTH: 918
<212> TYPE: DNA
<213> ORGANISM: Pantoea ananatis

<400> SEQUENCE: 34

```
atgtcagcac gagtctggtg tctgggtgat gccgtggtgg acctgcttcc ggacgggccg      60
gggcatttaa tacagtgtgc aggcggggcg cccgccaatg tggcggtggg cattgcccgc     120
ttacagggcc gcagcgggtt tattggccgg gttggggacg atccttttgg tcactttatg     180
cagcacacgc tggcgactga acaggttgat acccgctata tgacgctgga cagcgcccag     240
cgcacctcaa cggtggtggt ggcgctggat caggaaggtg agcggacttt tacctttatg     300
gtgcgcccca gtgcagatct gtttctggaa caaggcgatc tccccaggtt tgagcaaggt     360
gaatggcttc actgctgctc aattgccctg cggcagaaac cttcgcgctc caccaccttt     420
tctgccatgc agcagatcag cgatgccggt ggctttgtga gctttgatcc caatattcgt     480
cacgatctgt ggcacgacga tgcccaactg cgggactgtg tgaaccgggc gttacagctg     540
gccgatgtgg tcaagctgtc tgaggaagag ctggcttttc tgactccggg ggcgcaacac     600
gctgacagca tgcaggcgct ggcggaacgc tttgcgatta gcctgctgat ggtcacccag     660
ggcaaggcag gagtgaaagt ctggcatcag ggtaaacatt atcactatcc cacgctgcct     720
gtggtgagcg tggacaccac cggcgcaggg gatgcgtttg tcgccgggct gctatggggg     780
ctggcggaaa aggggatgcc cgctaatgag gccgagctgg cggcacgact cagcagcgca     840
cagcagtgtg gggcgctggc gacgacggca aaaggggcca tgaccgcgtt gccttatcgt     900
caccaaattg aaggatga                                                   918
```

<210> SEQ ID NO 35
<211> LENGTH: 305
<212> TYPE: PRT
<213> ORGANISM: Pantoea ananatis

<400> SEQUENCE: 35

Met Ser Ala Arg Val Trp Cys Leu Gly Asp Ala Val Val Asp Leu Leu
1               5                   10                  15

Pro Asp Gly Pro Gly His Leu Ile Gln Cys Ala Gly Gly Ala Pro Ala
            20                  25                  30

Asn Val Ala Val Gly Ile Ala Arg Leu Gln Gly Arg Ser Gly Phe Ile
        35                  40                  45

-continued

```
Gly Arg Val Gly Asp Asp Pro Phe Gly His Phe Met Gln His Thr Leu
    50                  55                  60

Ala Thr Glu Gln Val Asp Thr Arg Tyr Met Thr Leu Asp Ser Ala Gln
65                  70                  75                  80

Arg Thr Ser Thr Val Val Val Ala Leu Asp Gln Glu Gly Glu Arg Thr
                85                  90                  95

Phe Thr Phe Met Val Arg Pro Ser Ala Asp Leu Phe Leu Glu Gln Gly
            100                 105                 110

Asp Leu Pro Arg Phe Glu Gln Gly Glu Trp Leu His Cys Cys Ser Ile
            115                 120                 125

Ala Leu Ala Ala Glu Pro Ser Arg Ser Thr Thr Phe Ser Ala Met Gln
130                 135                 140

Gln Ile Ser Asp Ala Gly Gly Phe Val Ser Phe Asp Pro Asn Ile Arg
145                 150                 155                 160

His Asp Leu Trp His Asp Ala Gln Leu Arg Asp Cys Val Asn Arg
            165                 170                 175

Ala Leu Gln Leu Ala Asp Val Val Lys Leu Ser Glu Glu Glu Leu Ala
            180                 185                 190

Phe Leu Thr Pro Gly Ala Gln His Ala Asp Ser Met Gln Ala Leu Ala
            195                 200                 205

Glu Arg Phe Ala Ile Ser Leu Leu Met Val Thr Gln Gly Lys Ala Gly
    210                 215                 220

Val Lys Val Trp His Gln Gly Lys His Tyr His Tyr Pro Thr Leu Pro
225                 230                 235                 240

Val Val Ser Val Asp Thr Thr Gly Ala Gly Asp Ala Phe Val Ala Gly
                245                 250                 255

Leu Leu Trp Gly Leu Ala Glu Lys Gly Met Pro Ala Asn Glu Ala Glu
            260                 265                 270

Leu Ala Ala Arg Leu Ser Ser Ala Gln Gln Cys Gly Ala Leu Ala Thr
            275                 280                 285

Thr Ala Lys Gly Ala Met Thr Ala Leu Pro Tyr Arg His Gln Ile Glu
    290                 295                 300

Gly
305
```